US008905922B2

(12) United States Patent
Makower et al.

(10) Patent No.: US 8,905,922 B2

(45) Date of Patent: Dec. 9, 2014

(54) DEVICES, SYSTEMS AND METHODS FOR DIAGNOSING AND TREATING SINUSITIS AND OTHER DISORDERS OF THE EARS, NOSE AND/OR THROAT

(75) Inventors: Joshua Makower, Los Altos, CA (US); John Y. Chang, Mountain View, CA (US)

(73) Assignee: Acclarent, Inc., Menlo Park, CA (US)

( * ) Notice: Subject to any disclaimer, the term of this patent is extended or adjusted under 35 U.S.C. 154(b) by 39 days.

(21) Appl. No.: 13/429,857

(22) Filed: Mar. 26, 2012

(65) Prior Publication Data

US 2012/0245419 A1 Sep. 27, 2012

Related U.S. Application Data

(63) Continuation of application No. 12/042,221, filed on Mar. 4, 2008, now Pat. No. 8,142,422, which is a continuation of application No. 10/829,917, filed on Apr. 21, 2004, now Pat. No. 7,654,997.

(51) Int. Cl.

*A61B 1/06* (2006.01)

*A61B 17/3205* (2006.01)

(Continued)

(52) U.S. Cl.

CPC ........... *A61B 17/24* (2013.01); *A61B 17/32053* (2013.01); *A61B 17/3478* (2013.01); *A61B 17/320758* (2013.01); *A61B 2017/22061* (2013.01); *A61B 17/320783* (2013.01); *A61F 2250/0039* (2013.01); *A61F 2/18* (2013.01); *A61F 2/82* (2013.01); *A61B 17/320725* (2013.01)

USPC ............................................... 600/182; 606/2

(58) Field of Classification Search

USPC ...................................... 606/2; 600/178, 182

See application file for complete search history.

(56) References Cited

U.S. PATENT DOCUMENTS

| | | | |
|---|---|---|---|
| 446,173 | A | 2/1891 | Hancock |
| 504,424 | A | 9/1893 | De Pezzer |

(Continued)

FOREIGN PATENT DOCUMENTS

| | | |
|---|---|---|
| CA | 2013323 | 9/1990 |
| CH | 668188 | 12/1988 |

(Continued)

OTHER PUBLICATIONS

Becker, A.E. 'Restenosis After Angioplasty' The Lancet (1988) vol. 331, No. 8584 p. 532.

(Continued)

*Primary Examiner* — Kevin C Sirmons

*Assistant Examiner* — Deanna K Hall

(74) *Attorney, Agent, or Firm* — Frost Brown Todd LLC

(57) ABSTRACT

Sinusitis, enlarged nasal turbinates, tumors, infections, hearing disorders, allergic conditions, facial fractures and other disorders of the ear, nose and throat are diagnosed and/or treated using minimally invasive approaches and, in many cases, flexible catheters as opposed to instruments having rigid shafts. Various diagnostic procedures and devices are used to perform imaging studies, mucus flow studies, air/gas flow studies, anatomic dimension studies, endoscopic studies and transillumination studies. Access and occluder devices may be used to establish fluid tight seals in the anterior or posterior nasal cavities/nasopharynx and to facilitate insertion of working devices (e.g., scopes, guidewires, catheters, tissue cutting or remodeling devices, electrosurgical devices, energy emitting devices, devices for injecting diagnostic or therapeutic agents, devices for implanting devices such as stents, substance eluting devices, substance delivery implants, etc.

11 Claims, 41 Drawing Sheets

(51) Int. Cl.

| | |
|---|---|
| ***A61B 17/24*** | (2006.01) |
| *A61B 17/34* | (2006.01) |
| *A61B 17/3207* | (2006.01) |
| *A61B 17/22* | (2006.01) |
| *A61F 2/18* | (2006.01) |
| *A61F 2/82* | (2013.01) |

(56) References Cited

U.S. PATENT DOCUMENTS

| | | | |
|---|---|---|---|
| 513,667 | A | 1/1894 | Buckingham |
| 705,346 | A | 7/1902 | Hamilton |
| 798,775 | A | 9/1905 | Forsyte |
| 816,792 | A | 4/1906 | Green |
| 1,080,934 | A | 12/1913 | Shackleford |
| 1,200,267 | A | 10/1916 | Sunnergren |
| 1,650,959 | A | 11/1927 | Pitman |
| 1,735,519 | A | 11/1929 | Vance |
| 1,828,986 | A | 10/1931 | Stevens |
| 1,878,671 | A | 9/1932 | Cantor |
| 2,201,749 | A | 5/1940 | Vandegrift |
| 2,493,326 | A | 1/1950 | Trinder |
| 2,525,183 | A | 10/1950 | Robison |
| 2,847,997 | A | 8/1958 | Tibone |
| 2,899,227 | A | 8/1959 | Jeanrenaud |
| 2,906,179 | A | 9/1959 | Bower |
| 2,995,832 | A | 8/1961 | Alderson |
| 3,009,265 | A | 11/1961 | Bexark |
| 3,037,286 | A | 6/1962 | Bower |
| 3,173,418 | A | 3/1965 | Baran |
| 3,347,061 | A | 10/1967 | Stuemky |
| 3,376,659 | A | 4/1968 | Asin et al. |
| 3,384,970 | A | 5/1968 | Avalear |
| 3,393,073 | A | 7/1968 | Reutenauer et al. |
| 3,435,826 | A | 4/1969 | Fogarty |
| 3,447,061 | A | 5/1969 | Russell et al. |
| 3,469,578 | A | 9/1969 | Bierman |
| 3,481,043 | A | 12/1969 | Esch |
| 3,486,539 | A | 12/1969 | Jacuzzi |
| 3,506,005 | A | 4/1970 | Gilio et al. |
| 3,509,638 | A | 5/1970 | Macleod |
| 3,515,888 | A | 6/1970 | Lewis |
| 3,527,220 | A | 9/1970 | Summers |
| 3,531,868 | A | 10/1970 | Stevenson |
| 3,552,384 | A | 1/1971 | Pierie et al. |
| 3,731,963 | A | 4/1971 | Pond |
| 3,624,661 | A | 11/1971 | Shebanow |
| 3,766,924 | A | 10/1973 | Pidgeon |
| 3,792,391 | A | 2/1974 | Ewing |
| 3,800,788 | A | 4/1974 | White |
| 3,802,096 | A | 4/1974 | Matern |
| 3,804,081 | A | 4/1974 | Kinoshita |
| 3,834,394 | A | 9/1974 | Hunter et al. |
| 3,847,145 | A | 11/1974 | Grossan |
| 3,850,176 | A | 11/1974 | Gottschalk |
| 3,856,000 | A | 12/1974 | Chikama |
| 3,859,993 | A | 1/1975 | Bitner |
| 3,871,365 | A | 3/1975 | Chikama |
| 3,894,538 | A | 7/1975 | Richter |
| 3,903,893 | A | 9/1975 | Scheer |
| 3,910,617 | A | 10/1975 | Scalza et al. |
| 3,921,636 | A | 11/1975 | Zaffaroni |
| 3,948,254 | A | 4/1976 | Zaffaroni |
| 3,948,262 | A | 4/1976 | Zaffaroni |
| 3,967,618 | A | 7/1976 | Zaffaroni |
| 3,993,069 | A | 11/1976 | Buckles et al. |
| 3,993,072 | A | 11/1976 | Zaffaroni |
| 3,993,073 | A | 11/1976 | Zaffaroni |
| 4,016,251 | A | 4/1977 | Higuchi et al. |
| 4,052,505 | A | 10/1977 | Higuchi et al. |
| 4,053,975 | A | 10/1977 | Olbrich et al. |
| 4,069,307 | A | 1/1978 | Higuchi et al. |
| 4,102,342 | A | 7/1978 | Akiyama et al. |
| 4,138,151 | A | 2/1979 | Nakao |
| 4,184,497 | A | 1/1980 | Kolff et al. |
| 4,198,766 | A | 4/1980 | Camin et al. |
| 4,207,890 | A | 6/1980 | Mamajek et al. |
| 4,209,919 | A | 7/1980 | Kirikae et al. |
| 4,213,095 | A | 7/1980 | Falconer |
| 4,217,898 | A | 8/1980 | Theeuwes |
| 4,268,115 | A | 5/1981 | Slemon et al. |
| 4,299,226 | A | 11/1981 | Banka |
| 4,299,227 | A | 11/1981 | Lincoff |
| 4,312,353 | A | 1/1982 | Shahbabian |
| 4,338,941 | A | 7/1982 | Payton |
| D269,204 | S | 5/1983 | Trepp |
| 4,388,941 | A | 6/1983 | Riedhammer |
| RE31,351 | E | 8/1983 | Falconer |
| 4,435,716 | A | 3/1984 | Zandbergen |
| 4,437,856 | A | 3/1984 | Valli |
| 4,450,150 | A | 5/1984 | Sidman |
| 4,459,977 | A | 7/1984 | Pizon et al. |
| 4,464,175 | A | 8/1984 | Altman et al. |
| 4,471,779 | A | 9/1984 | Antoshkiw et al. |
| 4,499,899 | A | 2/1985 | Lyons, III |
| 4,554,929 | A | 11/1985 | Samson et al. |
| 4,564,364 | A | 1/1986 | Zaffaroni et al. |
| 4,571,239 | A | 2/1986 | Heyman |
| 4,571,240 | A | 2/1986 | Samson et al. |
| 4,581,017 | A | 4/1986 | Sahota |
| 4,585,000 | A | 4/1986 | Hershenson |
| D283,921 | S | 5/1986 | Dyak |
| 4,589,868 | A | 5/1986 | Dretler |
| 4,596,528 | A | 6/1986 | Lewis et al. |
| D284,892 | S | 7/1986 | Glassman |
| 4,603,564 | A | 8/1986 | Kleinhany et al. |
| 4,606,346 | A | 8/1986 | Berg et al. |
| 4,607,622 | A | 8/1986 | Fritch et al. |
| 4,637,389 | A | 1/1987 | Heyden |
| 4,639,244 | A | 1/1987 | Rizk et al. |
| 4,645,495 | A | 2/1987 | Vaillancourt |
| 4,669,469 | A | 6/1987 | Gifford, III |
| 4,672,961 | A | 6/1987 | Davies |
| 4,675,613 | A | 6/1987 | Naegeli et al. |
| 4,691,948 | A | 9/1987 | Austin, Jr. et al. |
| 4,708,434 | A | 11/1987 | Tsuno |
| 4,708,834 | A | 11/1987 | Cohen et al. |
| 4,726,772 | A | 2/1988 | Amplatz |
| 4,736,970 | A | 4/1988 | McGourty et al. |
| 4,737,141 | A | 4/1988 | Spits |
| 4,748,869 | A | 6/1988 | Ohtsuka |
| 4,748,969 | A | 6/1988 | Wardle |
| 4,748,986 | A | 6/1988 | Morrison et al. |
| 4,755,171 | A | 7/1988 | Tennant |
| 4,771,776 | A | 9/1988 | Powell et al. |
| 4,793,359 | A | 12/1988 | Sharrow |
| 4,795,439 | A | 1/1989 | Guest |
| 4,796,629 | A | 1/1989 | Grayzel |
| 4,803,076 | A | 2/1989 | Ranade |
| 4,811,743 | A | 3/1989 | Stevens |
| 4,815,478 | A | 3/1989 | Buchbinder et al. |
| 4,819,619 | A | 4/1989 | Augustine et al. |
| 4,846,186 | A | 7/1989 | Box et al. |
| 4,847,258 | A | 7/1989 | Sturm et al. |
| 4,851,228 | A | 7/1989 | Zentner et al. |
| 4,854,330 | A | 8/1989 | Evans, III et al. |
| 4,862,874 | A | 9/1989 | Kellner |
| 4,867,138 | A | 9/1989 | Kubota et al. |
| 4,883,465 | A | 11/1989 | Brennan |
| 4,897,651 | A | 1/1990 | DeMonte |
| 4,898,577 | A | 2/1990 | Badger et al. |
| 4,917,419 | A | 4/1990 | Mora, Jr. et al. |
| 4,917,667 | A | 4/1990 | Jackson |
| 4,919,112 | A | 4/1990 | Siegmund |
| 4,920,967 | A | 5/1990 | Cottonaro et al. |
| 4,925,445 | A | 5/1990 | Sakamoto et al. |
| 4,940,062 | A | 7/1990 | Hampton et al. |
| 4,943,275 | A | 7/1990 | Stricker |
| 4,946,466 | A | 8/1990 | Pinchuk et al. |
| 4,961,433 | A | 10/1990 | Christian |
| 4,966,163 | A | 10/1990 | Kraus et al. |
| 4,984,581 | A | 1/1991 | Stice |
| 4,994,033 | A | 2/1991 | Shockey et al. |
| 4,998,916 | A | 3/1991 | Hammerslag et al. |

(56) References Cited

U.S. PATENT DOCUMENTS

| | | | | |
|---|---|---|---|---|
| 4,998,917 | A | | 3/1991 | Gaiser et al. |
| 5,001,825 | A | | 3/1991 | Halpern |
| 5,002,322 | A | | 3/1991 | Fukumoto |
| 5,009,655 | A | | 4/1991 | Daignault, Jr. et al. |
| 5,019,075 | A | | 5/1991 | Spears et al. |
| 5,019,372 | A | | 5/1991 | Folkman et al. |
| 5,020,514 | A | | 6/1991 | Heckele |
| 5,021,043 | A | | 6/1991 | Becker et al. |
| 5,024,650 | A | | 6/1991 | Hagiwara et al. |
| 5,024,658 | A | | 6/1991 | Kozlov et al. |
| 5,026,384 | A | | 6/1991 | Farr et al. |
| 5,030,227 | A | | 7/1991 | Rosenbluth et al. |
| 5,041,089 | A | | 8/1991 | Mueller et al. |
| 5,044,678 | A | | 9/1991 | Detweiler |
| 5,053,007 | A | | 10/1991 | Euteneuer |
| 5,055,051 | A | | 10/1991 | Duncan |
| 5,060,660 | A | | 10/1991 | Gamble et al. |
| 5,067,489 | A | | 11/1991 | Lind |
| 5,069,226 | A | | 12/1991 | Tamauchi et al. |
| 5,087,244 | A | | 2/1992 | Wolinsky et al. |
| 5,087,246 | A | | 2/1992 | Smith |
| 5,090,595 | A | | 2/1992 | Vandeninck |
| 5,090,910 | A | | 2/1992 | Narlo |
| 5,102,402 | A | | 4/1992 | Dror et al. |
| 5,112,228 | A | | 5/1992 | Zouras |
| 5,116,311 | A | | 5/1992 | Lofstedt |
| 5,127,393 | A | | 7/1992 | McFarlin et al. |
| 5,137,517 | A | | 8/1992 | Loney et al. |
| 5,139,510 | A | | 8/1992 | Goldsmith, III et al. |
| 5,139,832 | A | | 8/1992 | Hayashi et al. |
| D329,496 | S | | 9/1992 | Wotton |
| 5,152,747 | A | | 10/1992 | Olivier |
| 5,156,595 | A | | 10/1992 | Adams |
| 5,163,989 | A | | 11/1992 | Campbell et al. |
| 5,167,220 | A | | 12/1992 | Brown |
| 5,168,864 | A | | 12/1992 | Shockey |
| 5,169,043 | A | | 12/1992 | Catania |
| 5,169,386 | A | | 12/1992 | Becker et al. |
| 5,171,233 | A | | 12/1992 | Amplatz et al. |
| 5,180,368 | A | | 1/1993 | Garrison |
| 5,183,470 | A | | 2/1993 | Wettermann |
| 5,189,110 | A | | 2/1993 | Ikematu et al. |
| 5,195,168 | A | | 3/1993 | Yong |
| 5,197,457 | A | | 3/1993 | Adair |
| 5,207,695 | A | | 5/1993 | Trout, III |
| 5,211,952 | A | | 5/1993 | Spicer et al. |
| 5,215,105 | A | | 6/1993 | Kizelshteyn et al. |
| 5,221,260 | A | | 6/1993 | Burns et al. |
| 5,226,302 | A | | 7/1993 | Anderson |
| 5,230,348 | A | | 7/1993 | Ishibe et al. |
| 5,236,422 | A | | 8/1993 | Eplett, Jr. |
| 5,238,004 | A | | 8/1993 | Sahatjian et al. |
| 5,243,996 | A | | 9/1993 | Hall |
| D340,111 | S | | 10/1993 | Yoshikawa |
| 5,250,059 | A | | 10/1993 | Andreas et al. |
| 5,251,092 | A | | 10/1993 | Brady et al. |
| 5,252,183 | A | | 10/1993 | Shaban et al. |
| 5,255,679 | A | | 10/1993 | Imran |
| 5,256,144 | A | | 10/1993 | Kraus et al. |
| 5,263,926 | A | | 11/1993 | Wilk |
| 5,264,260 | A | | 11/1993 | Saab |
| 5,267,965 | A | | 12/1993 | Deneiga |
| 5,269,752 | A | | 12/1993 | Bennett |
| 5,270,086 | A | | 12/1993 | Hamlin |
| 5,273,052 | A | | 12/1993 | Kraus et al. |
| 5,275,593 | A | | 1/1994 | Easley et al. |
| 5,286,254 | A | | 2/1994 | Shapland et al. |
| 5,290,310 | A | | 3/1994 | Makower et al. |
| 5,295,694 | A | | 3/1994 | Levin |
| 5,300,085 | A | | 4/1994 | Yock |
| 5,304,123 | A | | 4/1994 | Atala et al. |
| 5,308,326 | A | | 5/1994 | Zimmon |
| 5,312,430 | A | | 5/1994 | Rosenbluth et al. |
| 5,313,967 | A | | 5/1994 | Lieber et al. |
| 5,314,408 | A | | 5/1994 | Salmon et al. |
| 5,314,417 | A | | 5/1994 | Stephens et al. |
| 5,315,618 | A | | 5/1994 | Yoshida |
| 5,318,528 | A | | 6/1994 | Heaven et al. |
| 5,324,306 | A | | 6/1994 | Makower et al. |
| 5,333,620 | A | | 8/1994 | Moutafis et al. |
| 5,334,167 | A | | 8/1994 | Cocanower |
| 5,334,187 | A | | 8/1994 | Fischell et al. |
| 5,335,671 | A | | 8/1994 | Clement |
| 5,336,163 | A | | 8/1994 | DeMane et al. |
| 5,341,818 | A | | 8/1994 | Abrams et al. |
| 5,342,296 | A | | 8/1994 | Persson et al. |
| 5,343,865 | A | | 9/1994 | Gardineer et al. |
| 5,345,945 | A | | 9/1994 | Hodgson et al. |
| 5,346,075 | A | | 9/1994 | Nichols et al. |
| 5,346,508 | A | | 9/1994 | Hastings |
| 5,348,537 | A | | 9/1994 | Wiesner et al. |
| 5,350,396 | A | | 9/1994 | Eliachar |
| 5,356,418 | A | | 10/1994 | Shturman |
| 5,368,049 | A | | 11/1994 | Raman et al. |
| 5,368,558 | A | | 11/1994 | Nita |
| 5,368,566 | A | | 11/1994 | Crocker |
| 5,370,640 | A | * | 12/1994 | Kolff ................................ 606/2 |
| 5,372,138 | A | | 12/1994 | Crowley et al. |
| 5,372,584 | A | | 12/1994 | Zink et al. |
| D355,031 | S | | 1/1995 | Yoshikawa |
| 5,386,817 | A | | 2/1995 | Jones |
| 5,391,147 | A | | 2/1995 | Imran et al. |
| 5,391,179 | A | | 2/1995 | Mezzoli |
| 5,402,799 | A | | 4/1995 | Colon et al. |
| 5,409,444 | A | | 4/1995 | Kensey |
| 5,411,475 | A | | 5/1995 | Atala et al. |
| 5,411,476 | A | | 5/1995 | Abrams et al. |
| 5,411,477 | A | | 5/1995 | Saab |
| 5,415,633 | A | | 5/1995 | Lazarus |
| 5,425,370 | A | | 6/1995 | Vilkomerson |
| 5,439,446 | A | | 8/1995 | Barry |
| 5,441,494 | A | | 8/1995 | Ortiz |
| 5,441,497 | A | | 8/1995 | Narciso, Jr. |
| 5,445,646 | A | | 8/1995 | Euteneuer et al. |
| 5,450,853 | A | | 9/1995 | Hastings et al. |
| 5,451,221 | A | | 9/1995 | Cho et al. |
| 5,454,817 | A | | 10/1995 | Katz |
| 5,458,572 | A | | 10/1995 | Campbell et al. |
| 5,459,700 | A | | 10/1995 | Jacobs |
| 5,465,717 | A | | 11/1995 | Imran et al. |
| 5,465,733 | A | | 11/1995 | Hinohara et al. |
| 5,478,565 | A | | 12/1995 | Geria |
| 5,486,181 | A | | 1/1996 | Cohen et al. |
| 5,496,338 | A | | 3/1996 | Miyagi et al. |
| 5,497,783 | A | | 3/1996 | Urick et al. |
| 5,507,301 | A | | 4/1996 | Wasicek et al. |
| 5,507,725 | A | | 4/1996 | Savage et al. |
| 5,507,766 | A | | 4/1996 | Kugo et al. |
| 5,507,795 | A | | 4/1996 | Chiang et al. |
| 5,512,055 | A | | 4/1996 | Domb et al. |
| 5,514,128 | A | | 5/1996 | Hillsman et al. |
| 5,519,532 | A | | 5/1996 | Broome |
| 5,531,676 | A | | 7/1996 | Edwards et al. |
| 5,533,985 | A | | 7/1996 | Wong |
| 5,538,008 | A | | 7/1996 | Crowe |
| 5,546,964 | A | | 8/1996 | Stangerup |
| 5,549,542 | A | | 8/1996 | Kovalcheck |
| 5,558,073 | A | | 9/1996 | Pomeranz et al. |
| 5,558,652 | A | | 9/1996 | Henke |
| 5,562,619 | A | | 10/1996 | Mirarchi et al. |
| 5,568,809 | A | | 10/1996 | Ben-Haim |
| 5,571,086 | A | | 11/1996 | Kaplan et al. |
| 5,578,007 | A | | 11/1996 | Imran |
| 5,578,048 | A | | 11/1996 | Pasqualucci et al. |
| 5,582,575 | A | | 12/1996 | Heckele et al. |
| 5,584,827 | A | | 12/1996 | Korteweg et al. |
| 5,591,194 | A | | 1/1997 | Berthiaume |
| 5,599,284 | A | | 2/1997 | Shea |
| 5,599,304 | A | | 2/1997 | Shaari |
| 5,599,576 | A | | 2/1997 | Opolski |
| 5,601,087 | A | | 2/1997 | Gunderson et al. |
| 5,601,594 | A | | 2/1997 | Best |
| 5,607,386 | A | | 3/1997 | Flam |
| 5,617,870 | A | | 4/1997 | Hastings et al. |

(56) References Cited

U.S. PATENT DOCUMENTS

| | | | |
|---|---|---|---|
| 5,626,374 | A | 5/1997 | Kim |
| 5,633,000 | A | 5/1997 | Grossman et al. |
| 5,634,908 | A | 6/1997 | Loomas |
| 5,638,819 | A | 6/1997 | Manwaring et al. |
| 5,643,251 | A | 7/1997 | Hillsman et al. |
| 5,645,789 | A | 7/1997 | Roucher, Jr. |
| 5,647,361 | A | 7/1997 | Damadian |
| 5,656,030 | A | 8/1997 | Hunjan et al. |
| 5,662,674 | A | 9/1997 | Debbas |
| 5,664,567 | A | 9/1997 | Linder |
| 5,664,580 | A | 9/1997 | Erickson et al. |
| 5,665,052 | A | 9/1997 | Bullard |
| 5,669,388 | A | 9/1997 | Vilkomerson |
| 5,673,707 | A | 10/1997 | Chandrasekaran |
| 5,676,673 | A | 10/1997 | Ferre et al. |
| 5,679,400 | A | 10/1997 | Tuch |
| 5,682,199 | A | 10/1997 | Lankford |
| 5,685,838 | A | 11/1997 | Peters et al. |
| 5,685,847 | A | 11/1997 | Barry |
| 5,690,373 | A | 11/1997 | Luker |
| 5,693,065 | A | 12/1997 | Rains, III |
| 5,694,945 | A | 12/1997 | Ben-Haim |
| 5,697,159 | A | 12/1997 | Linden |
| 5,700,286 | A | 12/1997 | Tartaglia et al. |
| 5,707,376 | A | 1/1998 | Kavteladze et al. |
| 5,707,389 | A | 1/1998 | Louw et al. |
| 5,708,175 | A | 1/1998 | Loyanagi et al. |
| 5,711,315 | A | 1/1998 | Jerusalmy |
| 5,713,839 | A | 2/1998 | Shea |
| 5,713,946 | A | 2/1998 | Ben-Haim |
| 5,718,702 | A | 2/1998 | Edwards |
| 5,720,300 | A | 2/1998 | Fagan et al. |
| 5,722,401 | A | 3/1998 | Pietroski et al. |
| 5,722,984 | A | 3/1998 | Fischell et al. |
| 5,729,129 | A | 3/1998 | Acker |
| 5,730,128 | A | 3/1998 | Pomeranz et al. |
| 5,733,248 | A | 3/1998 | Adams et al. |
| 5,752,513 | A | 5/1998 | Acker et al. |
| 5,762,604 | A | 6/1998 | Kieturakis |
| 5,766,158 | A | 6/1998 | Opolski |
| 5,775,327 | A | 7/1998 | Randolph et al. |
| 5,776,158 | A | 7/1998 | Chou |
| 5,779,699 | A | 7/1998 | Lipson |
| 5,789,391 | A | 8/1998 | Jacobus et al. |
| 5,792,100 | A | 8/1998 | Shantha |
| 5,797,878 | A | 8/1998 | Bleam |
| 5,803,089 | A | 9/1998 | Ferre et al. |
| 5,814,016 | A | 9/1998 | Valley et al. |
| 5,819,723 | A | 10/1998 | Joseph |
| 5,820,568 | A | 10/1998 | Willis |
| 5,824,044 | A | 10/1998 | Quiachon et al. |
| 5,824,048 | A | 10/1998 | Tuch |
| 5,824,173 | A | 10/1998 | Fontirroche et al. |
| 5,827,224 | A | 10/1998 | Shippert |
| 5,830,188 | A | 11/1998 | Abouleish |
| 5,833,608 | A | 11/1998 | Acker |
| 5,833,645 | A | 11/1998 | Lieber et al. |
| 5,833,650 | A | 11/1998 | Imran |
| 5,833,682 | A | 11/1998 | Amplatz et al. |
| 5,836,638 | A | 11/1998 | Slocum |
| 5,836,935 | A | 11/1998 | Ashton et al. |
| 5,837,313 | A | 11/1998 | Ding et al. |
| 5,843,089 | A | 12/1998 | Shatjian et al. |
| 5,843,113 | A | 12/1998 | High |
| 5,846,259 | A | 12/1998 | Berthiaume |
| 5,857,998 | A | 1/1999 | Barry |
| 5,862,693 | A | 1/1999 | Myers et al. |
| 5,865,767 | A | 2/1999 | Frechette et al. |
| 5,872,879 | A | 2/1999 | Hamm |
| 5,873,835 | A | 2/1999 | Hastings |
| 5,879,324 | A | 3/1999 | Von Hoffmann |
| 5,887,467 | A | 3/1999 | Butterweck et al. |
| 5,902,247 | A | 5/1999 | Coe et al. |
| 5,902,333 | A | 5/1999 | Roberts et al. |
| 5,904,701 | A | 5/1999 | Daneshvar |
| 5,908,407 | A | 6/1999 | Frazee et al. |
| 5,916,193 | A | 6/1999 | Stevens et al. |
| 5,928,192 | A | 7/1999 | Maahs |
| 5,931,811 | A | 8/1999 | Haissaguerre et al. |
| 5,931,818 | A | 8/1999 | Werp et al. |
| 5,932,035 | A | 8/1999 | Koger et al. |
| 5,935,061 | A | 8/1999 | Acker et al. |
| 5,941,816 | A | 8/1999 | Barthel et al. |
| D413,629 | S | 9/1999 | Wolff et al. |
| 5,947,988 | A | 9/1999 | Smith |
| 5,949,929 | A | 9/1999 | Hamm |
| 5,954,693 | A | 9/1999 | Barry |
| 5,954,694 | A | 9/1999 | Sunseri |
| 5,957,842 | A | 9/1999 | Littmann et al. |
| 5,968,085 | A | 10/1999 | Morris et al. |
| 5,971,975 | A | 10/1999 | Mills et al. |
| 5,979,290 | A | 11/1999 | Simeone |
| 5,980,503 | A | 11/1999 | Chin |
| 5,980,551 | A | 11/1999 | Summers et al. |
| 5,984,945 | A | 11/1999 | Sirhan |
| 5,985,307 | A | 11/1999 | Hanson et al. |
| 5,997,562 | A | 12/1999 | Zadno-Azizi et al. |
| 6,006,126 | A | 12/1999 | Cosman |
| 6,006,130 | A | 12/1999 | Higo et al. |
| 6,007,516 | A | 12/1999 | Burbank et al. |
| 6,007,991 | A | 12/1999 | Sivaraman et al. |
| 6,010,511 | A | 1/2000 | Murphy |
| 6,013,019 | A | 1/2000 | Fischell et al. |
| 6,015,414 | A | 1/2000 | Werp et al. |
| 6,016,429 | A | 1/2000 | Khafizov et al. |
| 6,016,439 | A | 1/2000 | Acker |
| 6,019,736 | A | 2/2000 | Avellanet et al. |
| 6,019,777 | A | 2/2000 | Mackenzie |
| 6,021,340 | A | 2/2000 | Randolph et al. |
| 6,022,313 | A | 2/2000 | Ginn et al. |
| 6,027,461 | A | 2/2000 | Walker et al. |
| 6,027,478 | A | 2/2000 | Katz |
| 6,039,699 | A | 3/2000 | Viera |
| 6,042,561 | A | 3/2000 | Ash et al. |
| 6,048,299 | A | 4/2000 | von Hoffmann |
| 6,048,358 | A | 4/2000 | Barak |
| 6,053,172 | A | 4/2000 | Hovda et al. |
| 6,056,702 | A | 5/2000 | Lorenzo |
| 6,059,752 | A | 5/2000 | Segal |
| 6,063,079 | A | 5/2000 | Hovda et al. |
| 6,071,233 | A | 6/2000 | Ishikawa et al. |
| 6,079,755 | A | 6/2000 | Chang |
| 6,080,190 | A | 6/2000 | Schwartz |
| 6,083,148 | A | 7/2000 | Williams |
| 6,083,188 | A | 7/2000 | Becker et al. |
| 6,086,585 | A | 7/2000 | Hovda et al. |
| 6,092,846 | A | 7/2000 | Fuss et al. |
| 6,093,150 | A | 7/2000 | Chandler et al. |
| 6,093,195 | A | 7/2000 | Ouchi |
| 6,109,268 | A | 8/2000 | Thapliyal et al. |
| 6,113,567 | A | 9/2000 | Becker |
| 6,117,105 | A | 9/2000 | Bresnaham et al. |
| 6,122,541 | A | 9/2000 | Cosman et al. |
| 6,123,697 | A | 9/2000 | Shippert |
| 6,135,991 | A | 10/2000 | Muni et al. |
| 6,136,006 | A | 10/2000 | Johnson et al. |
| 6,139,510 | A | 10/2000 | Palermo |
| 6,142,957 | A | 11/2000 | Diamond et al. |
| 6,146,415 | A | 11/2000 | Fitz |
| 6,148,823 | A | 11/2000 | Hastings |
| 6,149,213 | A | 11/2000 | Sokurenko et al. |
| 6,159,170 | A | 12/2000 | Borodulin et al. |
| 6,171,298 | B1 | 1/2001 | Matsuura et al. |
| 6,171,303 | B1 | 1/2001 | Ben-Haim |
| 6,174,280 | B1 | 1/2001 | Oneda et al. |
| 6,176,829 | B1 | 1/2001 | Vilkomerson |
| 6,179,788 | B1 | 1/2001 | Sullivan |
| 6,179,811 | B1 | 1/2001 | Fugoso et al. |
| 6,183,433 | B1 | 2/2001 | Bays |
| 6,183,461 | B1 | 2/2001 | Matsuura et al. |
| 6,183,464 | B1 | 2/2001 | Sharp et al. |
| 6,190,353 | B1 | 2/2001 | Makower et al. |
| 6,190,381 | B1 | 2/2001 | Olsen et al. |
| 6,193,650 | B1 | 2/2001 | Ryan, Jr. |

(56) References Cited

U.S. PATENT DOCUMENTS 6,195,225 B1 2/2001 Komatsu et al.
6,200,257 B1 3/2001 Winkler
6,206,870 B1 3/2001 Kanner
6,206,900 B1 3/2001 Tabatabaei et al.
6,213,975 B1 4/2001 Laksin
6,221,042 B1 4/2001 Adams
6,231,543 B1 5/2001 Hegde et al.
6,234,958 B1 5/2001 Snoke et al.
6,238,364 B1 5/2001 Becker
6,238,391 B1 5/2001 Olsen et al.
6,241,519 B1 6/2001 Sedleemayer
6,249,180 B1 6/2001 Maalej et al.
6,254,550 B1 7/2001 McNamara et al.
6,268,574 B1 7/2001 Edens
6,270,477 B1 8/2001 Bagaoisan et al.
6,290,689 B1 9/2001 Delaney et al.
6,293,957 B1 9/2001 Peters et al.
6,295,990 B1 10/2001 Lewis et al.
6,302,875 B1 10/2001 Makower et al.
6,306,105 B1 10/2001 Rooney et al.
6,306,124 B1 10/2001 Jones et al.
D450,382 S 11/2001 Nestenborg
6,322,495 B1 11/2001 Snow et al.
6,328,564 B1 12/2001 Thurow
6,332,089 B1 12/2001 Acker et al.
6,332,891 B1 12/2001 Himes
6,340,360 B1 1/2002 Lyles et al.
6,344,028 B1 2/2002 Barry
6,348,041 B1 2/2002 Klint
6,352,503 B1 3/2002 Matsui et al.
6,364,856 B1 4/2002 Ding et al.
6,375,615 B1 4/2002 Flaherty et al.
6,375,629 B1 4/2002 Muni et al.
6,383,146 B1 5/2002 Klint
6,386,197 B1 5/2002 Miller
6,389,313 B1 5/2002 Marchitto et al.
6,390,993 B1 5/2002 Cornish et al.
6,394,093 B1 5/2002 Lethi
6,398,758 B1 6/2002 Jacobsen et al.
6,409,863 B1 6/2002 Williams et al.
6,419,653 B2 7/2002 Edwards et al.
6,423,012 B1 7/2002 Kato et al.
6,425,877 B1 7/2002 Edwards
6,432,986 B2 8/2002 Levin
6,440,061 B1 8/2002 Wenner et al.
6,443,947 B1 9/2002 Marko et al.
6,445,939 B1 9/2002 Swanson et al.
6,450,975 B1 9/2002 Brennan et al.
6,450,989 B2 9/2002 Dubrul et al.
6,464,650 B2 10/2002 Jafari et al.
6,468,202 B1 10/2002 Irion et al.
6,468,297 B1 10/2002 Williams et al.
6,485,475 B1 11/2002 Chelly
6,488,653 B1 12/2002 Lombardo
6,491,940 B1 12/2002 Levin
6,494,894 B2 12/2002 Mirarchi
6,500,130 B2 12/2002 Kinsella et al.
6,500,189 B1 12/2002 Lang et al.
6,503,087 B1 1/2003 Eggert et al.
6,503,185 B1 1/2003 Waksman et al.
6,503,263 B2 1/2003 Adams
6,511,418 B2 1/2003 Shahidi et al.
6,514,249 B1 2/2003 Maguire et al.
6,517,478 B2 2/2003 Khadem
6,524,129 B2 2/2003 Cote et al.
6,524,299 B1 2/2003 Tran et al.
6,526,302 B2 2/2003 Hassett
6,527,753 B2 3/2003 Sekine et al.
6,529,756 B1 3/2003 Phan et al.
6,533,754 B1 3/2003 Hisamatsu et al.
6,536,437 B1 3/2003 Dragisic
6,537,294 B1 3/2003 Boyle et al.
6,543,452 B1 4/2003 Lavigne
6,544,223 B1 4/2003 Kokish
6,544,230 B1 4/2003 Flaherty et al.
6,549,800 B1 4/2003 Atalar et al.
6,551,239 B2 4/2003 Renner et al.
6,569,146 B1 5/2003 Werner et al.
6,569,147 B1 5/2003 Evans et al.
6,571,131 B1 5/2003 Nguyen
6,572,538 B2 6/2003 Takase
6,572,590 B1 6/2003 Stevens et al.
6,579,285 B2 6/2003 Sinofsky
6,585,639 B1 7/2003 Kotmel et al.
6,585,717 B1 7/2003 Wittenberger et al.
6,585,718 B2 7/2003 Hayzelden et al.
6,585,794 B2 7/2003 Shimoda et al.
6,589,164 B1 7/2003 Flaherty
6,589,237 B2 7/2003 Woloszko et al.
6,591,130 B2 7/2003 Shahidi
6,596,009 B1 7/2003 Jelic
6,607,546 B1 8/2003 Murken
6,610,059 B1 8/2003 West, Jr.
6,612,999 B2 9/2003 Brennan et al.
6,613,066 B1 9/2003 Fukaya et al.
6,616,601 B2 9/2003 Hayakawa
6,616,659 B1 9/2003 de la Torre et al.
6,616,678 B2 9/2003 Nishtala et al.
6,616,913 B1 9/2003 Mautone
6,619,085 B1 9/2003 Hsieh
6,634,684 B2 10/2003 Spiessl
6,638,233 B2 10/2003 Corvi et al.
6,638,268 B2 10/2003 Niazi
6,638,291 B1 10/2003 Ferrera et al.
6,645,193 B2 11/2003 Mangosong
6,652,472 B2 11/2003 Jafari et al.
6,652,480 B1 11/2003 Imran et al.
6,656,166 B2 12/2003 Lurie et al.
6,659,106 B1 12/2003 Hovda et al.
6,663,589 B1 12/2003 Halevy
6,669,689 B2 12/2003 Lehmann et al.
6,669,711 B1 12/2003 Noda
6,672,773 B1 1/2004 Glenn et al.
6,673,025 B1 1/2004 Richardson et al.
6,679,871 B2 1/2004 Hahnen
6,685,648 B2 2/2004 Flaherty et al.
6,689,096 B1 2/2004 Loubens et al.
6,689,146 B1 2/2004 Himes
6,702,735 B2 3/2004 Kelly
6,712,757 B2 3/2004 Becker et al.
6,714,809 B2 3/2004 Lee et al.
6,716,183 B2 4/2004 Clayman et al.
6,716,216 B1 4/2004 Boucher et al.
6,716,813 B2 4/2004 Lim et al.
6,719,749 B1 4/2004 Schweikert et al.
6,719,763 B2 4/2004 Chung et al.
6,726,701 B2 4/2004 Gilson et al.
6,738,656 B1 5/2004 Ferre et al.
6,755,812 B2 6/2004 Peterson et al.
6,776,772 B1 8/2004 de Vrijer et al.
6,780,168 B2 8/2004 Jellie
6,783,522 B2 8/2004 Fischell
6,783,536 B2 8/2004 Vilsmeier et al.
6,786,864 B2 9/2004 Matsuura et al.
6,796,960 B2 9/2004 Cioanta et al.
6,811,544 B2 11/2004 Schaer
6,817,364 B2 11/2004 Garibaldi et al.
6,817,976 B2 11/2004 Rovegno
6,827,683 B2 12/2004 Otawara
6,827,701 B2 12/2004 MacMahon et al.
6,832,715 B2 12/2004 Eungard et al.
D501,677 S 2/2005 Becker
6,851,290 B1 2/2005 Meier et al.
6,855,136 B2 2/2005 Dorros et al.
6,860,264 B2 3/2005 Christopher
6,860,849 B2 3/2005 Matsushita et al.
6,878,106 B1 4/2005 Herrmann
6,890,329 B2 5/2005 Carroll et al.
6,899,672 B2 5/2005 Chin et al.
6,902,556 B2 6/2005 Grimes et al.
6,913,763 B2 7/2005 Lerner
6,927,478 B2 8/2005 Paek
6,939,361 B1 9/2005 Kleshinski
6,939,374 B2 9/2005 Banik et al.

(56) References Cited

U.S. PATENT DOCUMENTS

| | | | |
|---|---|---|---|
| 6,955,657 | B1 | 10/2005 | Webler |
| 6,966,906 | B2 | 11/2005 | Brown |
| 6,971,998 | B2 | 12/2005 | Rosenman et al. |
| 6,979,290 | B2 | 12/2005 | Mourlas et al. |
| 6,984,203 | B2 | 1/2006 | Tartaglia et al. |
| 6,991,597 | B2 | 1/2006 | Gellman et al. |
| 6,997,931 | B2 | 2/2006 | Sauer et al. |
| 6,997,941 | B2 | 2/2006 | Sharkey et al. |
| 7,004,173 | B2 | 2/2006 | Sparks et al. |
| 7,004,176 | B2 | 2/2006 | Lau |
| 7,008,412 | B2 | 3/2006 | Maginot |
| 7,011,654 | B2 | 3/2006 | Dubrul et al. |
| 7,022,105 | B1 | 4/2006 | Edwards |
| 7,043,961 | B2 | 5/2006 | Pandey |
| 7,044,964 | B2 | 5/2006 | Jang et al. |
| 7,052,474 | B2 | 5/2006 | Castell et al. |
| 7,056,284 | B2 | 6/2006 | Martone et al. |
| 7,056,303 | B2 | 6/2006 | Dennis et al. |
| 7,074,197 | B2 | 7/2006 | Reynolds et al. |
| 7,074,426 | B2 | 7/2006 | Kochinke |
| 7,097,612 | B2 | 8/2006 | Bertolero et al. |
| 7,108,677 | B2 | 9/2006 | Courtney et al. |
| 7,108,706 | B2 | 9/2006 | Hogle |
| 7,128,718 | B2 | 10/2006 | Hojeibane et al. |
| 7,131,969 | B1 | 11/2006 | Hovda et al. |
| 7,140,480 | B2 | 11/2006 | Drussel et al. |
| D534,216 | S | 12/2006 | Makower et al. |
| 7,160,255 | B2 | 1/2007 | Saadat |
| 7,169,140 | B1 | 1/2007 | Kume |
| 7,169,163 | B2 | 1/2007 | Becker |
| 7,172,562 | B2 | 2/2007 | McKinley |
| 7,174,774 | B2 | 2/2007 | Pawar et al. |
| 7,182,735 | B2 | 2/2007 | Shireman et al. |
| 7,184,827 | B1 | 2/2007 | Edwards |
| 7,207,981 | B2 | 4/2007 | Quinn et al. |
| 7,214,201 | B2 | 5/2007 | Burmeister et al. |
| 7,233,820 | B2 | 6/2007 | Gilboa |
| 7,235,099 | B1 | 6/2007 | Duncavage et al. |
| 7,237,313 | B2 | 7/2007 | Skujins et al. |
| 7,252,677 | B2 | 8/2007 | Burwell et al. |
| 7,282,057 | B2 | 10/2007 | Surti et al. |
| 7,292,885 | B2 | 11/2007 | Scott et al. |
| 7,294,345 | B2 | 11/2007 | Haapakumpu et al. |
| 7,294,365 | B2 | 11/2007 | Hayakawa et al. |
| 7,303,533 | B2 | 12/2007 | Johansen et al. |
| 7,313,430 | B2 | 12/2007 | Urquhart et al. |
| 7,316,168 | B2 | 1/2008 | van der Knokke et al. |
| 7,316,656 | B2 | 1/2008 | Shireman et al. |
| 7,318,831 | B2 | 1/2008 | Alvarez et al. |
| 7,322,934 | B2 | 1/2008 | Miyake et al. |
| 7,326,235 | B2 | 2/2008 | Edwards |
| 7,338,467 | B2 | 3/2008 | Lutter |
| 7,343,920 | B2 | 3/2008 | Toby et al. |
| 7,347,868 | B2 | 3/2008 | Burnett et al. |
| 7,359,755 | B2 | 4/2008 | Jones et al. |
| 7,361,168 | B2 | 4/2008 | Makower et al. |
| 7,366,562 | B2 | 4/2008 | Dukesherer |
| 7,371,210 | B2 | 5/2008 | Brock et al. |
| 7,381,205 | B2 | 6/2008 | Thommen |
| 7,410,480 | B2 | 8/2008 | Muni et al. |
| 7,419,497 | B2 | 9/2008 | Muni et al. |
| 7,438,701 | B2 | 10/2008 | Theeuwes et al. |
| 7,442,191 | B2 | 10/2008 | Hovda et al. |
| 7,452,351 | B2 | 11/2008 | Miller et al. |
| 7,454,244 | B2 | 11/2008 | Kassab et al. |
| 7,462,175 | B2 | 12/2008 | Chang et al. |
| 7,471,994 | B2 | 12/2008 | Ford et al. |
| 7,481,218 | B2 | 1/2009 | Djupesland |
| 7,481,800 | B2 | 1/2009 | Jacques |
| D586,465 | S | 2/2009 | Faulkner et al. |
| D586,916 | S | 2/2009 | Faulkner et al. |
| 7,488,313 | B2 | 2/2009 | Segal et al. |
| 7,488,337 | B2 | 2/2009 | Saab et al. |
| 7,493,156 | B2 | 2/2009 | Manning et al. |
| 7,500,971 | B2 | 3/2009 | Chang et al. |
| D590,502 | S | 4/2009 | Geisser et al. |
| 7,520,876 | B2 | 4/2009 | Ressemann et al. |
| 7,532,920 | B1 | 5/2009 | Ainsworth et al. |
| 7,544,192 | B2 | 6/2009 | Eaton et al. |
| 7,559,925 | B2 | 7/2009 | Goldfarb et al. |
| 7,610,104 | B2 | 10/2009 | Kaplan et al. |
| 7,615,005 | B2 | 11/2009 | Stefanchik et al. |
| 7,618,450 | B2 | 11/2009 | Zarowski et al. |
| 7,625,335 | B2 | 12/2009 | Deichmann et al. |
| 7,632,291 | B2 | 12/2009 | Stephens et al. |
| 7,634,233 | B2 | 12/2009 | Deng et al. |
| 7,641,644 | B2 | 1/2010 | Chang et al. |
| 7,641,668 | B2 | 1/2010 | Perry et al. |
| 7,645,272 | B2 | 1/2010 | Chang et al. |
| 7,648,367 | B1 | 1/2010 | Makower et al. |
| 7,654,997 | B2 | 2/2010 | Makower et al. |
| 7,680,244 | B2 | 3/2010 | Gertner et al. |
| 7,686,798 | B2 | 3/2010 | Eaton et al. |
| 7,691,120 | B2 | 4/2010 | Shluzas et al. |
| 7,717,933 | B2 | 5/2010 | Becker |
| 7,720,521 | B2 | 5/2010 | Chang et al. |
| 7,727,186 | B2 | 6/2010 | Makower et al. |
| 7,727,226 | B2 | 6/2010 | Chang et al. |
| 7,736,301 | B1 | 6/2010 | Webler et al. |
| 7,740,642 | B2 | 6/2010 | Becker |
| 7,753,929 | B2 | 7/2010 | Becker |
| 7,753,930 | B2 | 7/2010 | Becker |
| 7,771,409 | B2 | 8/2010 | Chang et al. |
| 7,775,968 | B2 | 8/2010 | Mathis |
| 7,785,315 | B1 | 8/2010 | Muni et al. |
| 7,799,048 | B2 | 9/2010 | Hudson et al. |
| 7,799,337 | B2 | 9/2010 | Levin |
| 7,803,150 | B2 | 9/2010 | Chang et al. |
| 7,833,282 | B2 | 11/2010 | Mandpe |
| 7,837,672 | B2 | 11/2010 | Intoccia |
| 7,840,254 | B2 | 11/2010 | Glossop |
| 7,854,744 | B2 | 12/2010 | Becker |
| D630,321 | S | 1/2011 | Hamilton, Jr. |
| 7,875,050 | B2 | 1/2011 | Samson et al. |
| D632,791 | S | 2/2011 | Murner |
| 7,881,769 | B2 | 2/2011 | Sobe |
| 7,883,717 | B2 | 2/2011 | Varner et al. |
| 7,896,891 | B2 | 3/2011 | Catanese, III et al. |
| 7,951,132 | B2 | 5/2011 | Eaton et al. |
| 7,988,705 | B2 | 8/2011 | Galdonik et al. |
| 7,993,353 | B2 | 8/2011 | Roβner et al. |
| 8,002,740 | B2 | 8/2011 | Willink et al. |
| 8,014,849 | B2 | 9/2011 | Peckham |
| 8,016,752 | B2 | 9/2011 | Armstrong et al. |
| 8,025,635 | B2 | 9/2011 | Eaton et al. |
| 8,080,000 | B2 | 12/2011 | Makower et al. |
| 8,088,063 | B2 | 1/2012 | Fujikura et al. |
| 8,088,101 | B2 | 1/2012 | Chang et al. |
| 8,090,433 | B2 | 1/2012 | Makower et al. |
| 8,100,933 | B2 | 1/2012 | Becker |
| 8,104,483 | B2 | 1/2012 | Taylor |
| 8,114,062 | B2 | 2/2012 | Muni et al. |
| 8,114,113 | B2 | 2/2012 | Becker |
| 8,123,722 | B2 | 2/2012 | Chang et al. |
| 8,142,422 | B2 | 3/2012 | Makower et al. |
| 8,146,400 | B2 | 4/2012 | Goldfarb et al. |
| 8,147,545 | B2 | 4/2012 | Avior |
| 8,167,821 | B2 | 5/2012 | Sharrow |
| 8,172,828 | B2 | 5/2012 | Chang et al. |
| 8,190,389 | B2 | 5/2012 | Kim et al. |
| 8,197,433 | B2 | 6/2012 | Cohen |
| 8,197,552 | B2 | 6/2012 | Mandpe |
| 8,249,700 | B2 | 8/2012 | Clifford et al. |
| 8,277,386 | B2 | 10/2012 | Ahmed et al. |
| 8,317,816 | B2 | 11/2012 | Becker |
| 8,337,454 | B2 | 12/2012 | Eaton et al. |
| 8,388,642 | B2 | 3/2013 | Muni et al. |
| 8,403,954 | B2 | 3/2013 | Santin et al. |
| 8,414,473 | B2 | 4/2013 | Jenkins et al. |
| 8,425,457 | B2 | 4/2013 | John et al. |
| 8,439,687 | B1 | 5/2013 | Morriss et al. |
| 8,535,707 | B2 | 9/2013 | Arensdorf et al. |
| 2001/0004644 | A1 | 6/2001 | Levin |
| 2001/0005785 | A1 | 6/2001 | Sachse |

(56) References Cited

U.S. PATENT DOCUMENTS

| | | | |
|---|---|---|---|
| 2001/0034530 | A1 | 10/2001 | Malackowski et al. |
| 2002/0006961 | A1 | 1/2002 | Katz et al. |
| 2002/0055746 | A1 | 5/2002 | Burke et al. |
| 2002/0077593 | A1 | 6/2002 | Perkins et al. |
| 2002/0090388 | A1 | 7/2002 | Humes et al. |
| 2003/0013985 | A1 | 1/2003 | Saadat |
| 2003/0017111 | A1 | 1/2003 | Rabito |
| 2003/0018291 | A1 | 1/2003 | Hill et al. |
| 2003/0040697 | A1 | 2/2003 | Pass et al. |
| 2003/0073900 | A1 | 4/2003 | Senarith et al. |
| 2003/0083608 | A1 | 5/2003 | Evans et al. |
| 2003/0114732 | A1 | 6/2003 | Webler et al. |
| 2003/0163154 | A1 | 8/2003 | Miyata et al. |
| 2003/0220551 | A1 | 11/2003 | Kimball et al. |
| 2004/0015150 | A1 | 1/2004 | Zadno-Azizi |
| 2004/0018980 | A1 | 1/2004 | Gurney et al. |
| 2004/0020492 | A1 | 2/2004 | Dubrul et al. |
| 2004/0034311 | A1 | 2/2004 | Mihakcik |
| 2004/0043052 | A1 | 3/2004 | Hunter et al. |
| 2004/0058992 | A1 | 3/2004 | Marinello et al. |
| 2004/0064105 | A1 | 4/2004 | Capes et al. |
| 2004/0116958 | A1 | 6/2004 | Gopferich et al. |
| 2004/0127820 | A1 | 7/2004 | Clayman et al. |
| 2004/0158229 | A1 | 8/2004 | Quinn |
| 2004/0181175 | A1 | 9/2004 | Clayman et al. |
| 2004/0193073 | A1 | 9/2004 | DeMello et al. |
| 2004/0220516 | A1 | 11/2004 | Solomon et al. |
| 2004/0230156 | A1 | 11/2004 | Schreck et al. |
| 2004/0236231 | A1 | 11/2004 | Knighton et al. |
| 2004/0249243 | A1 | 12/2004 | Kleiner |
| 2004/0267347 | A1 | 12/2004 | Cervantes |
| 2005/0027249 | A1 | 2/2005 | Reifart et al. |
| 2005/0055077 | A1 | 3/2005 | Marco |
| 2005/0059930 | A1 | 3/2005 | Garrison et al. |
| 2005/0059931 | A1 | 3/2005 | Garrison et al. |
| 2005/0089670 | A1 | 4/2005 | Large |
| 2005/0107738 | A1 | 5/2005 | Slater et al. |
| 2005/0113687 | A1 | 5/2005 | Herweck et al. |
| 2005/0113850 | A1 | 5/2005 | Tagge |
| 2005/0119590 | A1 | 6/2005 | Burmeister et al. |
| 2005/0131316 | A1 | 6/2005 | Flagle et al. |
| 2005/0143687 | A1 | 6/2005 | Rosenblatt et al. |
| 2005/0182319 | A1 | 8/2005 | Glossop |
| 2005/0234507 | A1 | 10/2005 | Geske et al. |
| 2005/0244472 | A1 | 11/2005 | Hughes et al. |
| 2005/0283221 | A1 | 12/2005 | Mann et al. |
| 2006/0004323 | A1 | 1/2006 | Chang et al. |
| 2006/0047261 | A1 | 3/2006 | Joshi |
| 2006/0063973 | A1 | 3/2006 | Makower et al. |
| 2006/0173382 | A1 | 8/2006 | Schreiner |
| 2006/0189844 | A1 * | 8/2006 | Tien .............................. 600/143 |
| 2006/0190022 | A1 | 8/2006 | Beyar et al. |
| 2006/0211752 | A1 | 9/2006 | Kohn et al. |
| 2006/0271024 | A1 | 11/2006 | Gertner et al. |
| 2006/0284428 | A1 | 12/2006 | Beadle et al. |
| 2007/0020196 | A1 | 1/2007 | Pipkin et al. |
| 2007/0112358 | A1 | 5/2007 | Abbott |
| 2007/0129751 | A1 | 6/2007 | Muni et al. |
| 2007/0135789 | A1 | 6/2007 | Chang et al. |
| 2007/0167682 | A1 | 7/2007 | Goldfarb et al. |
| 2007/0207186 | A1 | 9/2007 | Scanlon et al. |
| 2007/0208252 | A1 | 9/2007 | Makower |
| 2007/0208301 | A1 | 9/2007 | Evard et al. |
| 2007/0249896 | A1 | 10/2007 | Goldfarb et al. |
| 2007/0269385 | A1 | 11/2007 | Yun et al. |
| 2007/0282305 | A1 | 12/2007 | Goldfarb et al. |
| 2007/0293727 | A1 | 12/2007 | Goldfarb et al. |
| 2007/0293946 | A1 | 12/2007 | Gonzales et al. |
| 2008/0015544 | A1 | 1/2008 | Keith et al. |
| 2008/0033519 | A1 | 2/2008 | Burwell et al. |
| 2008/0051804 | A1 | 2/2008 | Cottler et al. |
| 2008/0097516 | A1 | 4/2008 | Chang et al. |
| 2008/0103521 | A1 | 5/2008 | Makower et al. |
| 2008/0119693 | A1 | 5/2008 | Makower et al. |
| 2008/0125626 | A1 | 5/2008 | Chang et al. |
| 2008/0132938 | A1 | 6/2008 | Chang et al. |
| 2008/0172033 | A1 | 7/2008 | Keith et al. |
| 2008/0183128 | A1 | 7/2008 | Morriss et al. |
| 2008/0188803 | A1 | 8/2008 | Jang |
| 2008/0188870 | A1 | 8/2008 | Andre et al. |
| 2008/0195041 | A1 | 8/2008 | Goldfarb et al. |
| 2008/0228085 | A1 | 9/2008 | Jenkins et al. |
| 2008/0262508 | A1 | 10/2008 | Clifford et al. |
| 2008/0275483 | A1 | 11/2008 | Makower et al. |
| 2008/0281156 | A1 | 11/2008 | Makower et al. |
| 2008/0287908 | A1 | 11/2008 | Muni et al. |
| 2008/0319424 | A1 | 12/2008 | Muni et al. |
| 2009/0030274 | A1 | 1/2009 | Goldfarb et al. |
| 2009/0088728 | A1 | 4/2009 | Dollar et al. |
| 2009/0156980 | A1 | 6/2009 | Eaton et al. |
| 2009/0163890 | A1 | 6/2009 | Clifford et al. |
| 2009/0187089 | A1 | 7/2009 | Say et al. |
| 2009/0187098 | A1 | 7/2009 | Makower et al. |
| 2009/0198216 | A1 | 8/2009 | Muni et al. |
| 2009/0240112 | A1 | 9/2009 | Goldfarb et al. |
| 2009/0240237 | A1 | 9/2009 | Goldfarb et al. |
| 2009/0312745 | A1 | 12/2009 | Goldfarb et al. |
| 2010/0030031 | A1 | 2/2010 | Goldfarb et al. |
| 2010/0042046 | A1 | 2/2010 | Chang et al. |
| 2010/0087811 | A1 | 4/2010 | Herrin et al. |
| 2010/0114066 | A1 | 5/2010 | Makower et al. |
| 2010/0174138 | A1 | 7/2010 | Chang et al. |
| 2010/0174308 | A1 | 7/2010 | Chang et al. |
| 2010/0198191 | A1 | 8/2010 | Clifford et al. |
| 2010/0198247 | A1 | 8/2010 | Chang et al. |
| 2010/0198302 | A1 | 8/2010 | Shalev |
| 2010/0210901 | A1 | 8/2010 | Makower et al. |
| 2010/0268245 | A1 | 10/2010 | Chang et al. |
| 2010/0274188 | A1 | 10/2010 | Chang et al. |
| 2010/0290244 | A1 | 11/2010 | Nath |
| 2010/0298862 | A1 | 11/2010 | Chang et al. |
| 2011/0004057 | A1 | 1/2011 | Goldfarb et al. |
| 2011/0015482 | A1 | 1/2011 | Carrillo, Jr. |
| 2011/0060214 | A1 | 3/2011 | Makower |
| 2011/0112512 | A1 | 5/2011 | Muni et al. |
| 2011/0166190 | A1 | 7/2011 | Anderson et al. |
| 2012/0071710 | A1 | 3/2012 | Gazdzinski |
| 2012/0071824 | A1 | 3/2012 | Chang et al. |
| 2012/0136207 | A1 | 5/2012 | Goldfarb et al. |
| 2012/0184983 | A1 | 7/2012 | Chang et al. |
| 2012/0245419 | A1 | 9/2012 | Makower et al. |
| 2012/0265094 | A1 | 10/2012 | Goldfarb et al. |
| 2013/0231529 | A1 | 9/2013 | Chang et al. |
| 2013/0245608 | A1 | 9/2013 | Muni et al. |
| 2013/0261388 | A1 | 10/2013 | Jenkins et al. |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1166710 | 1/2002 |

(56) References Cited

FOREIGN PATENT DOCUMENTS

| | | | |
|---|---|---|---|
| EP | 1413258 | | 4/2004 |
| EP | 1944053 | | 7/2008 |
| FR | 2859377 | | 3/2005 |
| FR | 2916144 | | 11/2008 |
| GB | 2125874 | | 3/1984 |
| GB | 2305174 | | 4/1997 |
| JP | 53-67935 | | 6/1978 |
| JP | 10-24098 | | 1/1989 |
| JP | 3-503011 | | 7/1991 |
| JP | 3-504935 | | 10/1991 |
| JP | 4-221313 | | 8/1992 |
| JP | 4-224766 | | 8/1992 |
| JP | 5-503650 | | 6/1993 |
| JP | 5-211985 | | 8/1993 |
| JP | 6-277296 | | 10/1994 |
| JP | 7-327916 | | 12/1995 |
| JP | 8-317989 | | 12/1996 |
| JP | 11-507251 | | 6/1999 |
| JP | 2000-501634 | | 2/2000 |
| JP | 2001-501846 | | 2/2001 |
| JP | 2001-095815 | | 4/2001 |
| JP | 2001-526077 | | 12/2001 |
| JP | 2002-028166 | | 1/2002 |
| JP | 2002-508214 | | 3/2002 |
| JP | 2002-537908 | | 11/2002 |
| JP | 2002-538850 | | 11/2002 |
| JP | 2003-507140 | | 2/2003 |
| JP | 2003-062080 | | 3/2003 |
| JP | 2003-521327 | | 7/2003 |
| JP | 2004-357728 | | 12/2004 |
| JP | 2005-532869 | | 11/2005 |
| RU | 2213530 | | 10/2003 |
| SU | 1662571 | | 7/1991 |
| WO | WO 90/11053 | | 10/1990 |
| WO | WO 90/14865 | | 12/1990 |
| WO | WO 91/17787 | | 11/1991 |
| WO | WO 92/15286 | | 9/1992 |
| WO | WO 92/22350 | | 12/1992 |
| WO | WO 94/12095 | | 6/1994 |
| WO | WO 94/21320 | | 9/1994 |
| WO | WO 95/02430 | | 1/1995 |
| WO | WO 96/29071 | | 9/1996 |
| WO | WO 97/21461 | | 6/1997 |
| WO | WO 98/55174 | | 12/1998 |
| WO | WO 99/00064 | | 1/1999 |
| WO | WO 99/24106 | | 5/1999 |
| WO | WO 99/26692 | | 6/1999 |
| WO | WO 99/30655 | | 6/1999 |
| WO | WO 99/32041 | | 7/1999 |
| WO | WO 99/59649 | | 11/1999 |
| WO | WO 00/09190 | | 2/2000 |
| WO | WO 00/09192 | | 2/2000 |
| WO | WO 00/23009 | | 4/2000 |
| WO | WO 00/51672 | | 9/2000 |
| WO | WO 00/53252 | | 9/2000 |
| WO | WO 01/05462 | | 1/2001 |
| WO | WO 01/45572 | | 6/2001 |
| WO | WO 01/54558 | | 8/2001 |
| WO | WO 01/56481 | | 8/2001 |
| WO | WO 01/70325 | | 9/2001 |
| WO | WO 01/74266 | | 10/2001 |
| WO | WO 01/97895 | | 12/2001 |
| WO | WO 02/062269 | | 8/2002 |
| WO | WO 02/089899 | | 11/2002 |
| WO | WO 03/049603 | | 6/2003 |
| WO | WO 03/063703 | | 8/2003 |
| WO | WO 03/105657 | | 12/2003 |
| WO | WO 2004/006788 | | 1/2004 |
| WO | WO 2004/018980 | | 3/2004 |
| WO | WO 2004/026391 | | 4/2004 |
| WO | WO 2004/082525 | A2 | 9/2004 |
| WO | WO 2004/082525 | A3 | 9/2004 |
| WO | WO 2005/018730 | | 3/2005 |
| WO | WO 2005/077450 | | 8/2005 |
| WO | WO 2005/089670 | | 9/2005 |
| WO | WO 2005/117755 | | 12/2005 |
| WO | WO 2006/034008 | | 3/2006 |
| WO | WO 2006/078884 | | 7/2006 |
| WO | WO 2006/107957 | | 10/2006 |
| WO | WO 2006/116597 | | 11/2006 |
| WO | WO 2006/118737 | | 11/2006 |
| WO | WO 2006/135853 | | 12/2006 |
| WO | WO 2007/035204 | | 3/2007 |
| WO | WO 2007/111636 | | 10/2007 |
| WO | WO 2007/124260 | | 11/2007 |
| WO | WO 2008/036149 | | 3/2008 |
| WO | WO 2008/045242 | | 4/2008 |
| WO | WO 2008/051918 | | 5/2008 |
| WO | WO 2008/134382 | | 11/2008 |

OTHER PUBLICATIONS

Bellis, M. History of the Catheter—Balloon Catheter—Thomas Fogarty. Www.inventors.about.com/library/inventors/blcatheter.htm?p=1.

Benninger et al.; Adult Chronic Rhinosinusitis: Definitions, Diagnosis, Epidemiology, and Pathophysilogy Arch Otolarygol Head and Neck Surg. vol. 129 (Sep. 2003) pp. A1-S32.

Bent et al. 'The Frontal Cell as a Cause of Frontal Sinus Obstruction' American Journal of Rhinology, vol. 8, No. 4 (1994) pp. 185-191.

Binner et al. 'Fibre-Optic Transillunination of the Sinuses: A Comparison of the Value of Radiography and Transillumination in Antral Disease' Clinical Otolaryngology. vol. 3 (1978) pp. 1-11.

Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

Casiano et al. 'Endoscopic Lothrop Procedure: the University of Miami Experience' American Journal of Rhinology, vol. 12, No. 5 (1998) pp. 335-339.

Casserly, I.P. et al., Chapter 7. 'Guides and Wires in Percutaneous Coronary Intervention' Strategic Approaches in Coronary Intervention (2006) Lippincott Williams & Wilkins pp. 91-99.

Chien, Y.W. et al. 'Nasal Systemic Drug Delivery' Drugs and Pharmaceutical Sciences, vol. 39, pp. 60-63.

Cohen et al. 'Endoscopic Sinus Surgery: Where we are and where we're going' Current Opinion in Otolaryngology & Head and Neck Surgery, vol. 13 (2005) pp. 32-38.

Colla, A. et al., 'Trihaloacetylated Enol Ethers—General Synthetic Procedure and Heterocyclic Ring Closure Reactions with Hydroxylamine' Synthesis, (Jun. 1991) pp. 483-486.

Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.

Cussler, E.L. 'Diffusion: Mass transfer in Fluid Systems' Cambridge University Press (1996).

Davis, G.E. et al. 'A Complication from Neurocranial Restructuring' Arch Orolaryngol Head Neck Surg. vol. 129 (Apr. 2003) pp. 472-474.

Deutschmann, R. et al. 'A Contribution to the Topical Treatment of [Maxillary] Sinusitis Preliminary Communication' Stomat DDR 26, (1976) pp. 585-592.

Domb, A. et al. 'Handbook of Biodegradable Polymers' Harwood Academic Publishers (1997).

Doyle Nasal Splints, Jan. 27, 2007; www.doylemedical.com/nasalsplints.htm.

Draf, W. 'Endonasal Micro-Endoscopic Frontal Sinus Surgery: the Fulda Concept' Op Tech Otolaryngol Head Neck Surg. vol. 2 (1991) pp. 234-240.

Edmond, C. et al. 'ENT Surgical Stimulator' Nov. 1989.

ENT Checklist; Physical Examination Performance Checklist [date of publication unknown].

Eremychev, V.A. 'Needles for Puncture and Drainage of the Maxillary Sinus' Meditsinskaya Tekhnika, No. 5 (1974) pp. 54.55.

Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.

(56) References Cited

OTHER PUBLICATIONS

Ford, C.N. ‘A Multipurpose Laryngeal Injector Device’ Otolaryngol. Head Neck Surg. (1990) vol. 103, No. 1 pp. 135-137.
Friedman, M., M.D., et al. ‘Frontal Sinus Surgery: Endoscopic Technique’ Operative Techniques in Otolarynology—Head and Neck Surgery. vol. 12, No. 2 (Jun. 2001) pp. 60-65.
Friedman, et al. ‘Intraoperative and Postoperative Assessment of Frontal Sinus Patency by Transillumination’ Laryngoscope. vol. 110 (Apr. 2000) pp. 683-684.
Friedman, et al ‘Middle Turbinate Medialization and Preservation in Endoscopic Surgery’ Otolaryngology—Head and Neck Surgery. (2000) vol. 123, No. 1, part 1, pp. 76-80.
Fung, M.K.T. ‘Template for Frontal Osteoplastic Flap’ Laryngoscope. vol. 96 (1986) pp. 578-579.
Gatot, A. et al. ‘Early treatment of Orbital Floor Fractures with Catheter Balloon in Children’ Int J. Pediatric Otorhinolaryngol (1991) vol. 21 pp. 97-101.
Gerus, I.I. et al. ‘β-Ethoxyvinyl Polyfluroroalkyl Ketones—Versatile Synthones in Fluoroorganic Chemistry’ Journal of Fluorine Chemistry. vol. 69 (1994) pp. 195-198. Elesvier Science S.A.
Good, R.H. ‘An Intranasal Method for Opening the Frontal Sinus Establishing the Largest Possible Drainage’ Laryngoscope. vol. 18 (1908) pp. 266-274.
Gopferich ‘Polymer Degradation and Erosion: Mechanisms and Application’ Eur. J. Parm. Biophar. vol. 42 (1996) pp. 1-11.
Gorlov, D.V. et al ‘Acylation of 2-Methoxypropene with Anhydrides and Halides of Perflurocarboxylic Acids in the Presence ot Teriary Amines’ Russian Chemical Bulletin. vol. 48 No. 9 (Sep. 1999) pp. 1791-1792. Kluwer Academic/Plenum Publishers.
Gottmann, et al. ‘Balloon Dilatation in the Nasal Cavity and Paranasal Sinuses’ CIRSE. (Sep. 25, 2004) pp. 1-27.
Gottmann, et al. ‘Balloon Dilatation of Recurrent Ostial Occlusion of the Frontal Sinus’ CIRSE Abstract (Mar. 2001) B-04353.
Gottman, et al., Balloon Dilatation of Recurrent Ostial Occlusion of the Front Sinus OASIS—Online Abstract Submission and Invitation System, 1996-2006, Coe Truman Technologies, Inc.
Gottmann, et al. ‘Successful Treatment of Recurrent Post-Operative Frontal Sinus Stenoses by Balloon Dilatation’ CIRSE. (Oct. 5, 2002).
Gottmann, D. ‘Treatment of Stenoses of Upper Air Routes by Balloon Dilation’ Proceeding of the 83rd Annual Convention of Association of West German ENT Physicians (1999).
Gupta, D. et al., ‘Dacrystitis Secondary to an Iatrogenic Foreign Body in the Lacrimal Apparatus’ Ear, Nose & Throat Journal (2009) www.findarticles.com/p/articles/mi_m0BUM/is_7_88/ai_n32428620/.
Hashim, et al. ‘Balloon Compression of the Intermaxillary Sinus for Intractable Post Traumatic Bleeding from the Maxillary Artery’ Scandinavian Journal of Plastic and reconstruction Sergery and Hand Surgery (1999) vol. 33 pp. 321-324.
Hojo, M. et al, ‘Electrophilic Substitutions of Olefinic Hydrogens II. Acylation of Vinyle Ethers and N Vinyl Amides Chemistry Letters’ (1976) pp. 499-502. Chemical Society of Japan.
Hopf, J.U.G. et al. ‘Minature Endoscopes in Otorhinolaryngologic Applications’ Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. ‘Endonasal Frontal Sinusotomy in Surgical Management of Chronic Sinusitis: A Critical Evaluation’ American Journal of Rhinology. vol. 11, No. 1 (1997) pp. 1-9.
Hosemann, M.E. et al. ‘Experimentelle Untersuchungen sur Wundheilung in den Nasennebenholhlen. II. Spontaner Wundschluss und medikamentose Effekte im standardisierten Wundmodell.’ HNO 39 (1991) pp. 48-54. ‘Experimental investigations on wound healing of the paranasal sinuses. II. Spontaneous wound closure and pharmacological effects in a standardized animal model.’ HNO 39 (1991) pp. 48-54.
Hosemann, W.G. et al. ‘Minimally Invasive Endonasal Sinus Surgery’ Thieme, Stuttgart, New York (2000).
Hosemann, M.E. et al. ‘Normal Wound Healing of the Paranasal Sinuses—Clinical and Experimental Investigations’ Eur Arch Otorhinolarygol. vol. 248, (1991) pp. 390-394.
Hosemann, W. et al. ‘Behandlung nach Nasennebenhohleneingriffen, part 2: Theapeutische Maβnahem’ HNO akutell 7 (1999) pp. 291-302.
Hospital Corpsman Sickcall Screener’s Handbook. Naval Hospital Great Lakes (Apr. 1999) www.brooksidepress.org/Products/Operationa.Medicine/DATA. 2001 pp. 1-6.
Hybels, R.L. ‘Transillumination Durning Osteoplastic Frontal Sinusotomy’ The Laryngoscope. vol. 91 (Sep. 1981) pp. 1560.
Ijaduola, T.G.A. ‘Use of a Foley Catheter for Short-Term Drainage in Frontal Sinus Surgery’ Ther Journal of Laryngology and Otology. (1989) vol. 103, pp. 375.378.
Ingals, E.F. ‘New Operation and Instruments for Draining the Frontal Sinus’ Ann. Otol. Rhinol. Layyngol. vol. 14 (1905) pp. 644-649.
Iro, H. et al., ‘A New Device for Frontal Sinus Endoscopy: First Clinical Report’ Otolaryngol. Head Neck Surg. (2001) vol. 125 No. 6 pp. 613-616.
Jacobs, J.B. ‘100 Years of Frontal Sinus Surgery’ Laryngoscope. vol. 107 (1997) pp. 1-36.
K-Splint Internal Nasal Splints; Jan. 25, 2007; www.invotec.net/rhinology/ksplint.html.
Kaiser, H. et al ‘Cortizontherapie, Corticoide in Klinik und Praxis’ Thieme, Stuggart (1992) pp. 390-401.
Kennedy, D.W., M.D. et al. ‘Diseases of the Sinuses: Diagnosis and Management’ (Copyright 2001) by B.C. Decker Inc.
Khomutov, S.M. et al. ‘Dissolution of a Mixture of Steroids in Cyclodextrin Solutions: a Model Description’ Pharmaceutical Chemistry Journal. vol. 35, No. 11 (Nov. 2001) pp. 627-629.
Kingdom, T.T. et al. ‘Image-Guided Surgery of the Sinuses: Current Technology and Applications’ Otolaryngol. Clin. North Am. vol. 37, No. 2 (Apr. 2004) pp. 381-400.
Klossek, J.M. et al. ‘Local Safety of Intranasal Trimcinolone Acentonide: Clinical and Histological Aspects of Nasal Mucosa in the Long-Term Treatment of Perennial Allergic Rhinitis’ Rhinology. vol. 39, No. 1 (2001) pp. 17-22.
Kozlov et al. ‘Diagnosis and Treatment of Sinusitis by YAMIK Sinus Catheters’ Rhinology (1996) vol. 34, pp. 123-124.
Kuhn, et al. ‘The Agger Nasi Cell in Frontal Recess Obstruction: An Anatomic, Radiology and Clinical Correlation’ Operative Techniques in Otolaryngology—Head and Neck Surgery. vol. 2, No. 4 (1991) pp. 226-231.
Laliberte, F. et al. ‘Clinical and Pathologic Methods to Assess the Long-Term Safety of Nasal Corticosteroids’ Allergy. vol. 55, No. 8 (2000) pp. 718-722.
Lang, E.V., et al., ‘Access Systems for Puncture at an Acute Angle’ J. Vasc. Interv. Radiol. (1995) vol. 6, No. 5 pp. 711-713.
Lanza, D.C. ‘Postoperative Care and Avoiding Frontal Recess Stenosis’ Internatinal Advanced Sinus Symposium Jul. 21-24, 1993.
Large, G.C. ‘Crystalline Tetracycline Hydrochloride in the Treatment of Acute and Chronic Maxillary Sinusitis’ Canad. M.A.J. (1958) vol. 79 pp. 15-16.
Lund, V.J. ‘Maximal Medical Therapy for Chronic Rhinosinusitis’ Otolaryngol Clin N. Am. vol. 38 (2005) pp. 1301-1310.
Maran, A.G.D. et al. ‘The Use of the Foley Balloon Catheter in the Tripod Fracture’ J. Laryngol. Otol. (1971) vol. 85, Issue 9, pp. 897-902.
May, M. et al. ‘Frontal Sinus Surgery: Endonasal Drainage Instead of an External Osteopolstic Approach’ Op Tech Otolaryngo Head Neck Surgery. 6 (1995) pp. 184-192.
Medtronic, xomed.com—MicroFrance Catalog Browser. Www.xomcat.com/xomfrance/index.php?zone=both&cat=18&sub=58&oprodline=1272 (Dec. 31, 2003) pp. 1-2.
Mehan, V.K. et al., ‘Coronary Angioplasty through 4 French Diagnostic Catheters’ Cathet. Cardiovasc. Diagn. (1993) vol. 30, No. 1 pp. 22-26.
Mellor, J.M. et al ‘Synthesis of Trifluromethylnaphthalenes’ Tetrahedron. vol. 56 (2000) pp. 10067-10074. Elsevier Science Ltd.
Metson, R., et al., ‘Endoscopic Treatment of Sphenoid Sinusitis’ Otolaryngol. Head Neck Surg. (1996) vol. 114, No. 6 pp. 736-744.

(56) References Cited

OTHER PUBLICATIONS

Metson, R. 'Holmium: YAG Laser Endoscopic Sinus Surgery: A Randomized Controlled Study' Largyngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome Test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Publ pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 290 (May 15, 2000) pp. 1197-1202.
Sama, A., et al., 'Current Opinions on the Surgical Management of Frontal Sinus Disease' ENT News. www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitemnent Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnetne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Ororinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Would Disclosure/The Tristel Purple Promotion—A Collaboration between Tristel PLC and Karl Storz Ednoscopy (UK) Ltd.'p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch. Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Chinese Office Action, First Office Action dated Nov. 5, 2012 for CN 200980137396.1.
Chinese Search Report dated Oct. 29, 2012 for Application No. CN 200980137396.1.

(56) References Cited

OTHER PUBLICATIONS

Chinese Search Report dated Jan. 11, 2013 for Application No. CN 200980152995.0.
Chinese Office Action, First Office Action dated Jan. 29, 2013 for CN 200980152995.1.
European Communication dated Sep. 4, 2008 for Application No. EP 05773189.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.

(56) References Cited

OTHER PUBLICATIONS

International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 01, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Mar. 31, 2011 for Application No. PCT/US2009/069143.
International Search Report dated Aug. 9, 2011 for Application No. PCT/US2011/038751.
International Search Report dated May 18, 2012 for Application no. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.
Japanese Office Action, Notification of Reasons for Refusal dated Sep. 18, 2013 for Application No. JP 2011-527942.
English Machine Translation for JP 5-503650.
U.S. Appl. No. 11/648,158, filed Dec. 29, 2006.

(56) References Cited

OTHER PUBLICATIONS

U.S. Appl. No. 11/804,308, filed May 16, 2007.
U.S. Appl. No. 11/804,309, filed May 16, 2007.
U.S. Appl. No. 13/840,430, filed Mar. 15, 2013.
Argon Medical. Maxxim Medical. Ad for Sniper EliteTM Hydrophilic Ni—Ti Alloy Guidewire (2001).
Aust, R., et al. 'The Functional Size of the Human Maxillary Ostium in Vivo' Acta. Otolaryn. (9178) vol. 78 pp. 432-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.

* cited by examiner

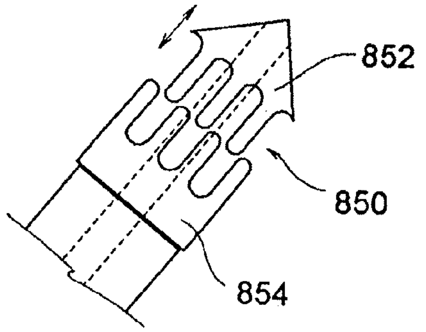
Fig. 5X'
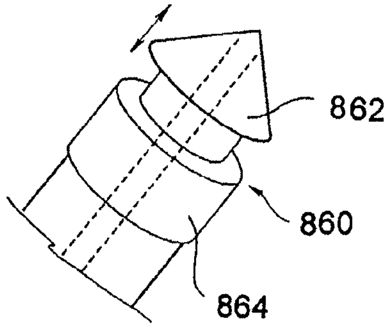
Fig. 5X''
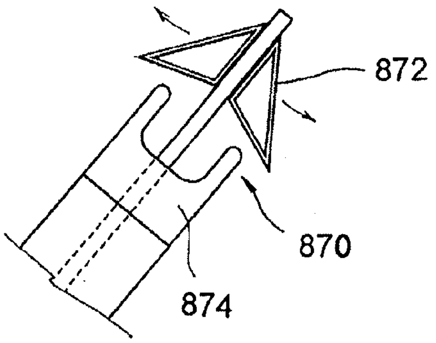
Fig. 5X'''
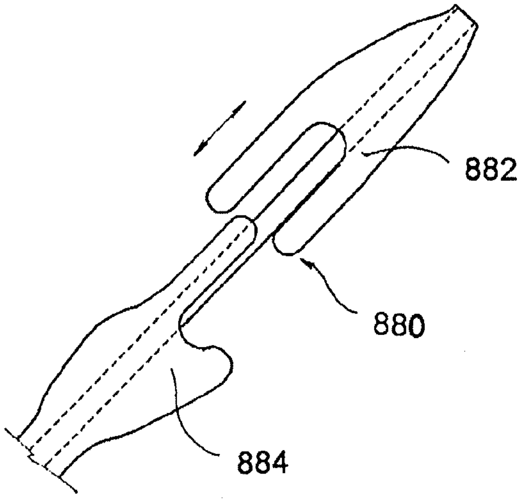
Fig. 5X''''

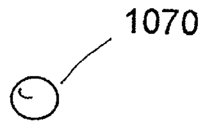
Fig. 5Y I
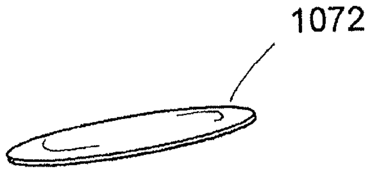
Fig. 5Y II
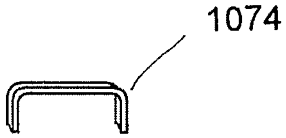
Fig. 5Y III
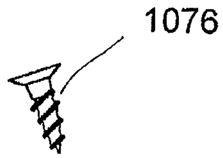
Fig. 5Y IIII
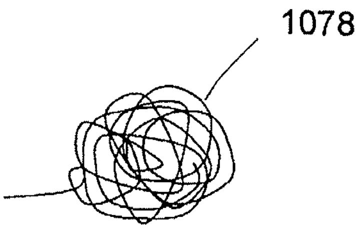
Fig. 5Y IIIII

DEVICES, SYSTEMS AND METHODS FOR DIAGNOSING AND TREATING SINUSITIS AND OTHER DISORDERS OF THE EARS, NOSE AND/OR THROAT

CROSS-REFERENCE TO RELATED APPLICATIONS

This application is a continuation of U.S. Ser. No. 12/042,221, filed Mar. 4, 2008, issued Mar. 27, 2012 as U.S. Pat. No. 8,142,422, which is a continuation of U.S. Ser. No. 10/829,917, filed Apr. 21, 2004, issued Feb. 2, 2010 as U.S. Pat. No. 7,654,997, the entire disclosure of which is expressly incorporated herein by reference.

FIELD OF THE INVENTION

The present invention relates generally to medical devices and methods and more particularly to minimally invasive, catheter based devices, systems and methods for treating sinusitis and other ear, nose & throat disorders.

BACKGROUND OF THE INVENTION

The human nose is responsible for warming, humidifying and filtering inspired air and for conserving heat and moisture from expired air. The nose is also an important cosmetic feature of the face. The nose is formed mainly of cartilage, bone, mucous membranes and skin. The right and left nostrils lead into right and left nasal cavities on either side of the intranasal septum. The right and left nasal cavities extend back to the soft palate, where they merge to form the posterior choanae. The posterior choanae opens into the nasopharynx. The roof of the nose is formed, in part, by a bone known as the cribriform plate. The cribriform plate contains numerous tiny perforations through which sensory nerve fibers extend to the olfactory bulbs. The sensation of smell occurs when inhaled odors contact a small area of mucosa in the superior region of the nose, stimulating the nerve fibers that lead to the olfactory bulbs.

The paranasal sinuses are cavities formed within the bones of the face. The paranasal sinuses include frontal sinuses, ethmoid sinuses, sphenoidal sinuses and maxillary sinuses. The paranasal sinuses are lined with mucous-producing epithelial tissue. Normally, mucous produced by the linings of the paranasal sinuses slowly drains out of each sinus through an opening known as an ostium, and into the nasopharnyx. Disorders that interfere with drainage of mucous (e.g., occlusion of the sinus ostia) can result in a reduced ability of the paranasal sinuses to function normally. This results in mucosal congestion within the paranasal sinuses. Such mucosal congestion of the sinuses can cause damage to the epithelium that lines the sinus with subsequent decreased oxygen tension and microbial growth (e.g., a sinus infection).

The nasal turbinates are three (or sometimes four) bony processes that extend inwardly from the lateral walls of the nose and are covered with mucosal tissue. These turbinates serve to increase the interior surface area of the nose and to impart warmth and moisture to air that is inhaled through the nose. The mucosal tissue that covers the turbinates is capable of becoming engorged with blood and swelling or becoming substantially devoid of blood and shrinking, in response to changes in physiologic or environmental conditions. The curved edge of each turbinate defines a passageway known as a meatus. For example, the inferior meatus is a passageway that passes beneath the inferior turbinate. Ducts, known as the nasolacrimal ducts, drain tears from the eyes into the nose through openings located within the inferior meatus. The middle meatus is a passageway that extends inferior to the middle turbinate. The middle meatus contains the semilunar hiatus, with openings or ostia leading into the maxillary, frontal, and anterior ethmoid sinuses. The superior meatus is located between the superior and medial turbinates.

Nasal Polyps:

Nasal polyps are benign masses that grow from the lining of the nose or paranasal sinuses. Nasal polyps often result from chronic allergic rhinitis or other chronic inflammation of the nasal mucosa. Nasal polyps are also common in children who suffer from cystic fibrosis. In cases where nasal polyps develop to a point where they obstruct normal drainage from the paranasal sinuses, they can cause sinusitis.

Sinusitis:

The term "sinusitis" refers generally to any inflammation or infection of the paranasal sinuses. Sinusitis can be caused by bacteria, viruses, fungi (molds), allergies or combinations thereof. It has been estimated that chronic sinusitis (e.g., lasting more than 3 months or so) results in 18 million to 22 million physician office visits per year in the United States.

Patients who suffer from sinusitis typically experience at least some of the following symptoms:

headaches or facial pain
nasal congestion or post-nasal drainage
difficulty breathing through one or both nostrils
bad breath
pain in the upper teeth Proposed Mechanism of Sinus Pain & Diagnosis The sinuses consist of a series of cavities connected by passageways, ultimately opening into the nasal cavity. As described previously, these passageways and cavities are formed by bone, but covered in mucosa. If the mucosa of one of these passageways becomes inflamed for any reason, the cavities which drain through that passageway can become blocked. This trapping of mucous can be periodic (resulting in episodes of pain) or chronic. Chronically blocked passageways are targets of infection. Ultimately, it is the dimensions of the bony passageways and thickness of the overlying mucosa and its chronicity that dictate the duration and severity of sinus symptoms. Thus, the primary target for sinus therapy is the passageway, with the primary goal to regain drainage. Often CT will not reveal these dimensional issues, especially when the patient is not currently experiencing severe symptoms. Therefore there exists a need to dynamically evaluate the sinus passageways under normal conditions, in response to challenging stimuli. As suggested herein, if it would be possible to assess sinus disease and its dynamic component, one might better target therapy for sinusitis and possibly be able to treat patients in a more focused and minimally invasive manner Such focus on the passageway and the use of flexible instrumentation suggests an entirely new approach to sinus intervention: one utilizing flexible catheters and guidance tools, with passageway and cavity modifying devices capable of being delivered with minimal damage to the surrounding tissues.

Deviated Septum:

The intranasal septum is a cartilaginous anatomical structure that divides one side of the nose from the other. Normally, the septum is relatively straight. A deviated septum is a condition where the cartilage that forms the septum is abnormally curved or bent. A deviated nasal septum may develop as the nose grows or, in some cases, may result from trauma to the nose. A deviated septum can interfere with proper breathing or may obstruct normal drainage of nasal discharge, especially in patient's whose nasal turbinates are swollen or enlarged due to allergy, overuse of decongestant medications, etc. Such interference with drainage of the sinuses can predispose the patient to sinus infections.

A deviated nasal septum that interferes with proper function of the nose can be surgically corrected by a procedure known as septoplasty. In a typical septoplasty procedure, an endoscope is inserted into the nose and the surgeon makes an incision inside the nose, lifts up the lining of the septum, and removes and straightens the underlying bone and cartilage that is abnormally deviated. Such surgical septoplasty procedures can effectively straighten a deviated septum but, because the nasal cartilage has some memory, the septum may tend to resume its original deviated shape.

Reduction/Removal of Nasal Turbinates

Various surgical techniques, including endoscopic surgery, have been used for reduction and/or removal of the inferior turbinate in patient's whose inferior turbinate is chronically enlarged such that it is obstructing normal breathing and/or normal drainage from the paranasal sinuses. Typically, chronic enlargement of the inferior turbinates is the result of allergies or chronic inflammation. Enlargement of the inferior turbinate can be especially problematic in patient's who also suffer from a deviated septum that crowds or impinges upon the soft tissue of the turbinate. Thus, a septoplasty to straighten the deviated septum is sometimes performed concurrently with a reduction of the inferior turbinates.

Sinus Tumors

Most polyps are benign, but one form of a nasal polyp, known as an inverting papilloma, can develop into a malignancy. Unlike most benign polyps, which typically occur on both sides of the nose, an inverting papilloma is usually found on just one side. Thus, in cases where a unilateral polyp is observed, it is usually biopsied to determine if it is malignant. If an inverting papilloma is detected before it becomes malignant and is removed completely, it will typically not recur. However, using the technology that has heretofore been available, it has sometimes been difficult to determine if the papilloma has been entirely removed unless and until regrowth of the polyp is observed on long term post-surgical follow-up.

Various benign sinus tumors have also been known to occur, but are relatively rare. The most common form of malignant sinus tumor is squamous cell carcinoma. Even with surgery and radiation treatment, squamous cell carcinoma of the paranasal sinus is associated with a relatively poor prognosis. Other types of malignant tumors that invade the paranasal sinuses include adenocarcinoma and, more rarely, lymphoma and even more rarely, melanoma.

Facial Fractures

The most common cause of fractures of the facial bones is auto accidents, but facial fractures are also frequently caused by sports injuries, industrial accidents, falls, assaults and gunshot wounds. Some facial fractures involve bones that are accessible from inside the nasal cavities or paranasal sinuses. Notably, the nose is the most commonly injured facial structure due to its prominent position on the face. Thus, fractures of the nasal bone (with or without resultant deviated septum) are not uncommon. Other facial fractures such as fractures of the orbital floor and/or the ethmoid or frontal sinuses are also accessible from inside the nose or sinuses. A common type of orbital floor fracture is a "blowout" fracture that typically results from blunt trauma to the eye where the force is transmitted downwardly causing the relatively thin bone that forms the floor of the orbit to fracture downwardly. This can cause the periorbital tissues to herniate into the maxillary sinus and sometimes can also create a "trap door" of bone that extends downwardly into the maxillary sinus.

Endoscopic Sinus Surgery and Other Current Procedures

Functional Endoscopic Sinus Surgery

The most common corrective surgery for chronic sinusitis is functional endoscopic sinus surgery (FESS). In FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose. Other endoscopic intranasal procedures have been used to remove pituitary tumors, to treat Graves disease (i.e., a complication of hyperthyroidism which results in protrusion of the eyes) and surgical repair of rare conditions wherein cerebrospinal fluid leaks into the nose (i.e., cerebrospinal fluid rhinorrhea).

Surgery to reduce the size of the inferior turbinates can be accomplished with endoscopic visualization (with magnification where desired) and is typically performed with the patient under general anesthesia. An incision is typically made in the mucosa that lines the turbinate to expose the underlying bone. Some quantity of the underlying bone may then be removed. If selective removal of some of the mucosa or soft tissue is also desired, such soft tissue can be debulked or removed through by traditional surgical cutting or by the use of other tissue ablation or debulking apparatus such as microdebriders or lasers. Less frequently, chronically enlarged inferior turbinates have been treated by cryotherapy. It is typically desirable to remove only as much tissue as necessary to restore normal breathing and drainage, as removal of too much tissue from the turbinates can impair the ability of the turbinates to perform their physiological functions of warming and humidifying inspired air and conserving warmth and moisture from expired air. Complications associated with inferior turbinate surgery include bleeding, crusting, dryness, and scarring.

In some patients, the middle turbinate is enlarged due to the presence of an invading air cell (concha bullosa), or the middle turbinate may be malformed (paradoxically bent). Severe ethmoid sinusitis or nasal polyps can also result in enlargement or malformation of the middle turbinates. Since a substantial amount of drainage from the sinuses passes through the middle meatus (i.e., the passage that runs alongside middle turbinate) any enlargement or malformation of the middle turbinate can contribute to sinus problems and require surgical correction. Thus, in some FESS procedures carried out to treat sinusitis, the middle meatus is cleared (e.g., the polyps or hypertorophic tissue are removed) thereby improving sinus drainage. However, the middle turbinate can include some of the olfactory nerve endings that contribute to the patient's sense of smell. For this reason, any reduction of the middle turbinate is typically performed in a very conservative manner with care being taken to preserve as much tissue as possible. In patients who suffer from concha bullosa, this may involve removing the bone on one side of an invading air sac. In the cases where the middle turbinate is malformed, just the offending portion(s) of the turbinate may be removed.

Extended Endoscopic Frontal Sinus Surgery

Because of its narrow anatomical configuration, inflammation of the frontal sinuses can be particularly persistent, even after surgery and/or medical therapy has resolved the inflammation in the other paranasal sinuses. In cases of persistent inflammation of the frontal sinuses, a surgery known as a trans-septal frontal sinusotomy, or modified Lothrop procedure, is sometimes performed. In this procedure, the surgeon removes a portion of the nasal septum and the bony partition between the sinuses to form one large common drainage channel for draining the frontal sinuses into the nose. This complicated procedure, as well as some other ear, nose and throat surgical procedures, can carry a risk of penetrating the cranial vault and causing leakage of cerebrospinal fluid (CSF). Also, some sinus surgeries as well as other ear, nose and throat procedures are performed close to the optic nerves, the eyes, and the brain and can cause damage to those structures. To minimize the potential for such untoward complications or damage, image-guided surgery systems have been used to perform some complex head and neck procedures. In image guided surgery, integrated anatomical information is supplied through CT-scan images or other anatomical mapping data taken before the operation. Data from a preoperative CT scan or other anatomical mapping procedure is downloaded into a computer and special sensors known as localizers are attached to the surgical instruments. Thus, using the computer, the surgeon can ascertain, in three dimensions, the precise position of each localizer-equipped surgical instrument at any given point in time. This information, coupled with the visual observations made through the standard endoscope, can help the surgeon to carefully position the surgical instruments to avoid creating CSF leaks and to avoid causing damage to nerves or other critical structures.

Shortcomings of FESS

Although FESS continues to be the gold standard therapy for severe sinuses, it has several shortfalls. Often patients complain of the post-operative pain and bleeding associated with the procedure, and a significant subset of patients remain symptomatic even after multiple surgeries. Since FESS is considered an option only for the most severe cases (those showing abnormalities under CT scan), a large population of patients exist that can neither tolerate the prescribed medications nor be considered candidates for surgery. Further, because the methodologies to assess sinus disease are primarily static measurements (CT, MRI), patients whose symptoms are episodic are often simply offered drug therapy when in fact underlying mechanical factors may play a significant role. To date, there is no mechanical therapy offered for these patients, and even though they may fail pharmaceutical therapies, no other course of action is indicated. This leaves a large population of patients in need of relief, unwilling or afraid to take steroids, but not sick enough to qualify for surgery.

One of the reasons why FESS and sinus surgery is so bloody and painful relates to the fact that straight instrumentation with rigid shafts are used. Due to the fact that the sinuses are so close to the brain and other important structures, physicians have developed techniques using straight tools and image guidance to reduce the likelihood of penetrating into unwanted areas. In an effort to target deep areas of the anatomy, this reliance on straight instrumentation has resulted in the need to resect and remove or otherwise manipulate any anatomical structures that may lie in the path of the instruments, regardless of whether those anatomical structures are part of the pathology. With the advances in catheter based technology and imaging developed for the cardiovascular system, there exists a significant opportunity to reduce the morbidity of sinus interventional through the use of flexible instrumentation and guidance.

If flexible tools could be developed such that sinus intervention may be able to be carried out with even less bleeding and post-operative pain, these procedures may be applicable to a larger group of patients. Further, as described here, flexible instrumentation may allow the application of new diagnostic and therapeutic modalities that have never before been possible.

Laser or Radiofrequency Turbinate Reduction (Soft Tissue Only)

In cases where it is not necessary to revise the bone that underlies the turbinate, the surgeon may elect to perform a laser or radiofrequency procedure designed to create a coagulative lesion in (or on) the turbinate, which in turn causes the soft tissue of the turbinate to shrink. Also, in some cases, a plasma generator wand may be used create high energy plasma adjacent to the turbinate to cause a reduction in the size of the turbinate.

One example of a radio frequency procedure that may be used to shrink enlarged inferior turbinates is radiofrequency volumetric tissue reduction (RFVTR) using the Somnoplasty® system (Somnus Medical Technologies, Sunnyvale, Calif.). The Somnoplasty® system includes a radio frequency generator attached to a probe. The probe is inserted through the mucosa into the underlying soft tissue of the turbinate, usually under direct visualization. Radiofrequency energy is then delivered to heat the submucosal tissue around the probe, thereby creating a submucosal coagulative lesion while allowing the mucosa to remain in tact. As the coagulative lesion heals, the submucosal tissue shrinks thereby reducing the overall size of the turbinate. Radiofrequency volumetric tissue reduction (RFVTR) can be performed as an office procedure with local anesthesia.

Many of the above-described procedures and techniques may be adaptable to minimally invasive approaches and/or the use of flexible instrumentation. There exists a need in the art for the development of such minimally invasive procedures and techniques as well as instrumentation (e.g., flexible instruments or catheters) useable to perform such procedures and techniques.

SUMMARY OF THE DISCLOSURE

In general, the present invention provides methods, devices and systems for diagnosing and/or treating sinusitis or other conditions of the ear, nose or throat.

In accordance with the present invention, there are provided methods wherein one or more flexible catheters or other flexible elongate devices as described herein are inserted in to the nose, nasopharynx, paranasal sinus, middle ear or associated anatomical passageways to perform an interventional or surgical procedure. Examples of procedures that may be performed using these flexible catheters or other flexible elongate devices include but are not limited to: delivering contrast medium; delivering a therapeutically effective amount of a therapeutic substance; implanting a stent, tissue remodeling device, substance delivery implant or other therapeutic apparatus; cutting, ablating, debulking, cauterizing, heating, freezing, lasing, dilating or otherwise modifying tissue such as nasal polyps, aberrant or enlarged tissue, abnormal tissue, etc.; grafting or implanting cells or tissue; reducing, setting, screwing, applying adhesive to, affixing, decompressing or otherwise treating a fracture; delivering a gene or gene therapy preparation; cutting, ablating, debulking, cauterizing, heating, freezing, lasing, forming an osteotomy or trephination in or otherwise modifying bony or cartilaginous tissue within paranasal sinus or elsewhere within the nose; remodeling or changing the shape, size or configuration of a sinus ostium or other anatomical structure that affects drainage from one or more paranasal sinuses; removing puss or aberrant matter from the paranasal sinus or elsewhere within the nose; scraping or otherwise removing cells that line the interior of a paranasal sinus; removing all or a portion of a tumor; removing a polyp; delivering histamine, an allergen or another substance that causes secretion of mucous by tissues within a paranasal sinus to permit assessment of drainage from the sinus; implanting a cochlear implant or indwelling hearing aid or amplification device, etc.

Further in accordance with the invention, there are provided methods for diagnosing and assessing sinus conditions, including methods for delivering contrast media into cavities, assessing mucosal flow, assessing passageway resistance and cilliary function, exposing certain regions to antigen challenge, etc Still further in accordance with the invention, there are provided novel devices for performing some or all of the procedures described herein.

Further aspects, details and embodiments of the present invention will be understood by those of skill in the art upon reading the following detailed description of the invention and the accompanying drawings.

BRIEF DESCRIPTION OF THE DRAWINGS

FIG. 3C' is a cross sectional view through line 3C'-3C' of FIG. 3C.

FIGS. 3F', 3F" and 3F'" show alternative constructions of the distal portion of the suction cannula of the occluder/suction device shown in FIG. 3F.

FIG. 5G" shows the balloon catheter and stent of FIG. 3G', with the balloon inflated and the stent expanded so as to open or dilate the occluded region within the nose, nasopharynx or paranasal sinus.

FIG. 5G'" shows the balloon catheter and stent of FIG. 3G' with the stent implanted, the balloon deflated and the catheter being withdrawn and removed.

FIGS. 5K' shows the device of FIG. 5K being used to remove a nasal polyp or other obstructive mass from an anatomical passage within the nose or paranasal sinus.

FIG. 5Q' is a cross-sectional view through line 5Q'-5Q' of FIG. 5Q.

FIG. 5R" shows another example of an optional modified shape of the balloon and stent of FIG. 5P.

FIG. 5U' is a cross-sectional view through line 5T'-5T' of FIG. 5U.

FIGS. 5W' and 5W" show steps in a method for using the bone remodeling device of FIG. 5W.

FIGS. 5X'-5X"" are partial perspective views of alternative designs for bone remodeling devices of the present invention.

FIGS. 5Y'-5Y""" are perspective views of examples of substance delivering implant devices useable in the present invention.

DETAILED DESCRIPTION

The following detailed description and the accompanying drawings are intended to describe some, but not necessarily all, examples or embodiments of the invention only and does not limit the scope of the invention in any way.

Figure 1A:
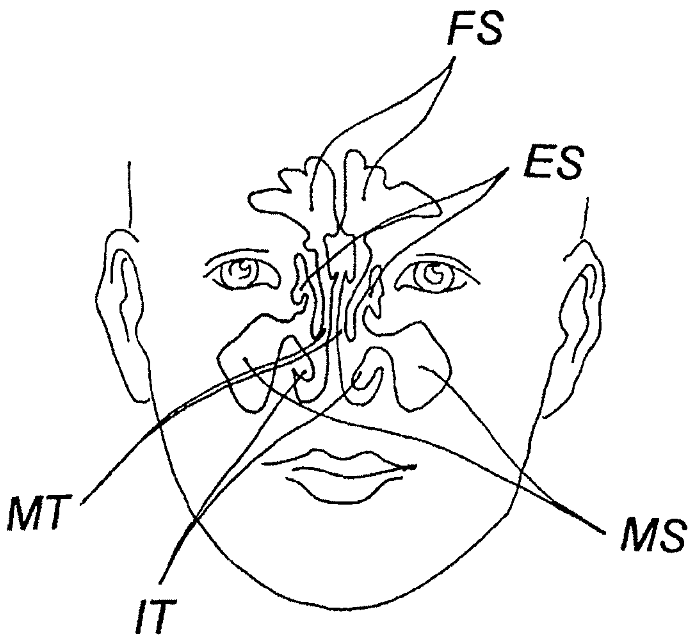
FIG. 1A (Prior Art) is a frontal view of a human head showing the locations of the paranasal sinuses.
Figure 1B:
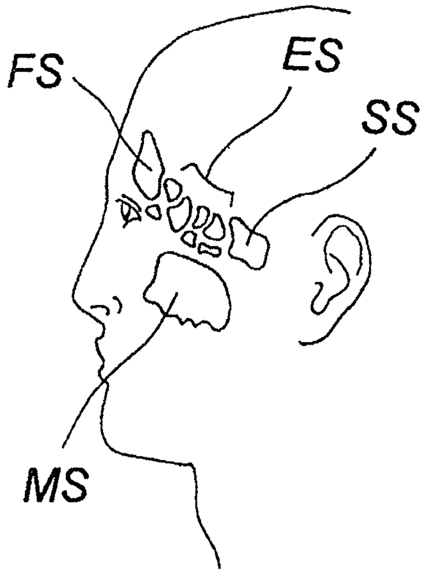
FIG. 1B (Prior Art) is a side view of a human head showing the locations of the paranasal sinuses.

A number of the drawings in this patent application show anatomical structures of the ear, nose and throat. In general, these anatomical structures are labeled with the following reference letters:

Nasal Cavity NC
Nasopharynx NP
Superior Turbinate ST
Middle Turbinate MT
Inferior Turbinate IT
Frontal Sinus FS
Ethmoid Sinus ES
Sphenoid Sinus SS
Sphenoid Sinus Ostium SSO
Maxillary Sinus MS The human nose has right and left nostrils or nares which lead into separate right and left nasal cavities. The right and left nasal cavities are separated by the intranasal septum, which is formed substantially of cartilage and bone. Posterior to the intranasal septum, the nasal cavities converge into a single nasopharyngeal cavity. The right and left Eustachian tubes (i.e., auditory tubes) extend from the middle ear on each side of the head to openings located on the lateral aspects of the nasopharynx. The nasopharynx extends inferiorly over the uvula and into the pharynx. As shown in FIGS. 1A and 1B, paranasal sinuses are formed in the facial bones on either side of the face. The paranasal sinuses open, through individual openings or ostia, into the nasal cavities. The paranasal sinuses include frontal sinuses FS, ethmoid sinuses ES, sphenoidal sinuses SS and maxillary sinuses MS.

The present invention provides a comprehensive system of devices and associated methods for diagnosing and treating disorders of the ears, nose and throat in a less invasive fashion than current day approaches. Specifically, examples of which are described below, the invention provides devices that wholly or partially effect a fluid-tight seal of the operative field (e.g., the nasopharynx and/or one or more of the sinus cavities or regional ducts). This fluid-tight sealing of the operative field allows the cavities, ducts and passageways to be imaged using fluid/gas based agents in combination with various imaging modalities without the risk of aspiration or uncontrolled leakage of fluid from the operative field. Further, this fluid-tight sealing of the operative field permits the retention and collection of any blood or flushing fluids released during the procedure. Another aspect of the invention is a set of methods and devices useable to assess the static and dynamic nature of the paranasal sinuses and to provide for the guidance of specific therapies to particular sinuses or particular target regions (e.g., stenotic sinus ostia, infected tissues within sinuses, tumors, other target structures). Another aspect of the invention is the use of devices and methods which are designed for minimally invasive entry into the sinus passageways or regional ducts under image and/or endoscopic guidance to provide local therapy such as dilation, ablation, resection, injection, implantation, etc. to the region of concern. These devices and methods may be disposable or temporary in their application, or they may be implantable with on-going functionality (such as implantable drug delivery systems, cochlear implants, etc.). In a number of embodiments, the present invention utilizes flexible catheters and various working devices that are mounted on or delivered through elongate flexible members or catheters, to diagnose and treat a wide range or ear, nose and throat disorders including; nasal polyps, sinusitis, enlarged turbinates, deviated septum, tumors, infections, deformities, etc. The following pages describe a number of specific devices and methods that are useable in accordance with this invention. It is to be understood that any component, element, limitation, attribute or step described in relation to any particular device or method described herebelow, may be incorporated in or used with any other device or method of the present invention unless to do so would render the resultant device or method unusable for its intended purpose.

A. Occluders & Access Port Devices

Figure 5A:
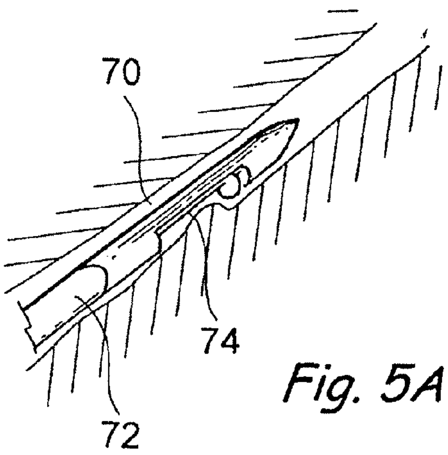
FIG. 5A is a partial perspective view of a side cutting or ablation device being used in accordance with the present invention.
Figure 5B:
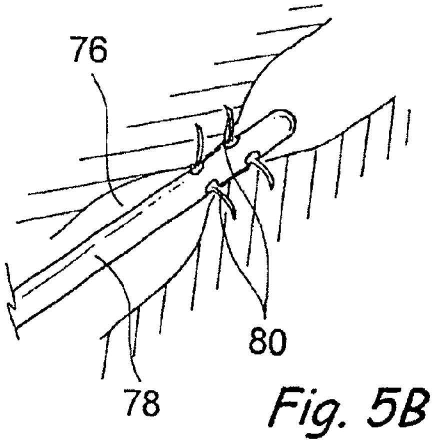
FIG. 5B is a partial perspective view of a device having laterally deployable needles, electrodes or other treatment delivering projections, being used in accordance with the present invention.

Many of the procedures of the present invention require the insertion and positioning of one or more flexible catheters or other flexible elongate working devices (examples of which are shown in FIGS. 5A-5Y'''' and described herebelow) within the nose, nasopharynx, middle ear or paranasal sinuses. To facilitate the insertion and proper positioning of such catheters and/or other elongate working devices and to prevent undesirable drainage of blood or debris from the operative site, the present invention includes a number of different occluder and/or access port devices, examples of which are shown in FIGS. 2A-2R, that are inserted through the nose and/or oral cavity and function to a) prevent unwanted drainage or escape of fluid (e.g., gas or liquid) and b) facilitate the insertion and positioning of guides and working devices, examples of such working devices being shown in FIGS. 5A-5Y'''' and 6A-6E.

Figures 2A, 2B:
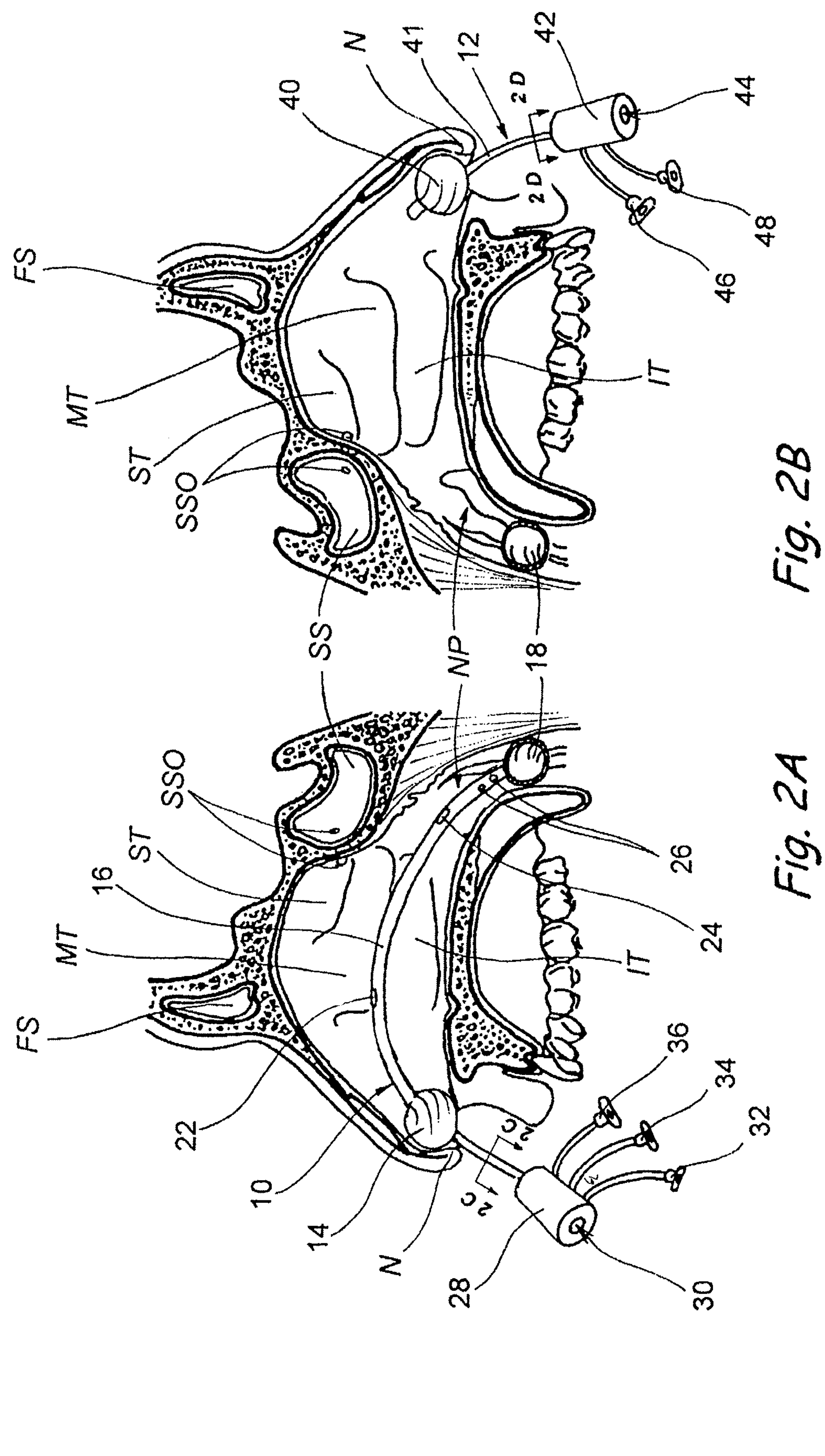
FIG. 2A is a partial sectional view of head of a human patient showing the right nasal cavity, the right side of the nasopharynx and the associated paranasal sinuses, with an anterior/posterior occluder & access device of the present invention inserted therein.
FIG. 2B is a partial sectional view of head of a human patient showing the left nasal cavity, the left side of the nasopharynx and the associated paranasal sinuses, with an anterior occluder & access device of the present invention inserted therein.

FIGS. 2A-2B show partial sectional views of opposite sides of the head of a human patient having an anterior/posterior occluder & access device 10 inserted through the right nasal cavity and anterior occluder & access device 12 positioned in the anterior region of the left nasal cavity. Specifically, FIG. 2A shows the nasal cavity, the right side of the nasopharynx and the associated paranasal sinuses, with an anterior/posterior occluder & access device 10 of the present invention inserted therein. The anterior/posterior occluder & access device 10 comprises an anterior occluder 14 which occludes the right nasal cavity on the right side of the nasal septum, a posterior occluder 18 that occludes the posterior choanae, nasopharynx or pharynx posterior to the nasal septum (but typically superior to the glottis) and a tube 16 that extends between the anterior occluder 14 and posterior occluder 18. Devices for posterior occlusion and anterior occlusion may be used alone or in combination. They may be coaxially deployed or alternatively they may be deployed in a singular fashion, one in each orifice. It should be noted that any combination of these sealing modalities may be employed to achieve one or more of the stated objectives. A cross-section through the tube 16 is shown in FIG. 2C. Other cross-sectional configurations could also be possible, including those that comprise more lumens to permit the passage of multiple devices or fluids (e.g., liquid or gases). In some embodiments, it may be desirable for the device 10 (or any of the other occluder/access devices described herein) to have separate lumens for infusion and aspiration, thereby allowing for concurrent infusion of an irrigation fluid or other fluid and suctioning of the irrigation fluid or other fluid from the operative field. Such continuous turnover of fluid within a sealed operative field may be useful for clearing blood or debris from the operative field to facilitate unobstructed viewing of the anatomical structures using an endoscope or for various other reasons. A port body 28 as attached to the proximal end of the tube 16. A device insertion aperture 30 extends through the port body 28 into working lumen 50 of tube 16. One or more outlet openings 22, 24 are at location(s) in the tube such that a device (e.g., a catheter, fluid injector or other elongate device examples of which are shown in FIGS. 5A-5Y"" and described herebelow) or fluid(s) may be inserted into the device insertion opening 30, advanced through the working lumen 50 and out of a selected one of the outlet openings 22, 24 to a position within the nose, nasopharynx or paranasal sinus. In the particular embodiment shown in FIG. 2A the anterior and posterior occluders 14, 18 comprise balloons, but various other types of occluders could be used in place of balloons, examples of which are shown in FIGS. 3A-3K and described herebelow. Balloon inflation/deflation lumens 52, 56 extends from proximal Luer connectors 32, 36, through the tube 16 and to the anterior occluder 14 and posterior occluder 18, respectively. Thus, a syringe or other fluid expelling and/or withdrawing device may be connected to connector 32 and used to selectively inflate and/or deflate the anterior occluder 14. Another syringe or other fluid expelling and/or withdrawing device may be connected to connector 36 and used to selectively inflate and/or deflate the posterior occluder 18. As may be appreciated from the showing of FIG. 2B, the posterior occluder (when fully inflated) may be sized and shaped to occlude the entire posterior choanae, nasopharynx or pharynx posterior to the nasal septum (but typically superior to the glottis), thereby preventing blood or other fluid or debris from draining into the patient's pharynx from either the right or left nasal cavity. When fully inflated, the anterior occluder 14 of the device 10 occludes only the right nasal cavity and serves to prevent blood, other fluid or debris from draining around the tube 16 and out of the right nostril during the operative procedure. A one way valve, such as a flapper valve, duckbill valve, hemostatic valve or other one way valve of the type well known in the art of biomedical device design, may be positioned within the port body 28 to permit a catheter or other elongate device (examples of which are shown in FIGS. 5A-5T and described herebelow) to be advanced in the distal direction though insertion port 30, through the port body 28 and through the working lumen 50 but to prevent blood, other fluid or debris from draining through the working lumen 50 out of the device insertion port 30. In this manner, the device 10 forms a substantially fluid tight anterior seal in the anterior aspect of the right nasal cavity and a substantially fluid tight posterior seal in the posterior choanae, nasopharynx or pharynx posterior to the nasal septum (but typically superior to the glottis). Since a substantially fluid tight seal is formed, one or more valves (not shown) may be provided to relieve positive or negative pressure created between the anterior or posterior occluders 14, 18 as a result of the injection of matter (e.g., contrast medium, irrigation solution, medicament, etc.) into the operative field and/or suctioning or removal of matter (e.g., blood, other fluid or debris) from the operative field. Additionally, a suction lumen 54 may extend from suction Luer connector 34, through suction lumen 54 and to suction openings 26 may be formed in the tube 16. A suction pump may be connected to the suction connector 34 to aspirate blood, other fluid and/or debris out of the right nasal operative region defined between anterior occluder 14 and posterior occluder 18. It should be appreciated that, while the occlusion/access devices shown in the drawings and described herein are designed to isolate a relatively large operative field (e.g., one or both nasal cavities, sinus, nasal cavities-nasopharynx, etc.), once a specific problem has been diagnosed and/or once a specific target region has been identified, the occluders 14, 18 may be repositioned and/or other occluder devices may be inserted to isolate and form a fluid tight seal of just a portion of the original operative field (e.g., just one sinus, one nasal cavity, one Eustachian tube, etc.) thereby allowing the procedure to go forward with only the necessary region(s) of the nose, nasopharynx, paranasal sinuses or other structures sealed off and/or instrumented, to minimize trauma and improve patient comfort.

It should be appreciated that in any embodiment of an anterior/posterior occluder & access device, such as the device 10 shown in FIGS. 2A and 2B, the distance between the anterior occluder 14 and posterior occluder 18 may be adjustable so as to accommodate variations in anatomy and/or specific target regions or isolated operative fields of interest. The anterior and posterior occluders 14, 18 may be separate devices where the anterior occluder may slide or pass through one lumen of the posterior occluder, which may contain several lumens (e.g., inflation, working channel, irrigation, etc.), and may or may not be integrated with the posterior occluder. The posterior occluder may also contain several lumens (e.g., inflation, working channel, irrigation, etc.). Additionally, all lumens for both the anterior and posterior occluders may contain valves so as to prevent leakage or flow of gas, fluid, blood, etc.

It is to be further appreciated that in embodiments that have anterior and posterior outlet openings 22, 24 (as shown in the example of FIGS. 2A-2B) tools, instrumentation and fluids may be delivered via either of the posterior or anterior access ports 22, 24. In some cases, access via a posterior outlet 24 is desirable to gain a better perspective on the target anatomical lumen or lumen (i.e. openings to the ethmoid cells).

Figure 2D:
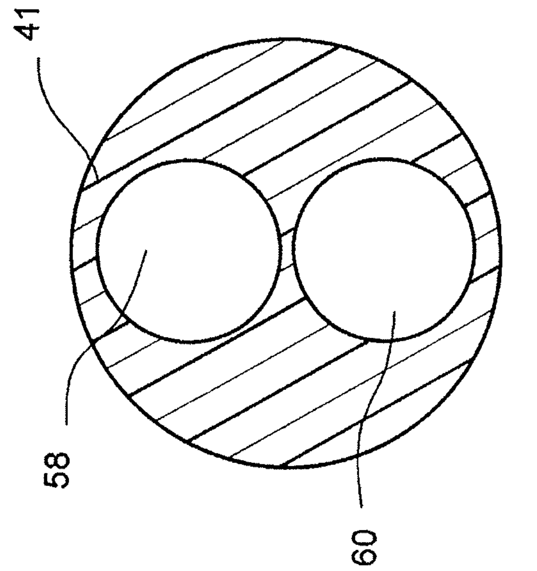
FIG. 2D is a cross sectional view through line D-D of FIG. 2B.
Figure 2C:
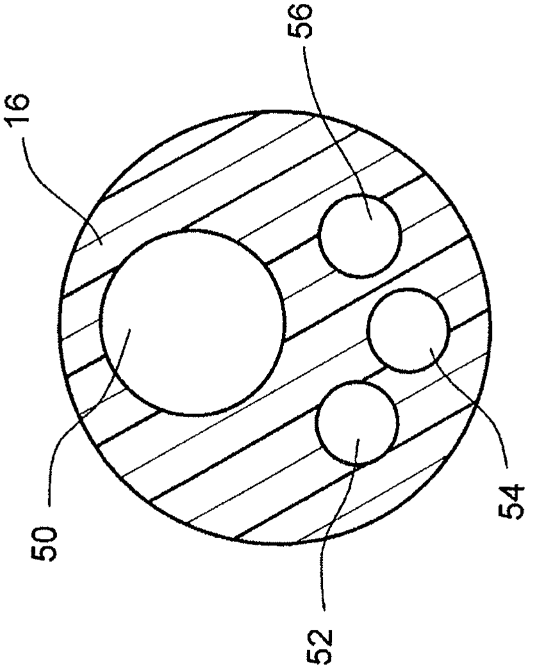
FIG. 2C is a cross sectional view through line C-C of FIG. 2A.
Figure 2E:
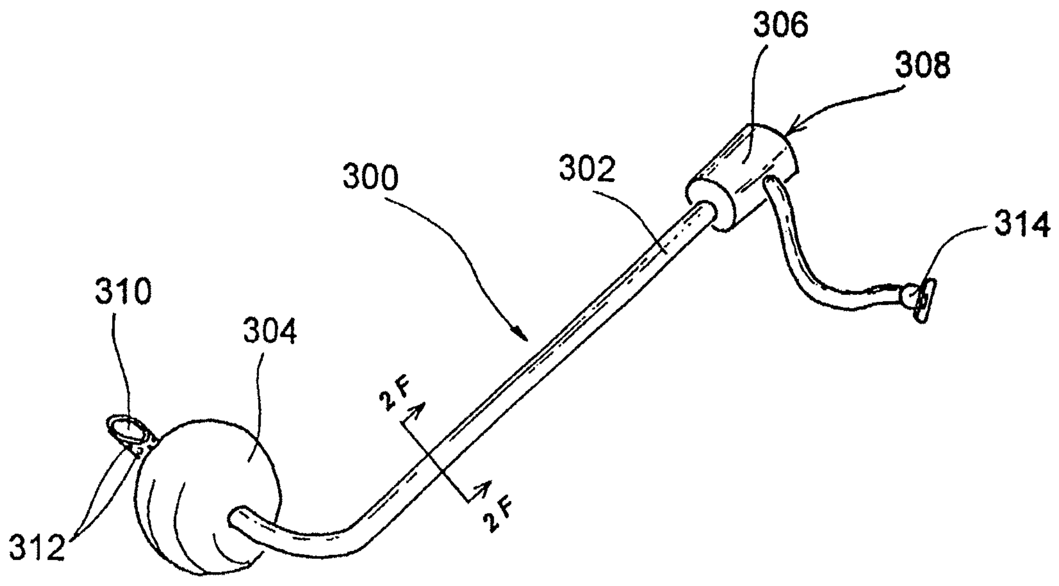
FIG. 2E is a perspective view of a posterior occluder/suction/access device of the present invention that is insertable through the oral cavity.
Figure 2F:
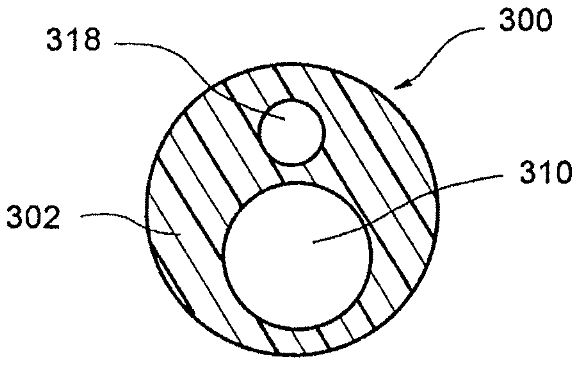
FIG. 2F is a cross-sectional view through Line 2F-2F of FIG. 2E.

As shown in FIGS. 2B and 2D, in some procedures wherein the anterior/posterior occluder & access device 10 is inserted through one nasal cavity, it may be desirable to position a separate anterior occluder & access device 12 within the opposite nasal cavity to prevent drainage of blood, other fluid or debris from the other nostril and to facilitate insertion of catheters or other elongate devices (examples of which are shown in FIGS. 5A-5T and described herebelow) into the left nasal cavity and the paranasal sinuses or other anatomical structures accessible from the other nasal cavity. As shown, in FIG. 2B, the anterior occluder & access device 12 may comprise a tube 41 having an anterior occluder 40 and a port body 42 attached thereto. A device insertion aperture 44 extends through the port body 42 and through a working lumen 58 of tube 41 to an outlet aperture in the distal end of tube 41. A one way valve (such as the valve described hereabove in connection with the anterior/posterior occluder & access device 10) may optionally be provided within port body 42 to prevent draining of blood, other fluid or debris out of insertion aperture 44. In the particular embodiment shown in FIGS. 2B and 2D, the anterior occluder 40 is a balloon, but such occluder 40 may be of various other constructions, examples of which are shown in FIGS. 3A-3M" and described herebelow. To facilitate inflation and deflation of this balloon type anterior occluder 40, a balloon inflation/deflation lumen 60 extends from Luer connector 48, through tube 41 to the balloon-type anterior occluder 40. A syringe or other fluid expelling and/or withdrawing device may be connected to connector 48 and used to selectively inflate and/or deflate the anterior occluder 40. Optionally, a side tube and Luer connector 46 may be connected to the working lumen 58 of tube 41 to allow blood, other fluid and debris to be suctioned from the left nasal cavity through the working lumen 58 of tube 41. In some embodiments, dedicated suction and/or irrigation lumen(s) with separate suction and/or irrigation ports may be formed in tube 41 in a manner similar to that described hereabove with respect to the anterior/posterior occluder & access device 10.

Figures 2G, 2H:
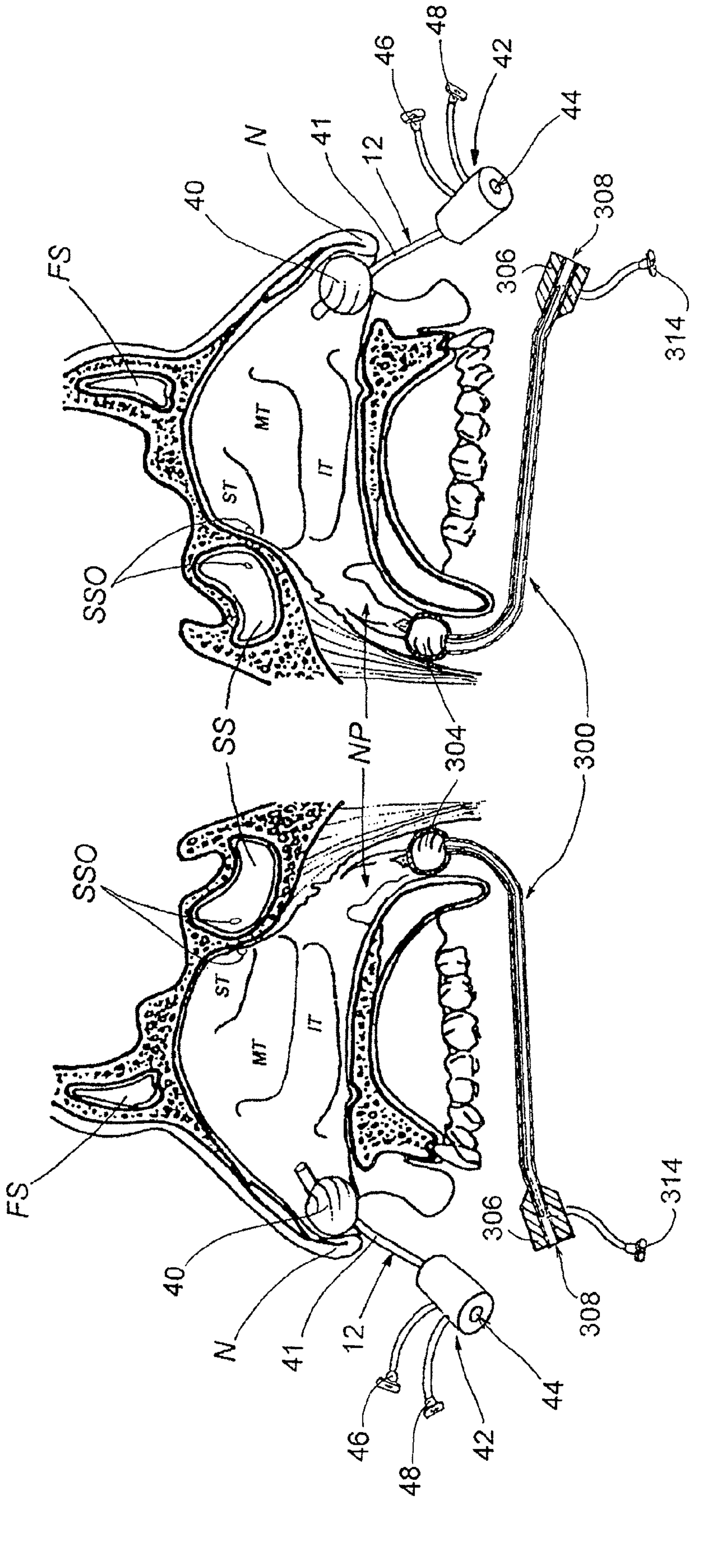
FIG. 2G is a partial sectional view of head of a human patient showing the right nasal cavity, the right side of the nasopharynx and the associated paranasal sinuses, with an anterior occluder & access device of the present invention inserted in the right nasal cavity and a posterior occluder/suction/access device of FIG. 2E inserted through the oral cavity.
FIG. 2H is a partial sectional view of head of a human patient showing the left nasal cavity, the left side of the nasopharynx and the associated paranasal sinuses, with an anterior occluder & access device of the present invention inserted in the left nasal cavity and the same posterior occluder/suction/access device that appears in FIG. 2G extending through the oral cavity.
Figure 2I:
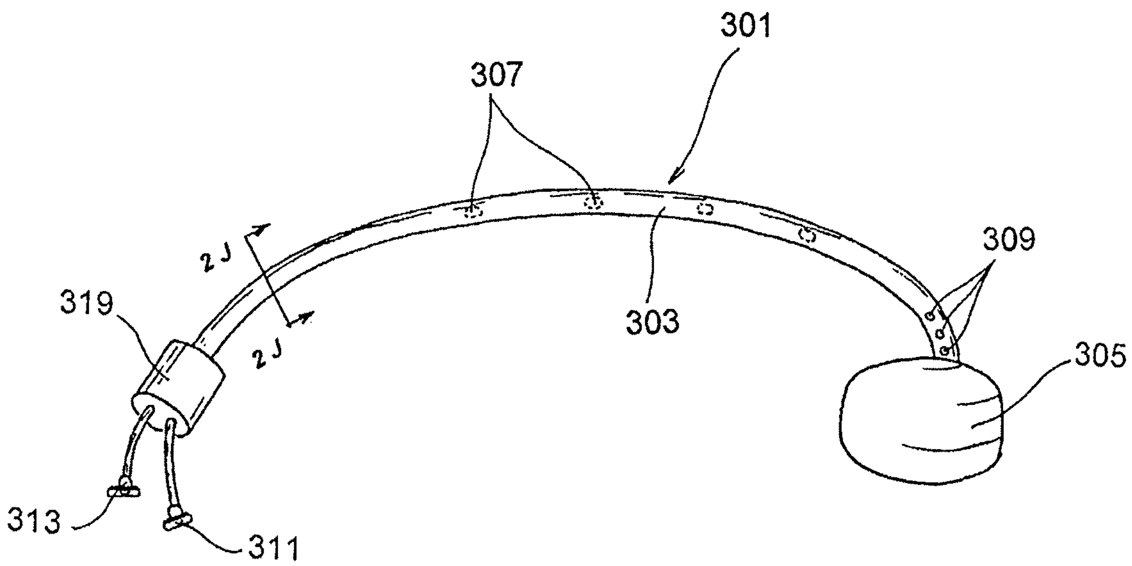
FIG. 2I is a perspective view of a posterior occluder/suction device of the present invention that is insertable transnasally.
Figure 2J:
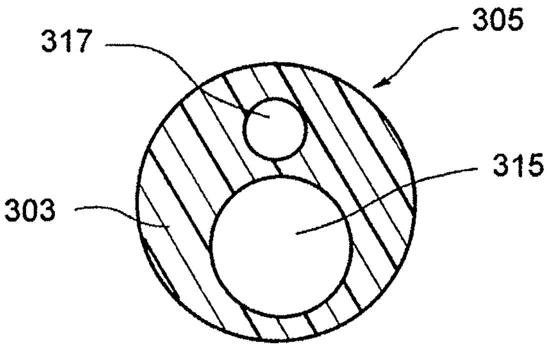
FIG. 2J is a cross-sectional view through Line 2J-2J of FIG. 2I.

FIGS. 2E-2H show an alternative system for occlusion and access, wherein anterior occluder & access device(s) 12 is/are positioned in one or both nostrils or nasal cavities and an orally insertable posterior occluder device 300 is inserted through the patient's oral cavity and positioned so as to occlude the posterior choanae, nasopharynx or pharynx posterior to the nasal septum (but typically superior to the glottis). The embodiment of the orally insertable posterior occluder device 300 shown in FIGS. 2E-2G comprises a curved tube 302 having an occluder 304 positioned at or near the distal end thereof. The device 300 is configured such that it may be inserted through the patient's oral cavity to a position where the occluder 304 is located within, and disposed, so as to substantially occlude the posterior choanae, nasopharynx or pharynx posterior to the nasal septum (but typically superior to the glottis). The posterior occluder 304 may also be positioned next to the Eustachian tube to block the Eustachian tube, thereby preventing fluid from tracking into the Eustachian tube during the procedure (if access to the Eustachian tube or middle ear or inner ear is not desired). Further, it may be necessary to place specific targeted balloons or occluders in ducts or channels which are not intended to be intervened upon (lacrimal ducts, Eustachian tubes, etc.). In such cases, these extra ductal occluders serve to prevent aberrant fluid/gas loss and/or to maintain the integrity of the lumen, while other nearby structures are being modified. In the particular example shown in FIGS. 2E-2G, the occluder 304 comprises a balloon. However, such occluder 304 may be constructed in various alternative ways, examples of which are shown in FIGS. 3A-3K and described herebelow. As may be appreciated from the cross-sectional showing of FIG. 2F, in this example a balloon inflation/deflation lumen 318 may extend from Luer connector 314, through tube 302 to the balloon-type occluder 304. A syringe or other inflation/deflation apparatus may be attached to the Luer connector 314 and used to inflate and deflate the balloon 304. A stopcock or other valve (not shown) may also be provided on balloon inflation tube 318 to maintain inflation of the balloon when desired. In routine use, the occluder 304 is initially deflated and the device 300 is inserted through the oral cavity and advanced to its desired position with the deflated occluder positioned within the posterior choanae, nasopharynx or pharynx posterior to the nasal septum (but typically superior to the glottis). Thereafter, the occluder 304 may be expanded (e.g., inflated) such that it occludes or blocks the posterior choanae, nasopharynx or pharynx posterior to the nasal septum (but typically superior to the glottis), thereby substantially preventing blood, other fluid or debris from draining into the patient's esophagus or trachea during the procedure. In some cases, as shown in FIGS. 2E-2H, the tube 302 may have one or more lumen(s) 310 that extend(s) through the occluder 304 and open(s) through an opening 310 distal to the balloon. Working devices, such as catheters or other elongate devices examples of which are shown in FIGS. 5A-5Y"''' and described herebelow may be advanced through such a lumen 310 and into the patient's nasopharynx, nasal cavities, paranasal sinuses, middle ears, etc. Alternatively, suction may be applied to such a lumen 310 to suction blood, other fluid or debris from the area superior to the occluder 304. In some cases, the lumen 310 shown may be divided into a working lumen and a suction lumen. The suction lumen may terminate in separate suction port(s) (not shown) at the distal end of the tube and a connector (not shown) at the proximal end, such that suction may be applied through a lumen that is separate from the lumen through which the working device(s) is/are passed. A port body 306 may be positioned on the proximal end of the tube 302. A device insertion port 308 may extend through the port body 306 into a lumen 310 of the tube 302. A one way valve, such as a flapper valve, duckbill valve, hemostatic valve or other one way valve of the type well known in the art of biomedical device design, may be positioned within the port body 306 to permit a catheter or other elongate device to be advanced in the distal direction though insertion port 308, through the port body 306 and through a lumen 310 but to prevent blood, other fluid or debris from draining through the lumen 310 and out of the device insertion port 308. In some cases, the orally insertable posterior occluder device 300 may be used without any anterior occluder device(s) positioned in the nostril(s) or nasal cavity(ies). In other cases, it will be desirable to use this orally insertable posterior occluder device 300 in combination with one or two anterior occluder & access devices 12 as shown in the example of FIGS. 2G and 2H. The use of these devices 300, 12 in combination serves to establish a substantially fluid tight operative field between the posterior occluder 304 and the anterior occluder(s) 40 while allowing various catheters and other operative instruments to be inserted into the operative field through optional access ports 44 and/or 308.

Figure 2L:
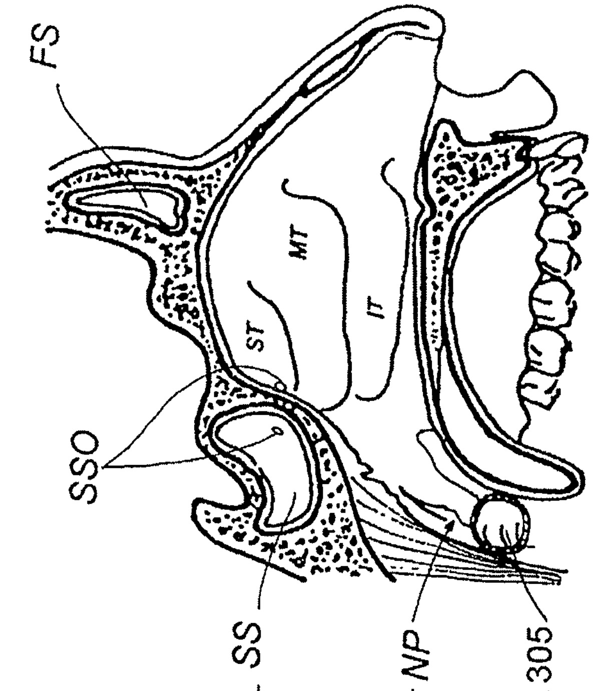
FIG. 2L is a partial sectional view of head of a human patient showing the left nasal cavity, the left side of the nasopharynx and the associated paranasal sinuses and showing the posterior occluder portion of the device of FIG. 2K residing in and occluding the nasopharynx at a location posterior to the septum and superior to the glottis.
Figure 2K:
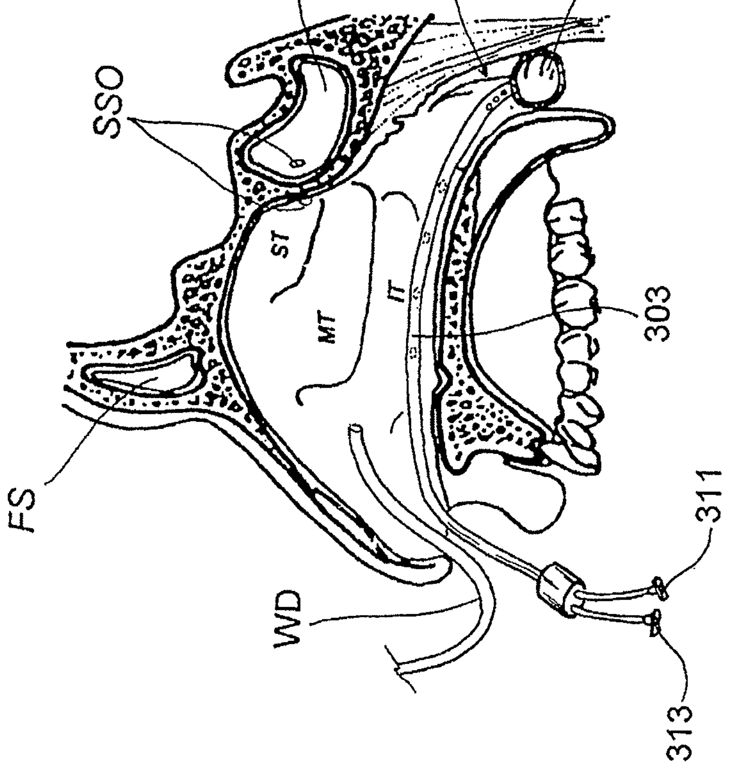
FIG. 2K is a partial sectional view of head of a human patient showing the right nasal cavity, the right side of the nasopharynx and the associated paranasal sinuses, with the posterior occluder/suction device shown in FIG. 2I inserted through the right nasal cavity.

FIGS. 2I-2L show a trans-nasally insertable posterior occluder device 301 that does not include any anterior occluder. This device 301 comprises a curved tube 303 having an occluder 305 positioned at or near the distal end of the tube 303. As shown in FIGS. 2K-2L, this device 301 is inserted through either the right or left nasal cavity and advanced to a position where the occluder 305 substantially occludes the posterior choanae, nasopharynx or pharynx posterior to the nasal septum (but typically superior to the glottis). In the particular example shown, this occluder 305 comprises a balloon. However, such occluder 305 may be constructed in various alternative ways, examples of which are shown in FIGS. 3A-3K and described herebelow. As may be appreciated from the cross-sectional showing of FIG. 2J, in this example a balloon inflation/deflation lumen 317 may extend from Luer connector 311, through tube 303 to the balloon-type occluder 305. A syringe or other inflation/deflation apparatus may be attached to the Luer connector 311 and used to inflate and deflate the balloon-type occluder 305. A stopcock or other valve (not shown) may also be provided on balloon inflation lumen 317 to maintain inflation of the balloon when desired. In routine use, the occluder 305 is initially deflated and the device 301 is inserted through the right or left nasal cavity and advanced to its desired position where the deflated occluder 305 is positioned within the posterior choanae, nasopharynx or pharynx posterior to the nasal septum (but typically superior to the glottis). Thereafter, the occluder 305 may be expanded (e.g., inflated) such that it occludes or blocks the posterior choanae, nasopharynx or pharynx posterior to the nasal septum (but typically superior to the glottis), thereby substantially preventing blood, other fluid or debris from draining into the patient's esophagus or trachea during the procedure. Optionally, distal suction ports 309 and/or proximal suction ports 307 may open into lumen 315 of the tube 303 and such lumen 315 may be attached to a suction connector 313. In this manner, suction may be applied to remove blood, other fluid or debris from the nasopharynx superior to the occluder 305 and/or from the nasal cavity through which the device 3301 is inserted. As may be appreciated from the showings of FIGS. 2K and 2L, in this example, the trans-nasal posterior occluder device 301 is inserted through the right nasal cavity. A working device WD such as a catheter or other elongate operative apparatus (examples of which are shown in FIGS. 5A-5Y'"" and described herebelow) may be advanced into the right nasal cavity adjacent to the tube 303 or through the left nasal cavity which remains open, as no anterior occlusion is provided by this trans-nasal posterior occluder device 301. This arrangement may be particularly suitable for procedures where the physician desires to directly visualize, through the nostril(s), the anatomical structures within the nose, such as the inferior, middle or superior turbinates IT, MT, ST, as shown in FIGS. 2K-2L.

Figures 2M, 2N:
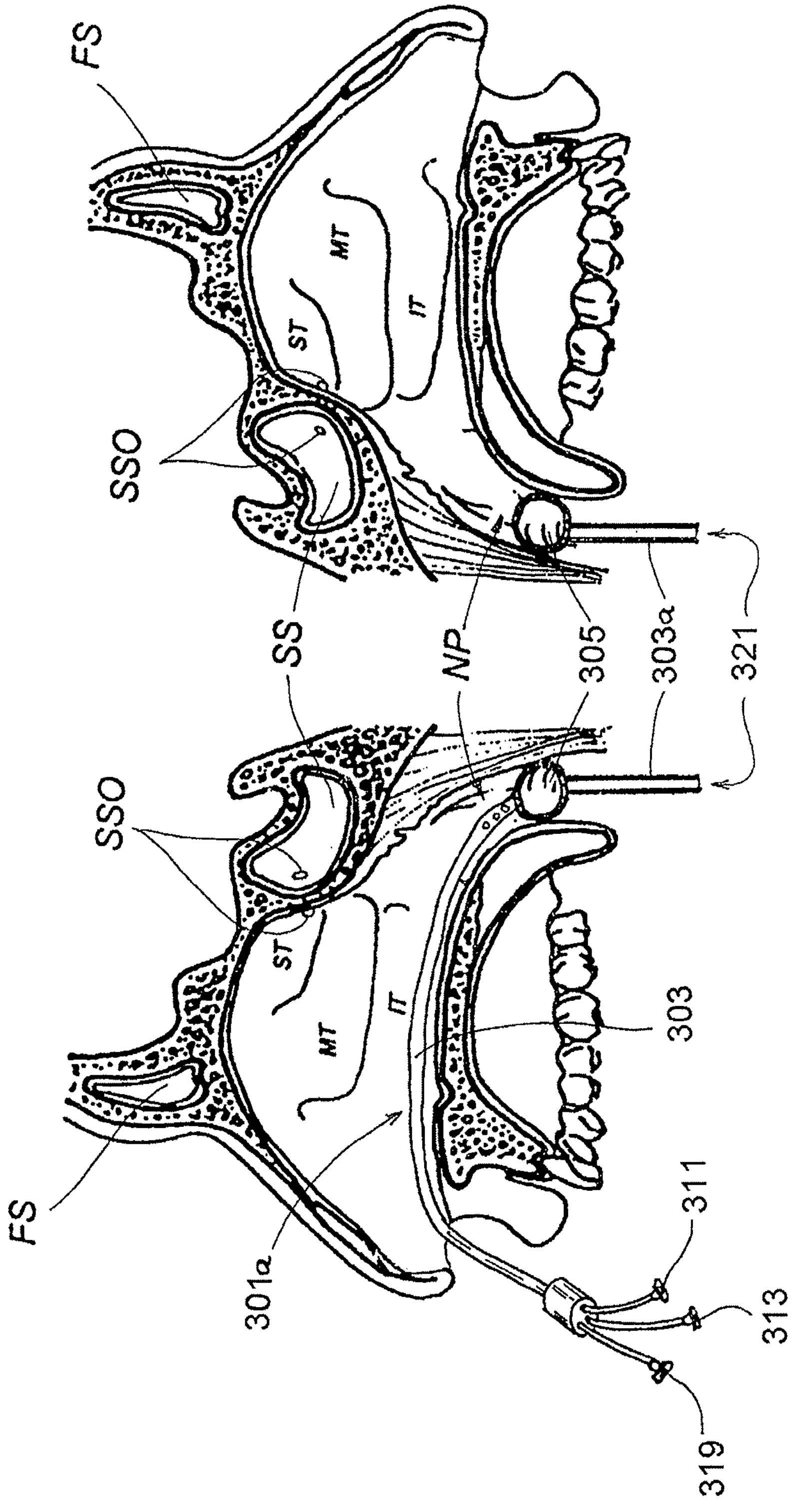
FIG. 2M is a partial sectional view of head of a human patient showing the right nasal cavity, the right side of the nasopharynx and the associated paranasal sinuses, with an extended posterior occluder/suction device inserted through the right nasal cavity.
FIG. 2N is a partial sectional view of head of a human patient showing the left nasal cavity, the left side of the nasopharynx and the associated paranasal sinuses and showing the posterior occluder and distal tubular extension portions of the device of FIG. 2M residing in the nasopharynx posterior to the septum and superior to the glottis.

FIGS. 2M-2N show a modified version of the trans-nasal posterior occluder 301*a* which includes all of the elements described above with respect to the trans-nasal posterior occluder device 301 shown in FIGS. 2I-2L as well as a distal extension 303*a* of the tube 303 that extends distal to the occluder 305 and an additional proximal connector 319. A separate lumen (not shown) extends from connector 319 through tube 303 and through distal tube extension 303*a*, which terminates in a distal end opening 321. Suction may thus be applied to connector 319 to suction matter through distal opening 321, through the distal tube extension 303*a* and through tube 303. This distal tube extension 303*a* and additional lumen may be optionally added to any other the other posterior occluder devices described herein in cases where doing so would not render the device unsuitable for its intended application.

Figures 2O, 2P:
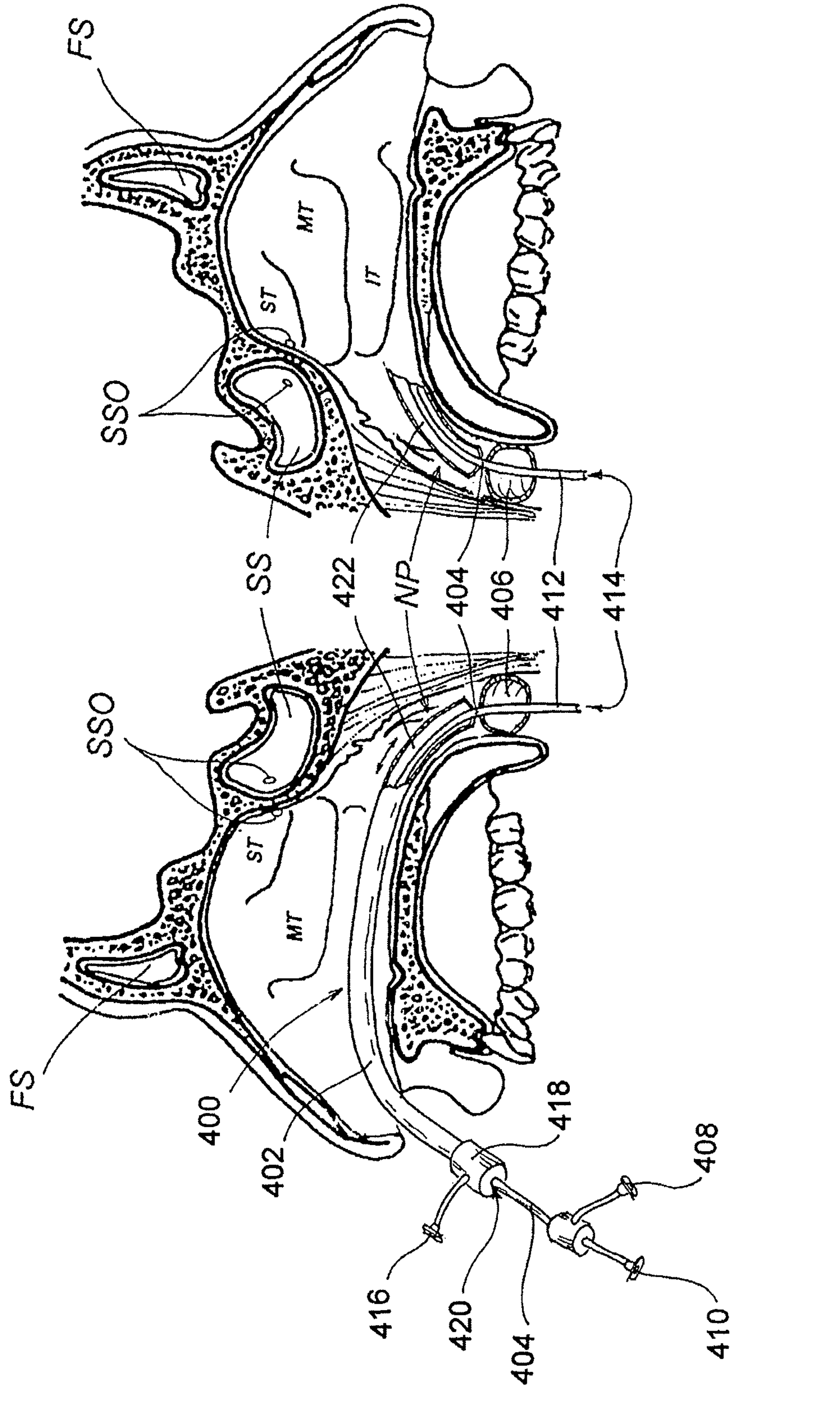
FIG. 2O is a partial sectional view of head of a human patient showing the right nasal cavity, the right side of the nasopharynx and the associated paranasal sinuses, with a posterior occluder/slidable suction device inserted through the right nasal cavity.
FIG. 2P is a partial sectional view of head of a human patient showing the left nasal cavity, the left side of the nasopharynx and the associated paranasal sinuses and showing the posterior occluder and distal portion of the slidable suction cannula of the device of FIG. 2O residing in the nasopharynx posterior to the septum and superior to the glottis.
Figures 2Q, 2R:
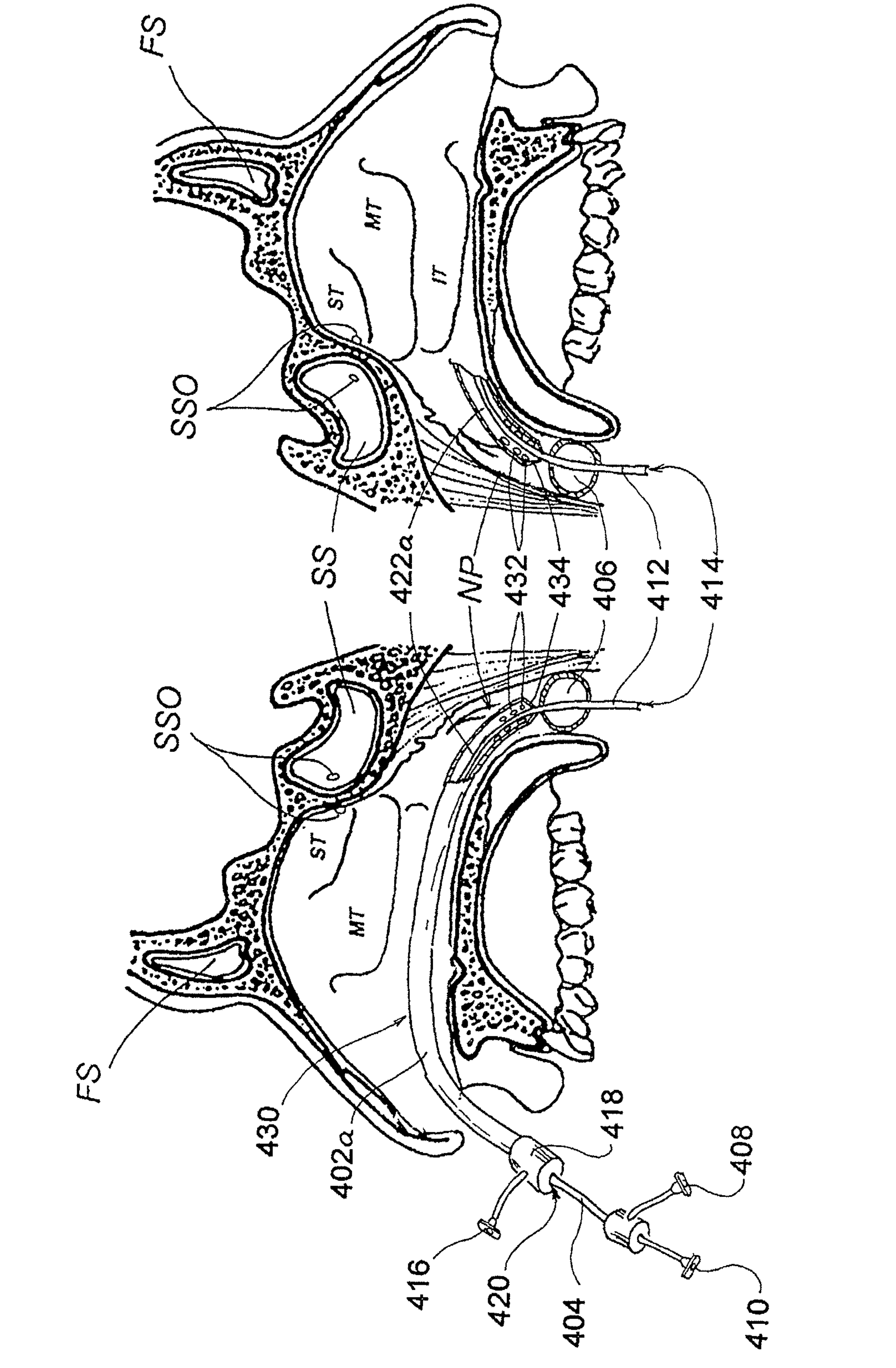
FIG. 2Q is a partial sectional view of head of a human patient showing the right nasal cavity, the right side of the nasopharynx and the associated paranasal sinuses, with another posterior occluder/tapered suction device inserted through the right nasal cavity.
FIG. 2R is a partial sectional view of head of a human patient showing the left nasal cavity, the left side of the nasopharynx and the associated paranasal sinuses and showing the posterior occluder and distal portion of the tapered suction cannula of the device of FIG. 2Q residing in the nasopharynx posterior to the septum and superior to the glottis.

FIGS. 2O-2P show an alternative posterior occluder system 400 that comprises an intranasal catheter 402 that is inserted into a nasal cavity and an occluder catheter 404 that is inserted through the intranasal catheter 402, as shown. A posterior occluder 406 is located at or near the distal end of the occluder catheter 404. In the particular embodiment shown in FIGS. 2O-2P, the occluder 406 is sized and configured to occlude the posterior choanae, nasopharynx or pharynx posterior to the nasal septum (but typically superior to the glottis). In the particular example shown, this occluder 406 comprises a balloon. However, such occluder 406 may be constructed in various alternative ways, examples of which are shown in FIGS. 3A-3K and described herebelow. In this example a balloon inflation/deflation lumen may extend from Luer connector 408, through occluder catheter 404 and to the balloon-type proximal occluder 406. A syringe or other inflation/deflation apparatus may be attached to the Luer connector 408 and used to inflate and deflate the balloon-type posterior occluder 406. A stopcock or other valve (not shown) may also be provided on the balloon inflation/deflation lumen to maintain inflation of the balloon-type posterior occluder 406, when desired. Optionally, distal tubular extension 412 may extend distally of the posterior occluder 406 and a separate lumen may extend from an optional second connector 410, through distal tubular extension 412 and through an opening 414 such that matter may also be aspirated from the area distal to the posterior occluder 406. A port body 418 is formed on the proximal end of the intranasal tube 402. An insertion port 420 extends through port body 418 into the lumen 422 of the intra nasal tube. A side suction port 416 may also be connected to the lumen 422 of the intranasal tube 402. In routine operation, the intranasal tube 402 is inserted through the nostril into one nasal cavity and advanced to a position where its distal end is within or near the posterior choanae or nasopharynx. With the posterior occluder 406 in a collapsed (e.g., deflated) configuration, the occluder catheter 404 is advanced through the lumen 422 of the intranasal catheter 402 to a position where the posterior occluder is located in the posterior choanae, nasopharynx or pharynx posterior to the nasal septum (but typically superior to the glottis). Thereafter, the posterior occluder 406 may be expanded (e.g., inflated) such that it occludes or blocks the posterior choanae, nasopharynx or pharynx posterior to the nasal septum (but typically superior to the glottis), thereby substantially preventing blood, other fluid or debris from draining into the patient's esophagus or trachea during the procedure. Thereafter, suction may be applied to suction port 416 to suction blood, other fluid or debris from the area proximal to the posterior occluder 406. During such suctioning, the intranasal tube 402 may be moved back and/or forth as indicated by arrows on FIG. 2O, while the occluder catheter 404 remains stationary. Such ability to move the intranasal catheter 402 during the suctioning process may facilitate complete removal of blood, other fluid and/or debris from the operative field.

FIGS. 2Q and 2R show a modified posterior occluder system 430 which includes the same elements and components as the posterior occluder system 400 described above, but wherein the distal end 434 of the intranasal tube 402*a* is tapered and wherein a plurality of side apertures 432 are formed in the intranasal tube 402*a* such that blood, other fluid or debris may be aspirated into the lumen 422*a* of the intranasal tube 402*a* through such side apertures 432.

B. Variations in Occluder Design and Suction Apparatus

Although the above-described examples of occluder/access devices 10, 12, 300, 400 show occluders that are in nature of inflatable balloons, it will be appreciated that these occluders are not limited to balloons and may be of various other designs and types. Further, it is to be understood that various arrangements of access and/or suction tubing/port(s) may be used to facilitate complete removal of blood, fluid or other debris from the areas adjacent to the occluder(s) and/or elsewhere in the operative field or optimal positioning of working devices within the operative field. In fact, certain occluder and/or suction-access tubing/port designs may be more desirable for certain procedures than others depending on a number of factors including the positioning of the patient's head during surgery, whether the patient will be under a general anesthetic, whether an endotracheal tube will be inserted, etc. In some cases, where a posterior occluder is positioned within the posterior choanae, nasopharynx or pharynx posterior to the nasal septum the completeness with which blood, other fluid or debris may be suctioned out of the area adjacent to that posterior occluder may depend on the shape and/or design of the occluder itself as well as the shape and location of the suction lumen(s) and port(s) through which the blood, fluid or debris is to be suctioned. Beyond optimized fluid control, the posterior occluder and/or associated access tubing may also serve as an essential guiding element for devices, and alternative shapes and trajectories may be particularly useful to access specific structures. FIGS. 3A-3K show examples of varied occluder types and variations in the arrangements of suction lumen(s) and port(s) through which the blood, fluid or debris may be suctioned from areas adjacent to the occluder or elsewhere within the operative field. The examples shown in FIGS. 3A and 3K may be incorporated into the occluder & access devices shown in FIGS. 2A-2R, when appropriate.

Figure 3A:
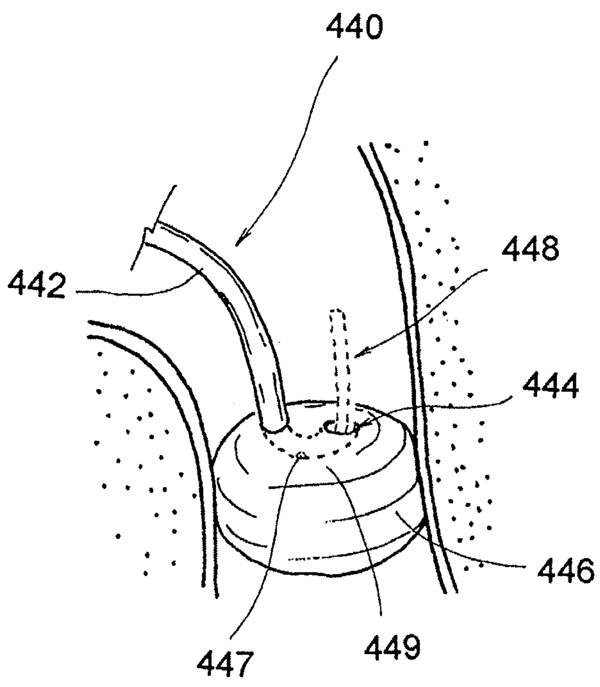
FIG. 3A is a partial perspective view of one embodiment of an occluder/suction device of the present invention positioned within an anatomical passageway.

FIG. 3A shows an occluder 446 mounted on a tube 442, wherein a generally "U" shaped curve is formed in the distal end of the tube such that a distal portion of the tube 442 passes beneath the upper surface 449 of the occluder 446 and curves upwardly such that the distal end of the tube 442 terminates in an opening 444 that is flush with the upper surface 449 of occluder 446. In this manner, any fluid that has accumulated adjacent to the upper surface 449 of occluder 446 may be suctioned into opening 444 and through tube 442. In embodiments where the occluder comprises a balloon, a balloon inflation lumen may extend through the tube and open through an opening 447 into the interior of the balloon, to permit inflation/deflation of the balloon. Optionally, a working device 448, such as a flexible catheter or elongate apparatus examples of which are shown in FIGS. 5A-5T and described herebelow, may also be advanced through the suction lumen of tube 442 and out of opening 444 as indicated on FIG. 3A.

Figure 3B:
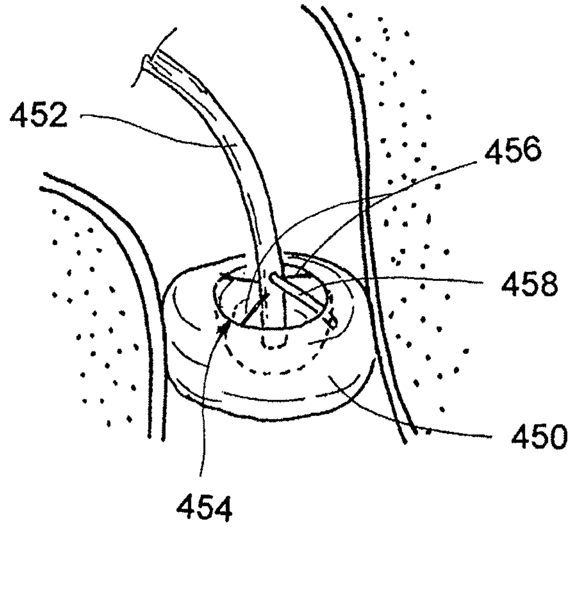
FIG. 3B is a partial perspective view of another embodiment of an occluder/suction device of the present invention positioned within an anatomical passageway.

FIG. 3B shows another alternative wherein an occluder 450 has a depression or well 454 formed in its upper surface. A tube 452 is attached to the occluder by attachment members 456 and the distal end of the tube 452 protrudes into well 454 such that any blood, fluid or debris that collects within the well 454 may be suctioned through the tube 452. In embodiments where the occluder 450 comprises a balloon, the tube 452 may incorporate a balloon inflation/deflation lumen which may extend through an inflation/deflation side tube 458 into the interior of the balloon to facilitate inflation and deflation of the balloon.

Figure 3C:
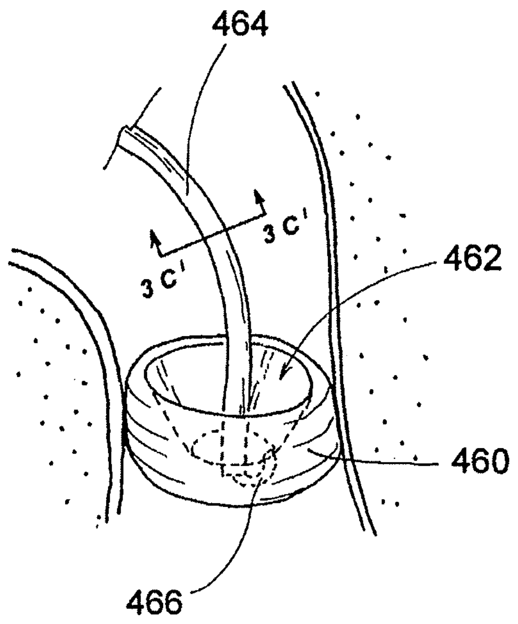
FIG. 3C is a partial perspective view of another embodiment of an occluder/suction device of the present invention positioned within an anatomical passageway.
Figure 3C:
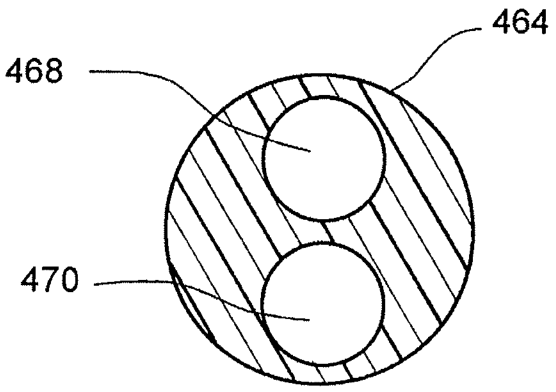

FIGS. 3C and 3C' show another alternative wherein an occluder 460 had a depression or well 462 formed in its upper surface and a tube 464 is attached to the occluder 460, as shown. A lumen of the tube 464 is in communication with the area adjacent the floor of the well to facilitate suctioning of blood, fluid or debris that collects within the well. In embodiments where the occluder 460 comprises a balloon, the tube 464 may incorporate a suction lumen 468 and a balloon inflation/deflation lumen 470. A small curved (e.g., generally "U" shaped) suction tube 466 may be connected in a sealed connection to the distal end of suction lumen 468 and the interior of the well 462 such that blood, other fluid or debris may be suctioned from the well 462, through suction tube 466 and through suction lumen 468.

Figure 3D:
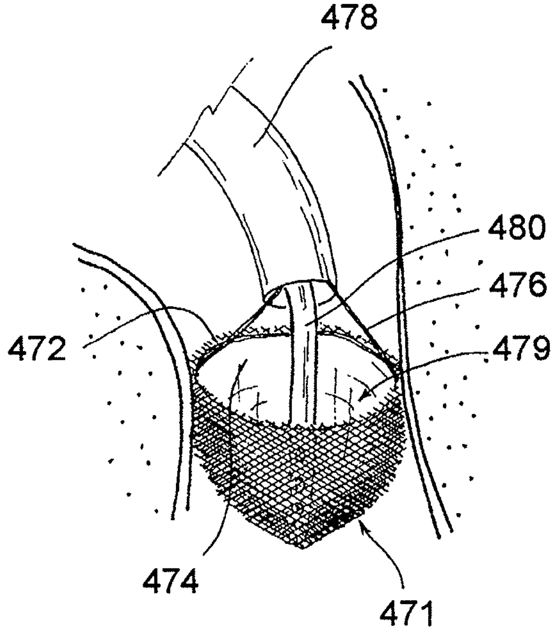
FIG. 3D is a partial perspective view of yet another embodiment of an occluder/suction device of the present invention positioned within an anatomical passageway.

FIG. 3D shows a concave occluder 471 that comprises a self expanding concave structure 472 such as a basket formed of a superelastic or resilient mesh material (e.g., nickel titanium alloy wire mesh). The expanding concave structure 472 is covered by a fluid impermeable flexible covering 474 such as a skin formed of flexible polymer (e.g., expanded polytetrafluoroethylene, polyurethane, polyethylene teraphthalate, etc.). When fully expanded the concave occluder 471 occludes the body lumen in which it is positioned (e.g., the nasal cavity, posterior choanae, nasopharynx, pharynx, etc.) and forms a concave well 479. A tube 480 extends into the well 479 of the concave occluder 471 and may be used to suction blood, fluid or debris from the well 479. The occluder 471 may be advanced from and withdrawn into a delivery catheter 478. Struts 472 may connect the concave occluder 471 to a delivery member (not shown) within the delivery catheter 478, such delivery member being advanceable to push the occluder 471 out of the delivery catheter 478 and retractable to withdraw the occluder 471 into the delivery catheter 478. When inside the delivery catheter, the occluder 471 may be in a collapsed configuration but when expelled out of the delivery catheter the occluder will resiliently spring or self-expand to its expanded concave configuration, as shown in FIG. 3D. The suction catheter 480 may advance from and/or retract into the delivery catheter 478 concurrently with, or separately from, the occluder 471.

Figure 3E:
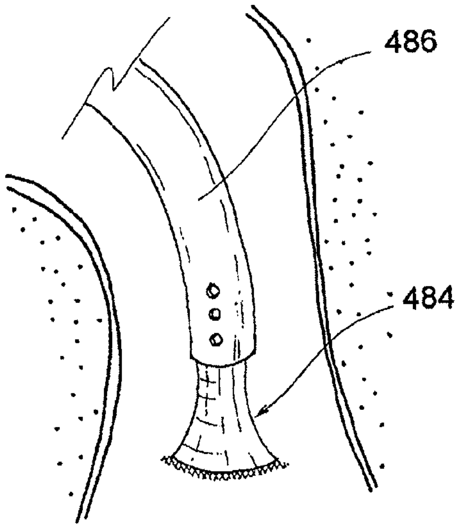
FIGS. 3E', 3E" and 3E'" are partial perspective views of still another embodiment of an occluder/suction device of the present invention showing various steps in a process by which the occluder/suction device is positioned within an anatomical passageway.
Figure 3E:
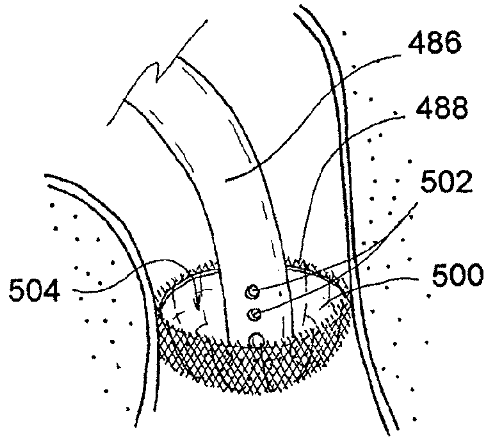
Figure 3E:
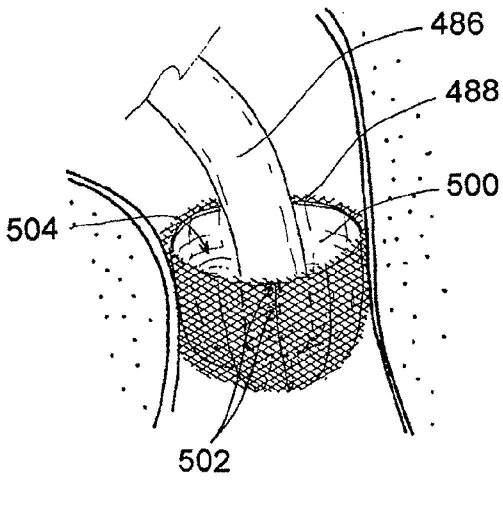

FIGS. 3E'-3E''' show yet another occluder/suction arrangement wherein the occluder 484 comprises an everting tubular member that is advanceable from a delivery/suction catheter 486. The everting tubular member comprises a frame 488 that is covered with a covering 500. Initially the everting tubular member is in a substantially cylindrical configuration within the lumen of the delivery/suction catheter 486. The frame may be a resilient or superelastic material that is biased to the everted shape shown in FIG. 3E'''. Such frame 488 may be formed of mesh material (e.g., nickel titanium alloy wire mesh). The covering 500 may be formed of flexible polymer (e.g., expanded polytetrafluoroethylene, polyurethane, polyethylene teraphthalate, etc.) In operation, the delivery/suction catheter 486 is advanced to the position where it is desired to place the occluder 484. Then, the everting tube is advanced from the distal end opening of the delivery/suction tube 486, as shown in FIGS. 3E' and 3E''. As it advances out of the catheter 486, the everting tube member assumes its everted configuration, forming a concave occluder 484 as shown in FIG. 3E'''. The occluder 484, when fully everted, occludes the body lumen in which it is positioned (e.g., the nasal cavity, posterior choanae, nasopharynx, pharynx, etc.) and creates a concave well 504. The delivery/suction catheter 486 may be advanced into the concave well 504 such that any blood, fluid or debris that collects within concave well 504 may be suctioned through suction ports 502 and through the distal end of the delivery/suction catheter 486.

Figure 3F:
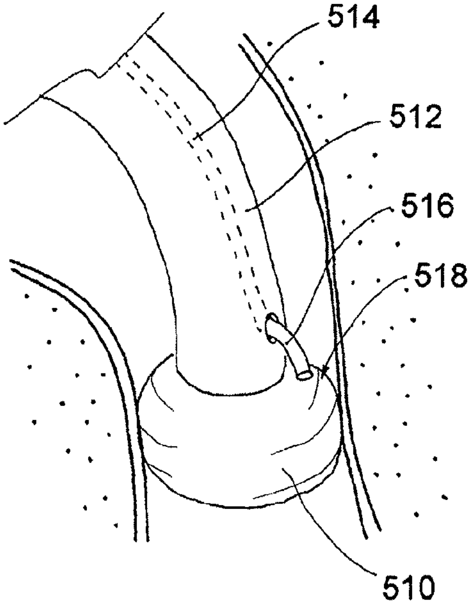
FIG. 3F is a partial perspective view of still another embodiment of an occluder/suction device of the present invention positioned within an anatomical passageway.
Figure 3F:
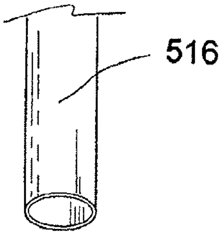
Figure 3F:
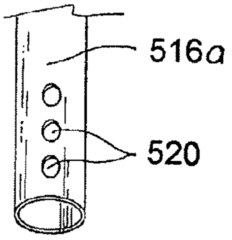
Figure 3F:
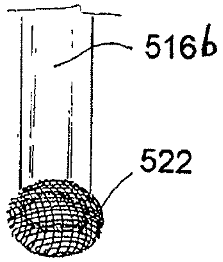

FIG. 3F-3F''' show another embodiment wherein an occluder 510 is positioned on the end of a tube 512. The occluder 510 has an arched upper surface such that a generally "V" shaped annular collection space 518 is created in the region of the coaptation between the occluder 510 and the adjacent wall of the body lumen in which it is positioned (e.g., a nasal cavity, posterior choanae, nasopharynx, pharynx, etc.). A suction tube 516 extends from tube 512 into the annular collection space 518 and blood, other fluid or debris that collects in the annular collection space 518 may be suctioned through suction tube 516 and through a lumen of tube 512, thereby providing for maintenance of a substantially dry environment adjacent to the upper surface of the occluder 510. The occluder 510 may comprise a balloon or any other suitable occlusion member as described herein or known in the art. As shown in FIGS. 3F'-3F''' the suction tube 516 may comprise a simple tube having an open distal end or, alternatively, the device may incorporate a suction tube 516*a* that has a plurality of side apertures 520 formed near its distal end and/or a suction tube 516 that has a guard member 522, such as a screen, formed over its suction ports or openings to deter solid matter (e.g., blood clots or other debris) from clogging the suction ports or openings.

Figure 3G:
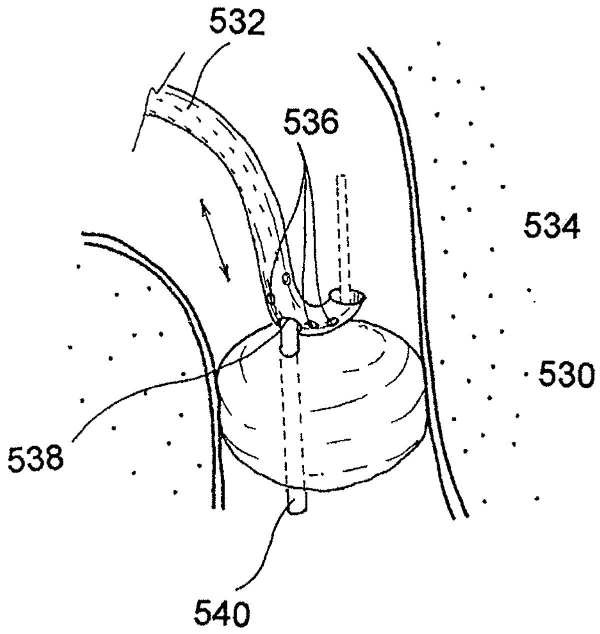
FIG. 3G is a partial perspective view of still another embodiment of an occluder/suction device of the present invention positioned within an anatomical passageway.

FIG. 3G shows an occluder 530 attached to a tube 532 that has a curved (e.g., generally "U" shaped) distal end that does not protrude into the interior of the occluder. Suction apertures 536 are formed in the distal portion of the tube 532 to permit blood, fluid or debris that collects adjacent to the upper surface of the occluder 530 to be suctioned through the tube 532. In embodiments where the occluder is a balloon a balloon/inflation lumen may extend through tube 532 and a small balloon inflation tube 538 may extend into the interior of the balloon to permit the balloon to be inflated and deflated. Optionally, in some embodiments, a separate tube 540 may extend through tube 532 and trough occluder 530 to provide access to the area distal to the occluder 530 for purposes of suctioning, introduction of instruments, or other purposes.

Figure 3H:
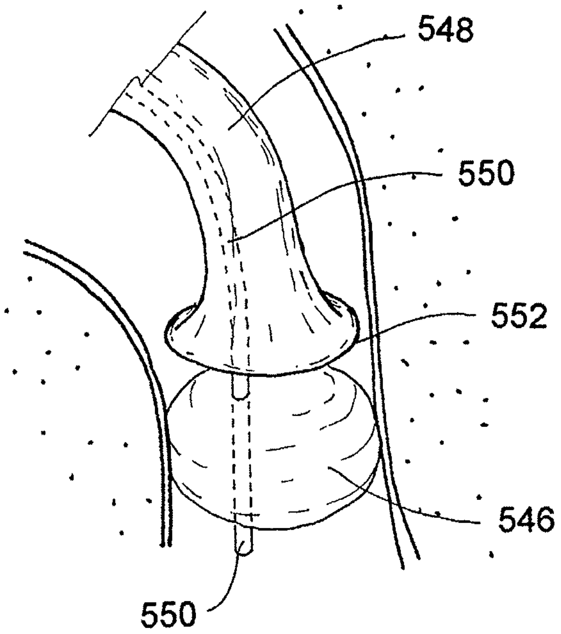
FIG. 3H is a partial perspective view of still another embodiment of an occluder/suction device of the present invention positioned within an anatomical passageway.

FIG. 3H shows another embodiment wherein the occluder 546 is connected to a tube or elongate member 550 and a suction tube 548 having an expanded (e.g., trumpet shaped) distal end is useable to suction blood, fluid or debris from the area adjacent to the upper surface of the occluder. As can be seen from FIG. 3H, where the upper surface of the occluder is arched and annular collection space may be created around the perimeter of the occluder 546 where the occluder 546 coapts with the wall of the anatomical structure in which it is positioned (e.g., a nasal cavity, posterior choanae, nasopharynx, pharynx, etc.) and the expanded end 552 of the suction tube 548 may be sized and shaped to receive the arched upper surface of the occluder 546 and to suction any blood, fluid or debris from that annular collection space. In embodiments where the occluder is a balloon a balloon/inflation lumen may extend through tube 548 and a small balloon inflation tube may extend into the interior of the balloon to permit the balloon to be inflated and deflated. Optionally, in some embodiments, a separate tube 550 may extend through tube 548 and through occluder 546 to provide access to the area distal to the occluder 546 for purposes of suctioning, introduction of instruments or fluid injectors, or other purposes.

Figure 3I:
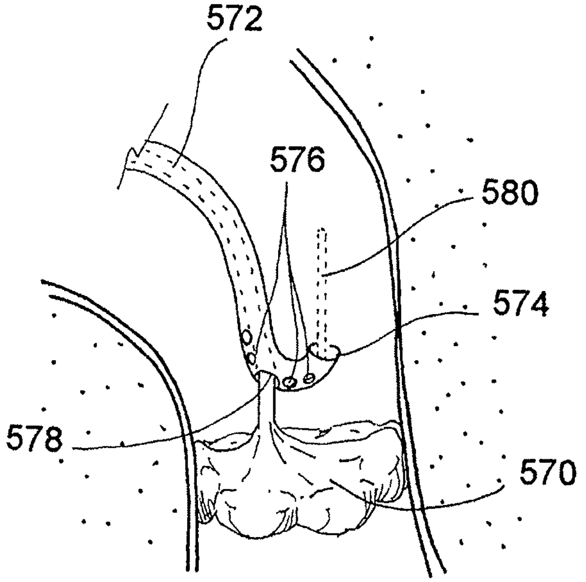
FIG. 3I is a partial perspective view of still another embodiment of an occluder/suction device of the present invention positioned within an anatomical passageway.

FIG. 3I shows an embodiment wherein the occluder 570 comprises a mass of absorbent material such as a tampon (e.g., cotton, gauze, hydrogel or other material or composite of materials that will absorb fluid and occlude the desired body lumen). In the particular example shown, the occluder is advanced out of an aperture 578 formed in a tube 572 that has a curved (e.g., generally "U" shaped) tip. Suction apertures 576 are formed in the distal portion of the tube 572 to permit blood, fluid or debris that collects adjacent to the upper surface of the occluder 570 to be suctioned through the tube 572. After the procedure is complete or the occlusion is no longer required, the tube 572 and fluid-soaked occluder 570 may be withdrawn from the body without retraction of the occluder 570 into the tube 572. Optionally, a distal end opening 574 may be formed in tube 572 and such distal end opening may be connected to the same lumen as openings 576 or a separate lumen to the optional distal end opening 574 to be used for suctioning, irrigation or introduction of a working device 580 such those shown in FIGS. 5A-5Y''''' and described herebelow.

Figure 3J:
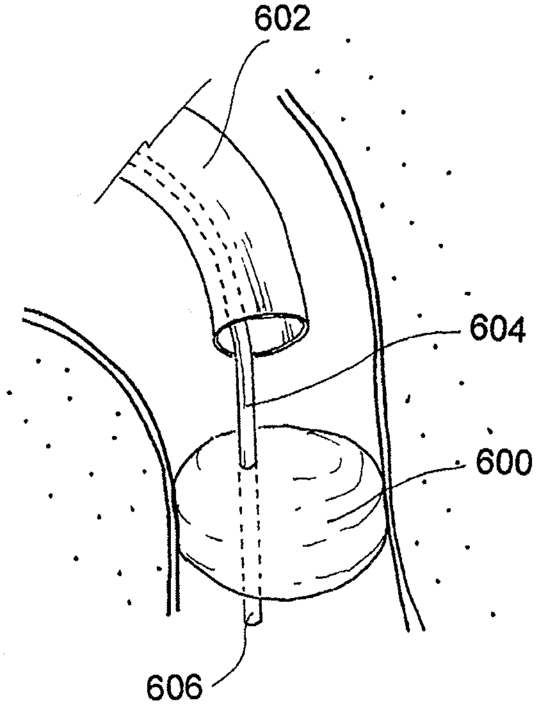
FIG. 3J is a partial perspective view of still another embodiment of an occluder/suction device of the present invention positioned within an anatomical passageway.

FIG. 3J shows an occluder embodiment similar to that of the device shown in FIGS. 2O and 2P and described hereabove. In this embodiment, an occluder 600 is attached to a tube or elongate member 604 and a suction tube 602 is movable back and forth over the tube or elongate member 604 to suction blood, fluid or debris from the area adjacent to the upper surface of the occluder 600 or elsewhere in the body lumen in which the occluder 600 is positioned. In embodiments where the occluder 600 is a balloon, a balloon/inflation lumen may extend through tube or elongate member 604 and into the balloon to permit the balloon to be inflated and deflated. Optionally, in some embodiments, a separate tube 606 may extend trough tube or elongate member 604 and through occluder 600 to provide access to the area distal to the occluder 600 for purposes of suctioning, introduction of instruments, or other purposes.

Figure 3K:
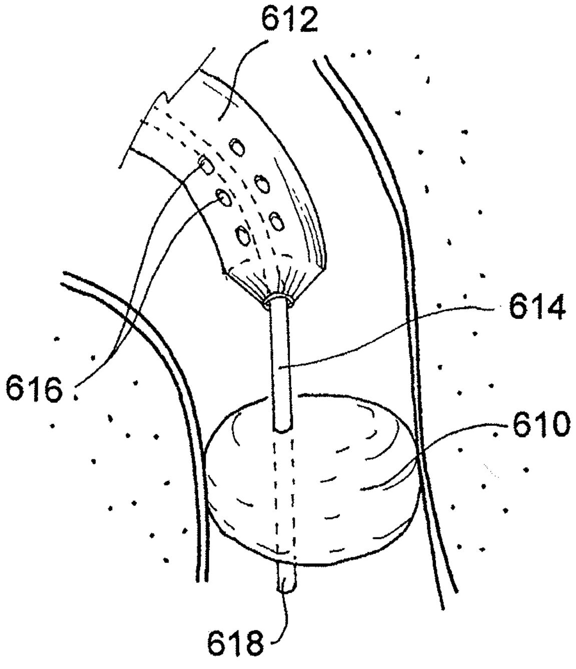
FIG. 3K is a partial perspective view of still another embodiment of an occluder/suction device of the present invention positioned within an anatomical passageway.

FIG. 3K shows an occluder embodiment similar to that incorporated into the device shown in FIGS. 2Q and 2R and described hereabove. In this embodiment, an occluder 610 is attached to a tube or elongate member 614 and a tapered suction tube 612 having one or more suction apertures 616 formed therein is movable back and forth over the tube or elongate member 614 to suction blood, fluid or debris from the area adjacent to the upper surface of the occluder 610 or elsewhere in the body lumen in which the occluder 600 is positioned. Of course, irrigation solution or other fluids may also be delivered through such apertures 616 or through a separate irrigation/infusion lumen that opens through separate irrigation/infusion aperture(s) (not shown). In embodiments where the occluder 610 is a balloon, a balloon/inflation lumen may extend through tube or elongate member 614 and into the balloon to permit the balloon to be inflated and deflated. Optionally, in some embodiments, a separate tube 618 may extend trough tube or elongate member 614 and through occluder 610 to provide access to the area distal to the occluder 610 for purposes of suctioning, introduction of instruments, or other purposes.

Figure 3L:
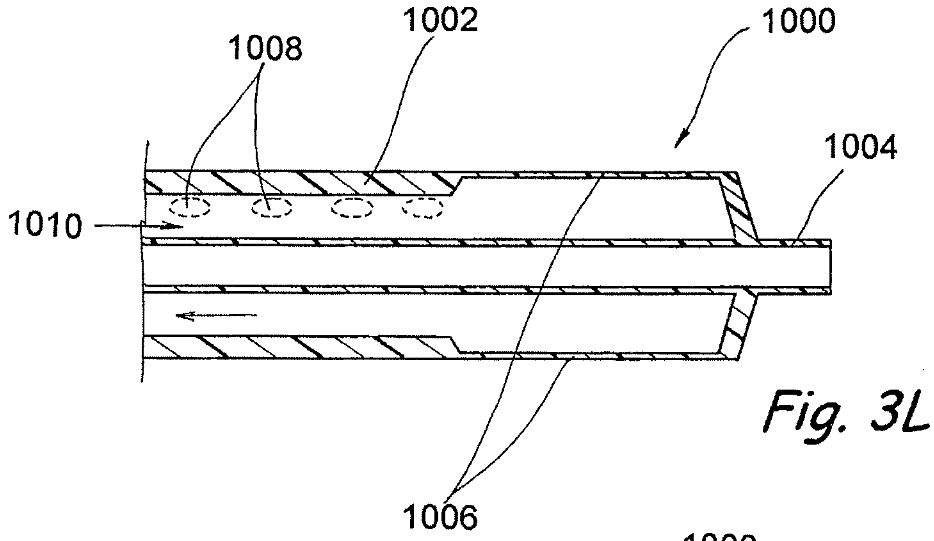
FIGS. 3L' and 3L" show partial longitudinal sectional views of another occluder/suction device of the present invention.
Figure 3L:
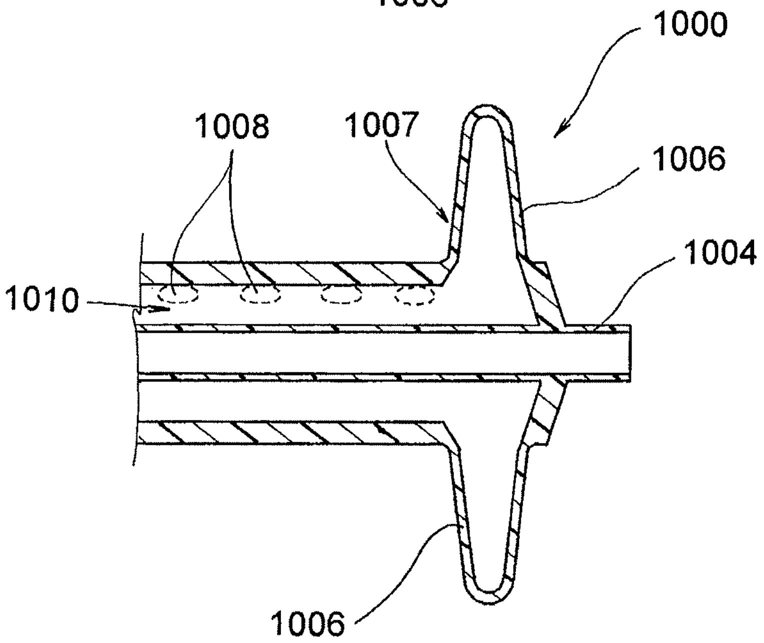

FIGS. 3L'-3L'' show yet another occluder/tubing device 1000 comprising an outer tube 1002 and an inner tube 1004 disposed coaxially within the outer tube 1002. An outwardly bendable region 1006 is formed in the wall of the outer tube 1002 near its distal end. The distal end of the outer tube 1002 is affixed to the inner tube 1004. A passageway 1010 extends between the outer tube 1002 and inner tube 1004 and openings 1008 are formed in the wall of the outer tube 1002. In routine operation, this device 1000 is initially disposed in the configuration shown in FIG. 3L' and is inserted into the desired passageway. Thereafter, the inner tube 1004 is pulled in the proximal direction while the outer tube 1002 is held stationary, thereby causing the outwardly bendable region 1006 to protrude outwardly as shown in FIG. 3L'' and resulting in occlusion of the body lumen in which the distal portion of the device 1000 is positioned. Suction may be applied to passageway 1010 to remove blood, fluid or other debris from the area adjacent to the upper surface of 1007 of the outwardly protruding bendable region 1006. In this regard, the openings 1008 may be formed close to and/or even in the upper surface 1007 of the outwardly protruding bendable region 1006.

Figure 3M:
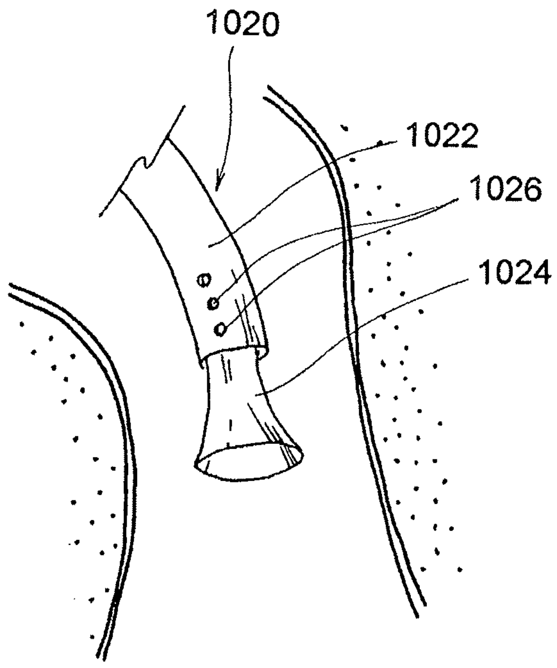
FIGS. 3M' and 3M" show partial perspective views of another occluder/suction device of the present invention positioned within an anatomical passageway.
Figure 3M:
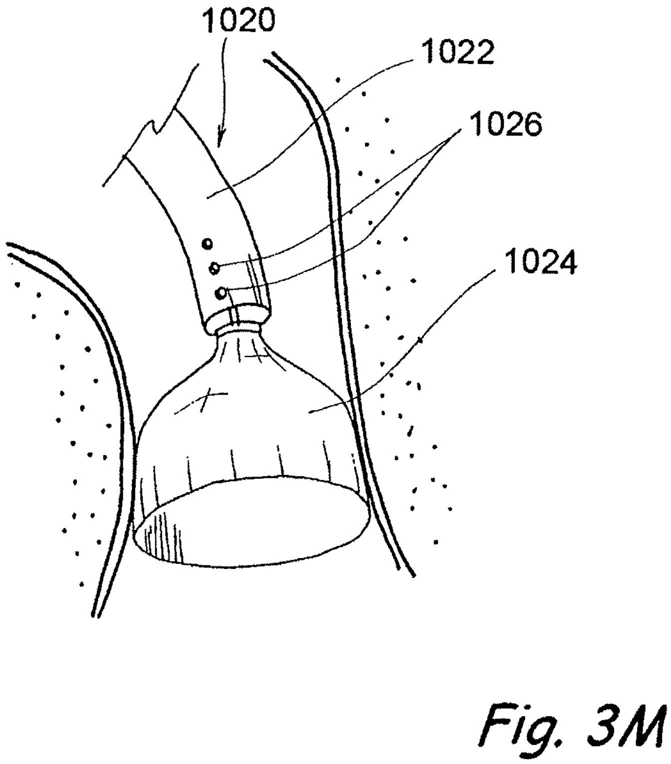

FIGS. 3M' and 3M'' show another occluder/tubing device 1020 comprising an outer tube 1022 an inner tube 1024. The inner tube 1024 is advanceable out of the distal end of the outer tube 1022 and a distal portion of the inner tube 1024 expands as it emerges from the inner tube, thereby forming an occluder that occludes the body lumen or passageway in which it is positioned, as shown in FIG. 3M''. Blood, other fluid or debris may be suctioned from the area adjacent to the upper surface of the occluder through the open distal end of the outer tube 1022 and/or through optional side apertures 1026.

Figure 4:
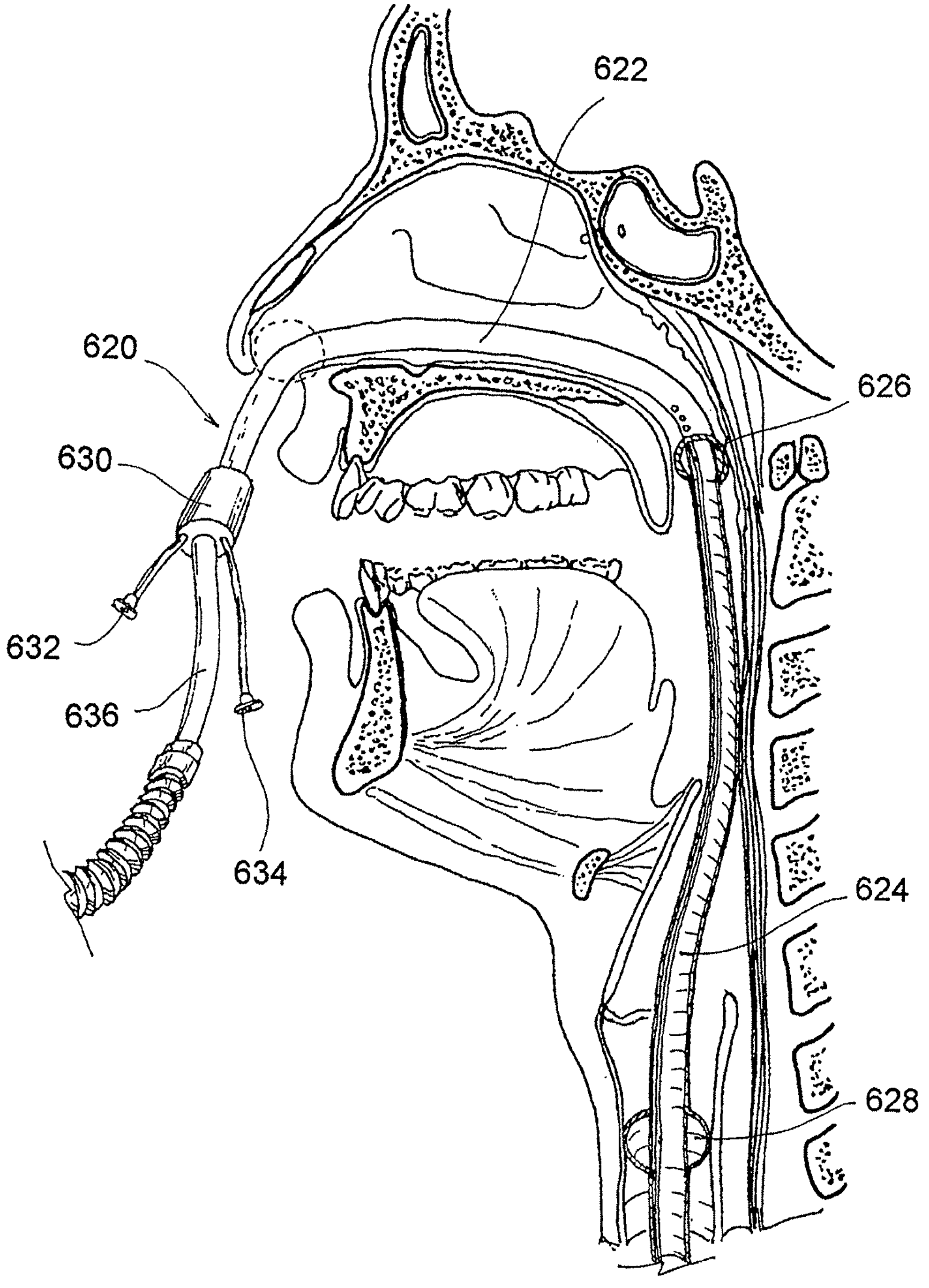
FIG. 4 is a longitudinal sectional view of the oropharynx and anterior neck of a human patient having a nasopharyngeal occluder/endotracheal tube device of the present invention inserted through the right nasal cavity and into the trachea.

FIG. 4 shows a nasopharyngeal occluder/endotracheal tube device 620 of the present invention inserted through the right nasal cavity and into the trachea. This device 620 comprises a curved tube 622 having a posterior occluder 626 positioned at or near the distal end of the tube 622 and, optionally an anterior occluder (shown in dotted lines on FIG. 4) formed near the proximal end of the tube 622. An endotracheal tube 624 extends through curved tube 622, through the posterior occluder and into the patient's trachea. Optionally, a cuff 628 may be formed on endotracheal tube 624 to provide a second substantially fluid tight seal within the patient's trachea, inferior to the glottis. A hub 630 is formed on the proximal end of tube 622. A ventilator tube 634 extends from the hub and is connected to endotracheal tube 624 and is attachable to a ventilator, anesthesia machine, t-tube, Ambu-bag, etc. In embodiments where the posterior occluder 626 is a balloon, a posterior occluder inflation/deflation connector 632 extends from hub 630 and is connected to an inflation/deflation lumen that extends through tube 622 for inflation/deflation of the posterior occluder 626. A cuff inflation/deflation connector 634 may also extend from hub 630 and through the endotracheal tube 624 for inflation/deflation of the endotracheal tube cuff 628. Optionally, suction and/or device insertion ports may also be formed in hub 630, as described above in connection with other occluder/access devices. In routine operation, this device 620 is inserted to a position where the posterior occluder 626 occludes the posterior choanae, nasopharynx or pharynx posterior to the nasal septum (but typically superior to the glottis) and the endotracheal tube 624 extends into the patient's trachea with the optional cuff positioned in the trachea inferior to the glottis.

C. Working Devices for Delivering Substances or for Cutting, Ablating, Remodeling or Expanding Bone or Soft Tissue The present invention provides a variety of apparatus that may be inserted into the nasal cavity, paranasal sinus, nasopharynx or middle ear to perform diagnostic or therapeutic procedures. These devices may be delivered through or incorporated into flexible catheters or flexible rod-like shafts. Such flexible construction allows these devices to be delivered and positioned to perform the desired diagnostic or therapeutic procedures with minimal trauma to other tissues, as can result from the insertion of rigid scopes and rigid instruments in accordance with the methodology of the prior art. It is within the scope of this approach that these devices may be partially flexible or have rigid portions and flexible portions to facilitate their control and guidance to the appropriate region. Further, they may be used in conjunction or combination with other standard rigid apparatus (scopes, etc.) during some part of the procedure, if desired.

Also, in some but not necessarily all procedures, these working devices (and/or the catheters used to deliver them) may be inserted through lumens of the occluder & access devices 10, 12, 300, 301, 400, 430, etc. as shown in FIGS. 2A-2R and described above. As stated earlier, it may also be desirable to focus the access and occlusion to an even smaller territory, through stand-alone guide catheters or subselective guide catheters with or without balloons or other occluders.

Optionally, any of the working devices and guide catheters described herein may be configured to receive or be advanced over a guidewire unless to do so would render the device inoperable for its intended purpose. Some of the specific examples described herein include guidewires, but it is to be appreciated that the use of guidewires and the incorporation of guidewire lumens is not limited to only the specific examples in which guidewires or guidewire lumens are shown. The guidewires used in this invention may be constructed and coated as is common in the art of cardiology. This may include the use of coils, tapered or non-tapered core wires, radiopaque tips and/or entire lengths, shaping ribbons, variations of stiffness, PTFE, silicone, hydrophilic coatings, polymer coatings, etc. For the scope of this inventions, these wires may possess dimensions of length between 5 and 75 cm and outer diameter between 0.005" and 0.050".

Also, some of the working devices shown in FIGS. 5A-5Y""" and described herein incorporate assemblies, components or mechanisms (e.g., rotating cutters, radiofrequency electrodes, electrocautery devices, receptacles for capturing matter, cryosurgical apparatus, balloons, stents, radioactive or substance-eluting coatings, snares, electro-anatomical mapping and guidance, optical fibers, lenses and other endoscope apparatus, seals, hemostatic valves, etc. The designs and constructions of such components and assemblies are will known in the art. Non-limiting examples of some such designs and constructions are set forth in U.S. Pat. No. 5,722,984 (Fischell et al.), U.S. Pat. No. 5,775,327 (Randolph et al.), U.S. Pat. No. 5,685,838 (Peters, et al.), U.S. Pat. No. 6,013,019 (Fischell et al.), U.S. Pat. No. 5,356,418 (Shturman), U.S. Pat. No. 5,634,908 (Loomas), U.S. Pat. No. 5,255,679 (Imran), U.S. Pat. No. 6,048,299 (Hoffman), U.S. Pat. No. 6,585,794 (Wright et al.), U.S. Pat. No. 6,503,185 (Waksman), U.S. Pat. No. 6,669,689 (Lehmann et al.), U.S. Pat. No. 6,638,233 (Corvi et al.), U.S. Pat. No. 5,026,384 (Farr et al.), U.S. Pat. No. 4,669,469 (Gifford et al.), U.S. Pat. No. 6,685,648 (Flaherty et al.), U.S. Pat. No. 5,250,059 (Andreas et al.), U.S. Pat. No. 4,708,834 (Tsuno), U.S. Pat. No. 5,171,233 (Amplatz), U.S. Pat. No. 6,468,297 (Williams et al.) and U.S. Pat. No. 4,748,869 (Wardle).

As shown in the examples of FIGS. 5A-5Y""" these working devices include guide catheters, substance delivery catheters, scopes, injectors, cutters, bone breaking apparatus, balloons and other dilators, laser/thermal delivery devices, braces, implants, stents, snares, biopsy tools, forceps, etc.

FIG. 5A shows a side suction and/or cutting catheter 70 comprising a flexible catheter body 72 having a side opening 74. The catheter 72 is advanced into a passageway such as a nostril, nasal cavity, meatus, ostium, interior of a sinus, etc. and positioned so that the opening 74 is adjacent to matter (e.g., a polyp, lesion, piece of debris, tissue, blood clot, etc.) that is to be removed. Suction may be applied through a lumen of the catheter 72 to suction the matter through the opening 74 and into the catheter 72. In some cases, a cutter such as a rotating cutter, linear slicer, pincher, laser beam, electrosurgical cutter, etc. may be incorporated into the catheter 72 to assist in severing or ablating tissue or other matter that has been positioned in the side opening 74. This catheter may incorporate a deflectable tip or a curved distal end which may force the opening of the catheter against the tissue of interest. Further, this device 70 may have an optional stabilizing balloon (similar to that shown in FIG. 5M and described herebelow) incorporated on one side of the catheter 72 to press it against the tissue of interest and may also contain one or more on-board imaging modalities such as ultrasound, fiber or digital optics, OCT, RF or electro-magnetic sensors or emitters, etc.

FIG. 5 B shows an injector catheter 76 that comprises a flexible catheter shaft 78 having one or more injector(s) 80 that are advanceable into tissue or other matter that is located in or on the wall of the body lumen in which the catheter 78 is positioned. The catheter 78 is advanced, with the injector(s) retracted into the catheter body, through a passageway such as a nostril, nasal cavity, meatus, ostium, interior of a sinus, etc. and positioned adjacent the area to which a diagnostic or therapeutic substance is to be injected. Thereafter, the injector(s) are advanced into the adjacent tissue or matter and the desired substance is injected. Energy, such as laser, RF, thermal or other energy may be delivered through these injectors 80 or energy emitting implants (such as gamma or beta radioactive seeds) may also be delivered through these injectors 80, either alone or in combination with a fluid carrier or other substance such as a diagnostic or therapeutic substance (as defined herein). It will be noted that this device 76 as well as other working devices and methods of the present invention (including the various implantable devices described herein) are useable to deliver diagnostic or therapeutic substances. The term "diagnostic or therapeutic substance" as used herein is to be broadly construed to include any feasible drugs, prodrugs, proteins, gene therapy preparations, cells, diagnostic agents, contrast or imaging agents, biologicals, etc. For example, in some applications where it is desired to treat or prevent a microbial infection, the substance delivered may comprise pharmaceutically acceptable salt or dosage form of an antimicrobial agent (e.g., antibiotic, antiviral, anti-paracytic, antifungal, etc.).

Some nonlimiting examples of antimicrobial agents that may be used in this invention include acyclovir, amantadine, aminoglycosides (e.g., amikacin, gentamicin and tobramycin), amoxicillin, amoxicillin/Clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as “plantibodies;” agents which change the condition of the tissue to make it hostile to the pathogen (such as substances which alter mucosal pH (e.g., Buffer Gel and Acidform) or non-pathogenic or “friendly” bacteria or other microbes that cause the production of hydrogen peroxide or other substances that kill or inhibit the growth of pathogenic microbes (e.g., lactobacillus). As may be applied to any of the substances listed previously or below, these substances may be combined with any one or more drug-releasing devices or molecular constructs such as polymers, collagen, gels, implantable osmotic pump devices, etc. to permit their release over an extended period of time once deposited. Further, these substances may also be combined with any of the implantable structural devices described below (stents, expanders, etc.) to reduce infection, encrustation, or encapsulation of the implant itself, or to allow the drug to be deposited in the optimal location mucosally, sub-mucosally or into the bone. Examples of implantable substance delivery devices useable in this invention include those shown in FIGS. 5Y'-5Y''''' and described herebelow.

Additionally or alternatively, in some applications where it is desired to treat or prevent inflammation the substances delivered in this invention may include various steroids. For example, corticosteroids that have previously administered by intranasal administration may be used, such as beclomethasone (Vancenase® or Beconase®), flunisolide (Nasalide®), fluticasone (Flonase®), triamcinolone (Nasacort®) and mometasone (Nasonex®). Also, other steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednasone, dexamethasone and methylprednisolone, Additionally or alternatively, in some applications, such as those where it is desired to treat or prevent an allergic or immune response, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor).

Additionally or alternatively, in some applications, such as those where it is desired to shrink mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine (Mucomyst™, Mucosil™) and guaifenesin.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chrom®) and nedocromil.

Additionally or alternatively, in some applications such as those where it is desired to prevent or inhibit the effect of histamine, the substances delivered in this invention may include various antihistamines such as azelastine (e.g., Astylin®), diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting or containing bone degrading cells such as osteoclasts. Other examples would include various enzymes of material that may soften or break down components of bone or cartilage such as collagenase (CGN), trypsin, trypsin/EDTA, hyaluronidase, and tosyllysylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anticolinergic agents that tend to dry up nasal secretions such as ipratropium (Atrovent Nasal®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired.

Additionally or alternatively to being combined with a device and/or a substance releasing modality, it may be ideal to position the device in a specific location upstream in the mucous flow path (i.e. frontal sinus or ethmoid cells). This could allow the deposition of fewer drug releasing devices, and permit the "bathing" of all the downstream tissues with the desired drug. This utilization of mucous as a carrier for the drug may be ideal, especially since the concentrations for the drug may be highest in regions where the mucous is retained; whereas non-diseased regions with good mucouse flow will be less affected by the drug. This could be particularly useful in chronic sinusitis, or tumors where bringing the concentration of drug higher at those specific sites may have greater therapeutic benefit. In all such cases, local delivery will permit these drugs to have much less systemic impact. Further, it may be ideal to configure the composition of the drug or delivery system such that it maintains a loose affinity to the mucous permitting it to distribute evenly in the flow. Also, in some applications, rather than a drug, a solute such as a salt or other mucous soluble material may be positioned at a location whereby mucous will contact the substance and a quantity of the substance will become dissolved in the mucous thereby changing some property (e.g., pH, osmolarity, etc) of the mucous. In some cases, this technique may be used to render the mucous hyperosmolar so that the flowing mucous will draw water from polyps, edematous mucosal tissue, etc. thereby providing a desiccating therapeutic effect.

Additionally or alternatively to substances directed towards local delivery to affect changes within the sinus cavity, the nasal cavities provide unique access to the olfactory system and thus the brain. Any of the devices and methods described herein may also be used to deliver substances to the brain or alter the functioning of the olfactory system. Such examples include, the delivery of energy or the deposition of devices and/or substances and/or substance delivering implant(s) to occlude or alter olfactory perception, to suppress appetite or otherwise treat obesity, epilepsy (e.g., barbiturates such as phenobarbital or mephoobarbital; iminostilbenes such as carbamazepine and oxcarbazepine; succinimides such as ethylsuximide; valproic acid; benzodiazepines such as clonazepam, clorazepate, diazepam and lorazepam, gabapentin, lamotrigine, acetazolamide, felbamate, levetiraceam, tiagabine, topiramate, zonisamide, etc.), personality or mental disorders (e.g., antidepressants, anti-anxiety agents, antipsychotics, etc.), chronic pain, Parkinson's disease (e.g., dopamine receptor agonists such as bromocriptine, pergolide, ropinitrol and pramipexole; dopamine precursors such as levodopa; COMT inhibitors such as tolcapone and entacapone; selegiline; muscarinic receptor antagonists such as trihexyphenidyl, benztropine and diphenhydramine) and Alzheimer's, Huntington's Disease or other dementias, disorders of cognition or chronic degenerative diseases (e.g. tacrine, donepezil, rivastigmine, galantamine, fluoxetine, carbamazepine, clozapine, clonazepam and proteins or genetic therapies that inhibit the formation of beta-amyloid plaques), etc.

Figure 5C:
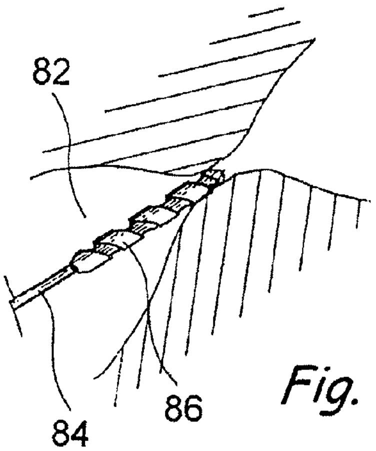
FIG. 5C is a partial perspective view of a drill (e.g., a tissue drill, bone drill, or trephine device) being used in accordance with the present invention.

FIG. 5C shows a device 82 that comprises a rotating shaft 84 having a drill, auger or burr 86 that is useable to drill, bore, grind or cut through tissue, bone, cartilage or other matter. This device 82 may deployed as shown or, alternatively, the device 82 may be inserted through a small mucosal incision to preserve the overlying mucosal lining while removing or boring into the bone or cartilage below the mucosal lining.

Figure 5D:
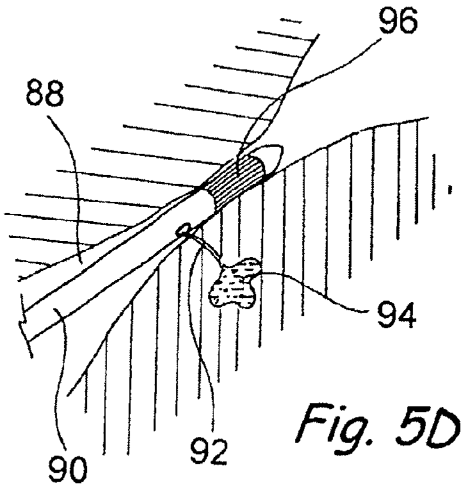
FIG. 5D is a partial perspective view of a catheter having a laterally deployed needle or tube for delivering a substance or apparatus to a target location and an optional on-board imaging or guidance apparatus, being used in accordance with the present invention.

FIG. 5D shows a guided injector catheter device 88 for delivering a diagnostic or therapeutic substance as defined above. This device 88 comprises a flexible catheter 90 having an imaging apparatus 96 thereon and an injector 92 that is advanceable from and retractable into the catheter 90. The imaging apparatus 96 is useable to image the target location 94 at which the substance is to be deposited and to enable orientation of the catheter 88 such that, when the injector 92 is advanced from the catheter 88, the injector 92 will travel to the desired target location 94. Examples of such catheter 88 are described in U.S. Pat. No. 6,195,225 (Makower), U.S. Pat. No. 6,544,230 (Flaherty et al.), U.S. Pat. No. 6,375,615 (Flaherty et al.), U.S. Pat. No. 6,302,875 (Makower et al), U.S. Pat. No. 6,190,353 (Makower et al.) and U.S. Pat. No. 6,685,648 (Flaherty et al.), the entireties of which are expressly incorporated herein by reference.

Figure 5E:
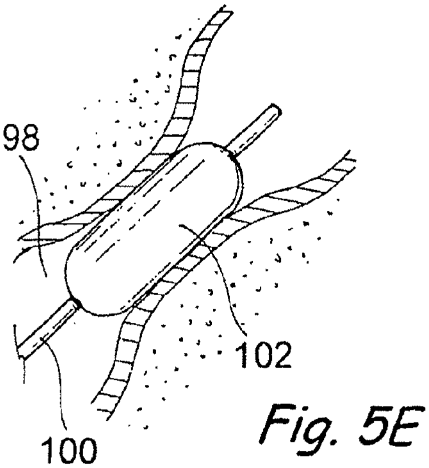
FIG. 5E is a partial perspective view of a balloon catheter being used in accordance with the present invention.

FIG. 5E shows a balloon catheter device 98 comprising a flexible catheter 100 having a balloon 102 thereon. The catheter device 98 is advanced, with balloon 102 deflated, into a passageway such as a nostril, nasal cavity, meatus, ostium, interior of a sinus, etc. and positioned with the deflated balloon 102 situated within an ostium, passageway or adjacent to tissue or matter that is to be dilated, expanded or compressed (e.g., to apply pressure for hemostasis, etc.). Thereafter, the balloon 102 may be inflated to dilate, expand or compress the ostium, passageway, tissue or matter. Thereafter the balloon 102 may be deflated and the device 98 may be removed. This balloon 102 may also be coated, impregnated or otherwise provided with a medicament or substance that will elute from the balloon into the adjacent tissue (e.g., bathing the adjacent tissue with drug or radiating the tissue with thermal or other energy to shrink the tissues in contact with the balloon 102). Alternatively, in some embodiments, the balloon may have a plurality of apertures or openings through which a substance may be delivered, sometimes under pressure, to cause the substance to bathe or diffuse into the tissues adjacent to the balloon. Alternatively, in some embodiments, radioactive seeds, threads, ribbons, gas or liquid, etc. may be advanced into the catheter shaft 100 or balloon 102 or a completely separate catheter body for some period of time to expose the adjacent tissue and to achieve a desired diagnostic or therapeutic effect (e.g. tissue shrinkage, etc.).

Figure 5F:
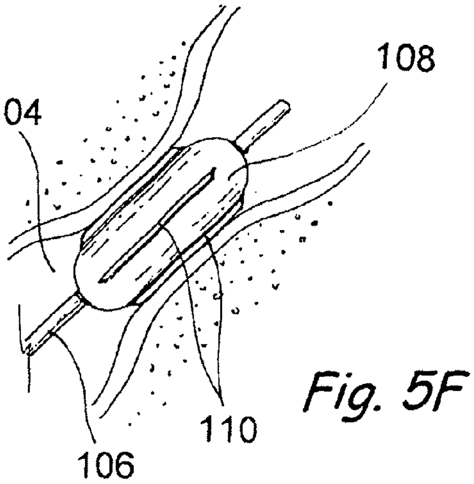
FIG. 5F is a partial perspective view of a balloon catheter having blades or electrodes thereon, being used in accordance with the present invention.

FIG. 5F shows a balloon/cutter catheter device 104 comprising a flexible catheter 106 having a balloon 108 with one or more cutter blades 110 formed thereon. The device 104 is advanced, with balloon 108 deflated, into a passageway such as a nostril, nasal cavity, meatus, ostium, interior of a sinus, etc. and positioned with the deflated balloon 108 situated within an ostium, passageway or adjacent to tissue or matter that is to be dilated, expanded or compressed and in which it is desired to make one or more cuts or scores (e.g. to control the fracturing of tissue during expansion and minimize tissue trauma etc.). Thereafter, the balloon 108 may be inflated balloon to dilate, expand or compress the ostium, passageway, tissue or matter and causing the cutter blade(s) 110 to make cut(s) in the adjacent tissue or matter. Thereafter the balloon 108 may be deflated and the device 104 may be removed. The blade may be energized with mono or bi-polar RF energy or simply be thermally heated to part the tissues in a hemostatic fashion, as well as cause contraction of collagen fibers or other connective tissue proteins, remodeling or softening of cartilage, etc.

Figure 5G:
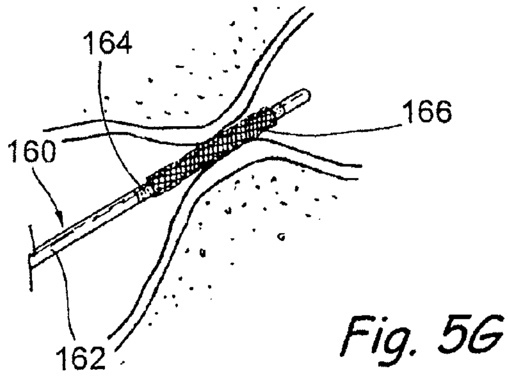
FIG. 5G' is a partial perspective view of a balloon catheter having a stent positioned thereon being inserted into an occluded region within the nose, nasopharynx or paranasal sinus in accordance with the present invention.
Figure 5G:
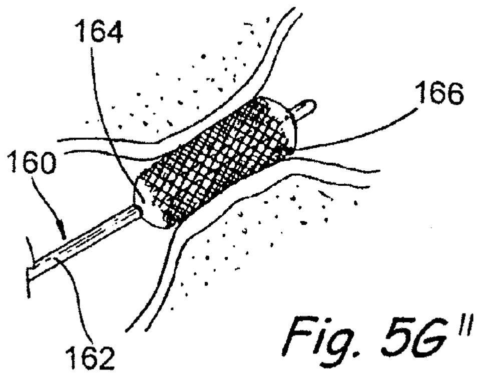
Figure 5G:
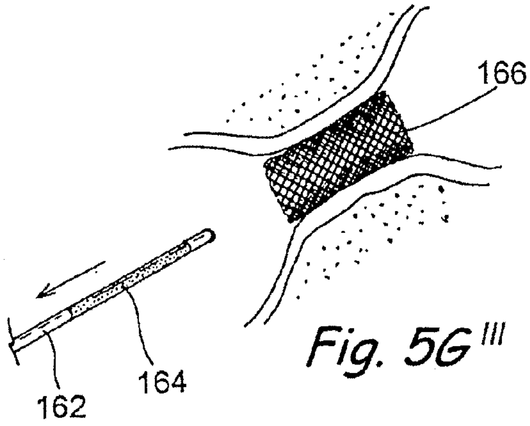

FIGS. 5G'-5G''' show a device 160 and method for delivery of a pressure expandable stent 166. This device 160 comprises a flexible catheter 162 having a balloon 164 thereon. Initially, as shown in FIG. 5G', the balloon 164 is deflated and the stent 166 is radially compressed to a collapsed configuration, around the deflated balloon 164. The catheter 162 with the balloon 164 deflated and the collapsed stent 166 mounted thereon is advanced into a passageway such as a nostril, nasal cavity, meatus, ostium, interior of a sinus, etc. that is to be stented. Thereafter, the balloon 164 is inflated causing the stent 166 to expand to a size that frictionally engages the surrounding tissue so as to hold the stent 166 in place, as shown in FIG. 5G''. In some instances the procedure will be performed for the purpose of enlarging a passageway (e.g., an ostium, meatus, etc.) and the stent 166 will be expanded to a diameter that is sufficiently large to cause the desired enlargement of the passageway and the stent will then perform a scaffolding function, maintaining the passageway in such enlarged condition. After the stent 166 has been fully expanded and implanted, the balloon 164 may be deflated and the catheter 162 removed as shown in FIG. 5G'''. In some applications, the stent may contain a diagnostic or therapeutic substance as defined herein and such substance may elute from the stent 166 into the surrounding tissue to bring about a desired diagnostic or therapeutic effect. In some cases, the stent 166 may be permanently implanted. In other cases the stent 166 may be temporarily implanted. In cases where the stent 166 is temporarily implanted, it may be removed in a second procedure conducted to retrieve the stent 166 or the stent 166 may be made of bioabsorbable or biodegradable material such that it degrades or is absorbed within a desired period of time after implantation. In some cases, such as when the stent is to be placed within the ostium of a paranasal sinus, the stent and/or the balloon may be specifically shaped to facilitate and/or cause the stent 166 to seat in a desired position and to prevent unwanted slippage of the stent 166. For example, the stent 166 and/or balloon 164 may have an annular groove formed about the middle thereof or may be hourglass or venture shaped, to facilitate seating of the stent 166 within an ostium or orifice without longitudinal slippage of the stent 166. In some cases it may be desirable to leave a tether or suture attached to the stent 166 to allow for simple removal of the stent 166 in the physician's office or other suitable location. In some cases the procedure may be intended to actually break bone (e.g., where the stent is intended to dilate or enlarge a sinus ostium). Thus, the balloon 164 may be made of polymeric material including, but not limited to flexible polyvinyl chloride (PVC), polyethylene terephthalate (PET), cross-linked polyethylene, polyester, polyamide, polyolefin, polyurethane and silicone. Various balloon properties (strength, flexibility, thickness, etc.) may be modified by, but not limited to, blending, layering, mixing, co-extruding, irradiating, and other means of engineering balloon material(s). This allows for the use of compliant balloons that can conform to the surrounding structure or non-compliant balloons that can deform or break the surrounding structures (e.g., bone).

Figure 5H:
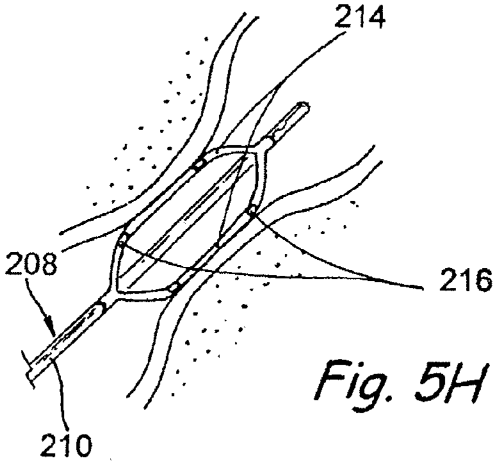
FIG. 5H is a partial perspective view of a tissue shrinking electrode device being used in accordance with the present invention.

FIG. 5H shows an electrosurgical device 208 comprising a flexible shaft 210 (e.g., a catheter or solid shaft) having arched strut members 214 attached thereto. Electrodes 216 are located on the strut members 214. In some cases, the strut members may be of fixed configuration and in other cases the strut members 214 may be collapsible and expandable. In operation, the device 208 is advanced into a passageway such as a nostril, nasal cavity, meatus, ostium, interior of a sinus, etc. Thereafter, current is applied to the electrodes 216 causing tissue adjacent to the struts 214 to be cauterized or heated. The electrodes 216 may be bipolar, monopolar or facilitated by any other suitable form of energy such as a gas or plasma arc. Additionally, sensing elements may also be attached to the catheter and/or strut members to monitor various parameters of the catheter and/or surrounding tissue (e.g., temperature, etc.). In instances where monopolar electrodes are used, a separate antenna electrode (not shown) will be applied to the patient's body in accordance with processes and techniques that are well known in the art.

Figure 5I:
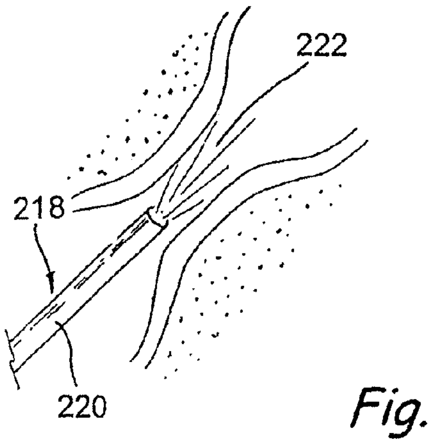
FIG. 5I is a partial perspective view of a cryogenic or plasma state treatment device being used in accordance with the present invention.

FIG. 5I shows a device 218 that delivers a flow 222 of material (e.g., cryogenic material, diagnostic or therapeutic agent, etc.) or energy (laser light, infrared light, etc.) to the tissues adjacent to the passage or body cavity in which the device 218 is positioned. This device comprises a flexible catheter 220 with an outlet aperture or lens at or near its distal end, through which the flow of material or energy is delivered. This device may be used to cryogenically freeze polyps or other tissues or to deliver laser energy to turbinates or other tissues for the purpose of ablating the tissue or to heat the tissue to a temperature that results in shrinking of the tissue.

Figure 5J:
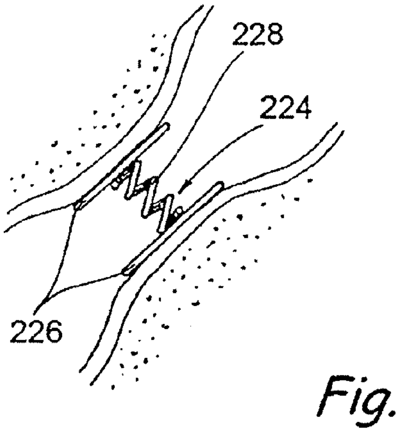
FIG. 5J is a partial perspective view of an expandable tissue expanding device positioned within a passageway in the nose, nasopharynx or paranasal sinus in accordance with the present invention.

FIG. 5J shows an implantable pressure exerting device 224 that is implantable within a passageway such as a nostril, nasal cavity, meatus, ostium, interior of a sinus, etc. to exert pressure on bone, cartilage, soft tissue, etc. Examples of situations where it is desirable to apply such pressure to an anatomical structure include those wherein it is desired to splint or maintain approximation of a broken bone or those wherein it is desired to cause remodeling or gradual repositioning or reshaping of bone, cartilage, soft tissue or other structures. This implantable device 224 comprises a pressure exerting member 228 and two or more plate members 226. The device 224 is initially constrained in a collapsed configuration wherein the pressure exerting member 228 is compressed or collapsed and the device 224 is advanced into a passageway such as a nostril, nasal cavity, meatus, ostium, interior of a sinus, etc. where it is desired to apply pressure to an anatomical structure. When the device 224 is in the desired position, the pressure exerting member 228 is expanded or elongated to exert outward pressure on the plate members 226 and onto the anatomical structures against which the plate members 226 are positioned. In some embodiments, the pressure exerting member may comprise a spring. In other embodiments, the pressure exerting member may comprise a ratchet, hydraulic cylinder or other mechanical apparatus that may be adjusted to create a desired amount of pressure on the plate members 226. In some applications, the pressure exerting member 228 may be adjustable in situ (i.e., with the device implanted in the body) so as to allow the operator to periodically change the amount of pressure being applied to the anatomical structures of interest (e.g., the operator may change to position of a ratchet or add fluid to a hydraulic cylinder) thereby bringing about gradual remodeling or movement of an anatomical structure in a manner similar to that achieved during dental orthodontia. Thus, this pressure exerting device 224 has broad applicability in a variety of procedures including those intended to enlarge a sinus ostium or to straighten an intranasal septum.

Figure 5K:
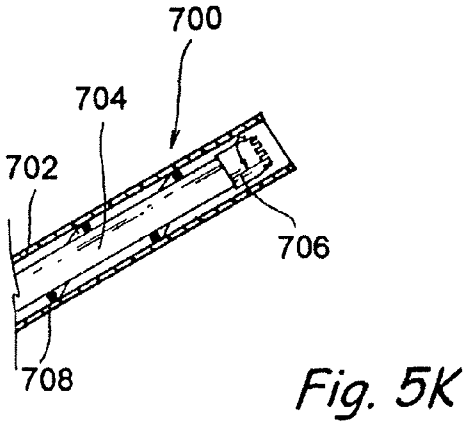
FIG. 5K is a partial sectional view of one embodiment of a forward cutting/suction catheter of the present invention.
Figure 5K:
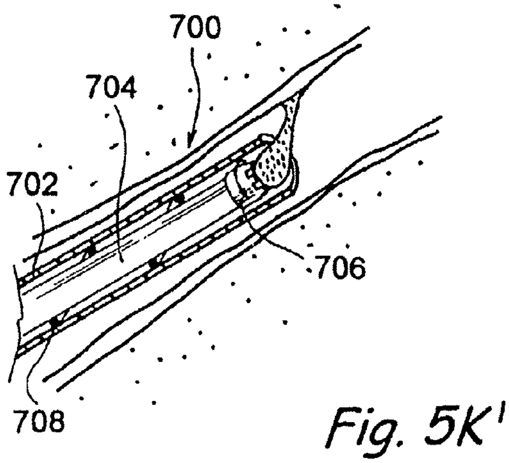
Figure 5L:
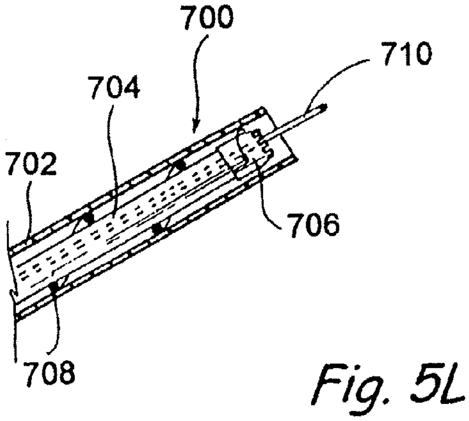
FIG. 5L is a partial sectional view of a forward cutting/suction catheter/endoscope device of the present invention.

FIGS. 5K-5K' and 5L show a forward rotary cutting catheter device 700 that comprises a flexible outer tube 702 and a flexible inner tube 704 disposed coaxially and rotatably mounted within the outer tube 702. One or more bearings 708 (e.g., a helical bearing or a series of individual cylindrical bearings) may be disposed between the outer tube 702 and inner tube 704, as shown. Alternatively, one or both apposing tube surfaces may be made of, lined with, or be coated by etc. a lubricious material such as silicone or PTFE to facilitate movement. A rotating cutter 706 is positioned on the distal end of the inner tube 704. In operation, as shown in FIG. 5K', the device 700 is advanced through a passageway such as a nostril, nasal cavity, meatus, ostium, interior of a sinus, etc. to a position where the distal end of the device 700 is positioned just behind some obstructive matter, such as a polyp P. The inner tube 704 and its cutter 706 are rotated as the device is advanced into the obstructive matter P and/or suction is applied through the lumen of the inner tube 704 and/or through the lumen of the outer tube 702 to draw the obstructive matter P into contact with the rotating cutter 706. It is to be appreciated that, although this embodiment shows a rotating cutter 706, various other types of cutters such as lasers, radiofrequency cutters and other mechanical cutters, etc. may be used instead. As the obstructive matter P is severed by the rotating cutter 706 the obstructive matter P or pieces thereof may be suctioned through the lumen of the inner tube 704 and/or through the lumen of the outer tube 702. In some applications, as shown in FIG. 5L, a scope or guidewire 710 may extend through the lumen of the inner tube to facilitate advancement and positioning of the device 700 prior to the removal of the obstructive matter P.

Figure 5M:
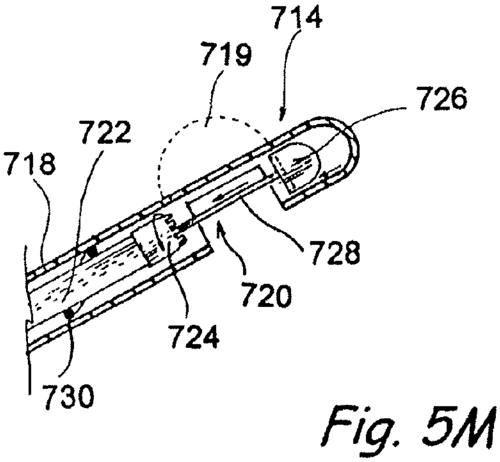
FIG. 5M is a partial sectional view of a side cutting/suction catheter device of the present invention.
Figure 5N:
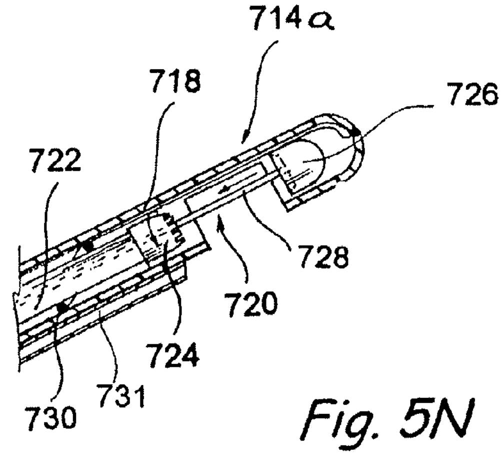
FIG. 5N is a partial sectional view of a side cutting/suction catheter device of the present invention having an optional guidewire lumen and optional endoscopic component(s).

FIGS. 5M and 5N show a side rotary cutting device 714 comprising a flexible outer tube 718 and a flexible inner tube 722 that is disposed coaxially and rotatably mounted within the outer tube 718. One or more bearings 730 (e.g., a helical bearing or a series of individual cylindrical bearings) may be disposed between the outer tube 718 and inner tube 722, as shown. Alternatively, one or both apposing tube surfaces may be made of, lined with, or be coated by etc. a lubricious material such as silicone or PTFE to facilitate movement. A rotating cutter 724 is positioned on the distal end of the inner tube 722. A side opening 720 is formed in the outer tube 718 and the cutter 724 is positioned proximal to the side opening 720. A pull member 728 extends through the inner tube 722 and is attached to a retractor head 726. In operation, the device 714 is advanced and/or torqued to a position where the side opening 720 is near a polyp, tissue or other obstructive matter to be removed. The inner tube 722 and its cutter 724 are rotated. In some applications, suction may be applied through the inner tube 722 and/or through the lumen of the outer tube 718 to draw the obstructive matter into the side opening 720. The pull member 728 is pulled in the proximal direction, causing the retractor head 726 to retract or pull the obstructive matter into contact with the rotating cutter 724. As the obstructive matter is severed by the rotating cutter, the severed obstructive matter or pieces thereof may be suctioned through the lumen of the inner tube 722 and/or through the lumen of the outer tube 718. The pull member 728 may then be advanced in the distal direction to return the retractor head 726 to its original position as shown in FIGS. 5M and 5N. An optional balloon 719 or other laterally extendable member may be located on the side of the catheter 718 opposite the side opening 720 to push the side opening 720 against a lumen wall or into the direction of a polyp or other tissue to be removed. Alternatively, the catheter may incorporate a deflectable tip or a curved distal end that may force the side opening of the catheter against a lumen wall or into the direction of a polyp or other tissue to be removed. With specific reference to FIG. 5N, there is shown a side rotary cutting device 714*a* that includes all of the elements of the device 714 shown in FIG. 5M, but includes a side lumen 731. A scope may be permanently positioned within this side lumen 731 or a scope may be temporarily inserted into (or through) the side lumen 731 to enable the operator to view the area near the side opening 720 and to facilitate the advancement and positioning of the device 714A. Also, the side lumen 731 may function as a guidewire lumen to allow the device 714A to be advanced over a guidewire.

It is to be understood that any of the devices described within this document may be further modified to include any one of the following devices within its structure: electromagnetic positioning sensor/detector (Biosense/JNJ, Surgical Navigation Technologies/Medtronic, Calypso Medical), RF sensor/transmitter, magnetic direction localizer (Stereotaxis, Inc.), thermal sensor, radiopaque composition, radioactive detection emitter/sensor, ultrasonic scanner/transmitter/receiver, Doppler scanner, electrical stimulator, fiber optic, digital optic, local diagnostic chip containing elements responsive to the presence or absence of certain substances and therefore having the ability to diagnose the presence of fungus, microbes, viruses, blood, abnormal mucous content, cancer cells, drugs of abuse, genetic abnormalities, metabolic bi-products, etc.

It is to be further understood that any and all of the devices described in this patent application may incorporate, or may be used in conjunction with, endoscopes. Such endoscopes will typically include light transmitting optical fibers for casting light in the area to be viewed by the scope and image transmitting optical fibers for carrying an image received by the scope to an eyepiece or monitor device located outside the patient's body. In some embodiments a scope, such as a disposable and/or flexible scope, may be affixed to the working device. Examples of such endoscopes that are suitable for incorporation into the working devices of this invention include that described in U.S. Pat. Nos. 4,708,434; 4,919,112; 5,127,393; 5,519,532; 5,171,233, 5,549,542, 6,551,239 and 6,572,538 as well as published United States Patent Application No. 2001/0029317A1, the entireties of which are expressly incorporated herein by reference.

It is to be further understood that any catheters or elongate flexible devices of this invention may include design elements that impact performance features which include, but are not limited to, durability, flexibility, stiffness, length, profile, lubricity, trackability, steerability, torqueability, deflectability, guidance, and radiopacity. Design elements can include, but are not limited to, use of various polymers and metals, use of varying durometer materials to establish a desired flexibility gradient along the device, blending/mixing/layering/co-extruding etc. various materials, using bearings or lubricious coatings or lubricious materials (e.g., silicone, PTFE, parylene, polyethylene, etc.) where two or more surfaces will move relative to each other (e.g., guidewire or instrument lumen, deflecting tendon in lumen, etc.), use of braiding or springs to increase torque control over the device, using materials (e.g. barium, tantalum, etc.) to increase polymer radiopacity, and use of elements to predictably deflect various sections of the catheter (e.g., tension straps or wires, shape memory alloys such as nitinol, etc.).

It is to be further understood that any of the catheters, scopes, elongate working devices or other devices disclosed in this patent application may be rendered steerable or volitionally bendable, unless to do so would make such device inoperative for its intended purpose. Steerable catheters and scopes are well known in the art and may utilize mechanical steering assemblies (e.g., pull wires, hinges, etc.) or shape memory materials (e.g., nickel titanium alloys, shape memory polymers, etc.) to induce the device to undergo the desired bending or curvature after it has been inserted into the body. Examples of apparatus and construction that may be used to render these devices steerable or volitionally bendable include but are not limited to those described in U.S. Pat. No. 5,507,725 (Savage et al.), U.S. Pat. No. 5,656,030 (Hunjan et al.), U.S. Pat. No. 6,183,464 (Webster), U.S. Pat. No. 5,251,092 (Qin et al.), U.S. Pat. No. 6,500,130 (Kinsella et al.), U.S. Pat. No. 6,571,131 (Nguyen), U.S. Pat. No. 5,415,633 (Lazarus et al.), U.S. Pat. No. 4,998,916 (Hammerslag et al.), U.S. Pat. No. 4,898,577 (Badger et al.), U.S. Pat. No. 4,815,478 (Buchbinder et al.) and published United States Patent Applications No. 2003/0181827A1 (Hojeibane et al.) and 2003/0130598A1 (Manning et al.), the entireties of which are expressly incorporated herein by reference.

Figure 5O:
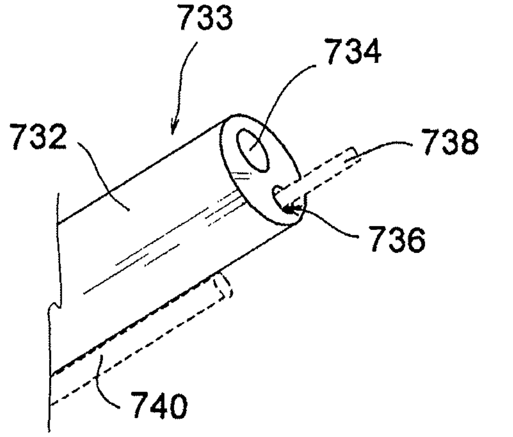
FIG. 5O is a partial perspective view of the distal end of a guide catheter/endoscope of the present invention.

FIG. 5O shows a flexible catheter 733 having a working lumen 734 that extends though the catheter 732 and terminates in a distal end opening. Optionally, a second lumen 736 may also extend though the catheter 732 and terminate in a distal end opening, as shown. An endoscope 738 may be permanently positioned within this lumen 736 or such endoscope 738 may be temporarily inserted into (or through) the lumen 736 to enable the operator to view the area distal to the catheter 732. Additionally or alternatively, a side scope or lumen 740 may be located on the catheter 732 and an endoscope may be permanently embodied by or positioned in or temporarily inserted into (or through) such side scope or lumen 740 to enable the operator to view the area distal to the catheter 732 and, in at least some cases, the distal end of the catheter 732 itself. In any devices which incorporate such optional side scope or lumen 740, the side scope or lumen 740 may be of any suitable length and may terminate distally at any suitable location and such side scope or lumen 740 is not limited to the specific positioning and the specific distal end location shown in the drawings. Also, in embodiments that incorporate a side scope or lumen 740 such side lumen may be employed as a guidewire or working lumen to permit the catheter to be advanced over a guidewire or for other working devices to be inserted therethrough.

Figure 5P:
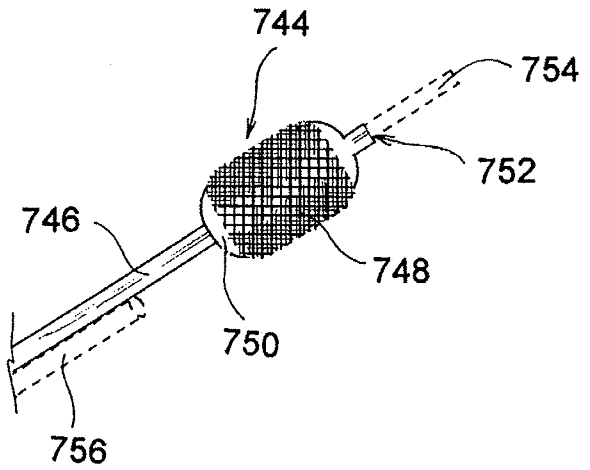
FIG. 5P is a partial perspective view of a balloon catheter/pressure-expandable intranasal stent/endoscope device of the present invention.

FIG. 5P shows a balloon catheter and pressure expandable stent system 744 which includes all of the elements of the balloon expandable stent system shown in FIGS. 5G'-5G''' and, in addition, may incorporate an endoscope or side lumen. Specifically, referring to FIG. 5P, there is shown a balloon catheter and pressure expandable stent system 744 that comprises a flexible catheter 746 having a balloon 750 and pressure expandable stent 748 thereon. A side lumen 756 may be located on the catheter 746 and an endoscope may be permanently positioned in or temporarily inserted into (or through) such side lumen 756 to enable the operator to view the balloon 750 and stent 748 and to advance the catheter 749 to its desired position. Also, in embodiments that incorporate a side lumen 756 such side lumen may be employed as a guidewire lumen to permit the catheter 746 to be advanced over a guidewire. Optionally, a lumen may extend through the catheter 746 and through an opening 752 in the distal end of the catheter 749 and a straight, curved, bendable, deflectable or steerable scope and/or stent 754 may be passed through or received in that lumen to facilitate over the wire and/or scope assisted and/or guided and/or manipulated advancement of the catheter 749 to an intended location. In routine use, the balloon 750 is initially deflated and the stent 748 is radially compressed to a collapsed configuration, around the deflated balloon 750. The catheter 746 with the balloon 750 deflated and the collapsed stent 748 mounted thereon is advanced, under endoscopic guidance or over a guidewire, to a position within a passageway such as a nostril, nasal cavity, meatus, ostium, interior of a sinus, etc. that is to be stented. Thereafter, the balloon 750 is inflated causing the stent 748 to expand to a size that frictionally engages the surrounding tissue so as to hold the stent 748 in place. In some instances the procedure will be performed for the purpose of enlarging a passageway (e.g., an ostium, meatus, etc.) and the stent 748 will be expanded to a diameter that is sufficiently large to cause the desired enlargement of the passageway and the stent 748 will then perform a scaffolding function, maintaining the passageway in such enlarged condition. After the stent 748 has been fully expanded and implanted, the balloon 750 may be deflated and the catheter 748 removed. In some applications, the stent 748 may contain a diagnostic or therapeutic substance as defined herein and such substance may elute from the stent 748 into the surrounding tissue to bring about a desired diagnostic or therapeutic effect. In some cases, the stent 748 may be permanently implanted. In other cases the stent 748 may be temporarily implanted. In cases where the stent 748 is temporarily implanted, it may be removed in a second procedure conducted to retrieve the stent 748 or the stent 748 may be made of bioabsorbable or biodegradable material such that it degrades or is absorbed within a desired period of time after implantation. As shown in the examples of FIGS. 5R' and 5R'', in some cases, such as when a stent is to be placed within the ostium of a paranasal sinus, the stent and/or the balloon may be specifically shaped to facilitate and/or cause the stent to seat in a desired position and to prevent unwanted slippage of the stent. For example, FIG. 5R' shows a device 1040 comprising a catheter 1042 having a balloon 1044 and stent 1046 mounted thereon as described above. However, in this embodiment, the balloon 1044 and stent 1046 are of a configuration where one end of the balloon 1044 and stent 1046 is larger in diameter than the other end. As described above in connection with other embodiments such as those shown in FIGS. 5P and 5Q, a side scope or side lumen 1048 may optionally be formed on the catheter 1042 and/or a scope or guidewire 1050 may optionally be passed through a lumen of the catheter 1042 and out of its distal end. FIG. 5R'' shows another device 1052 comprising a catheter 1054 having a balloon 1056 and stent 1058 mounted thereon as described above. However, in this embodiment, the balloon 1056 and stent 1058 are of a configuration where both ends of the balloon 1056 and stent 1058 are larger in diameter than the middle of the balloon 1056 and stent 1058. As a result, the stent 1058 has an annular groove or indentation formed circumferentially or about the mid-portion thereof or may be hourglass or venture shaped, to facilitate seating of the stent 1058 within an ostium or orifice without longitudinal slippage of the stent 1058. Again, as described above in connection with other embodiments such as those shown in FIGS. 5P and 5Q, a side scope or side lumen 1060 may optionally be formed on the catheter 1052 and/or a scope or guidewire 1062 may optionally be passed through a lumen of the catheter 1054 and out of its distal end. In cases where the procedure is intended to actually break bone (e.g., where the stent 1046, 1058 is intended to dilate or enlarge a sinus ostium) the specially shaped balloon 1044, 1056 may be made of strong polymeric material as described hereabove to enable it to exert bone-breaking pressure on the adjacent or surrounding bone as it is inflated.

Figure 5Q:
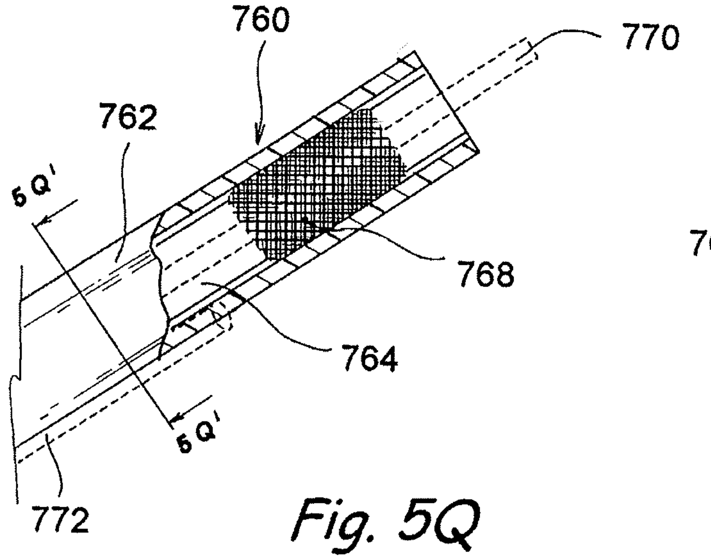
FIG. 5Q is a partial perspective view of a delivery catheter/self expanding intranasal stent/endoscope device of the present invention.
Figure 5Q:
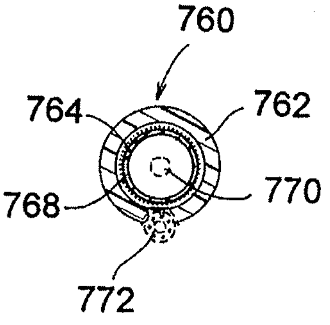
Figure 5R:
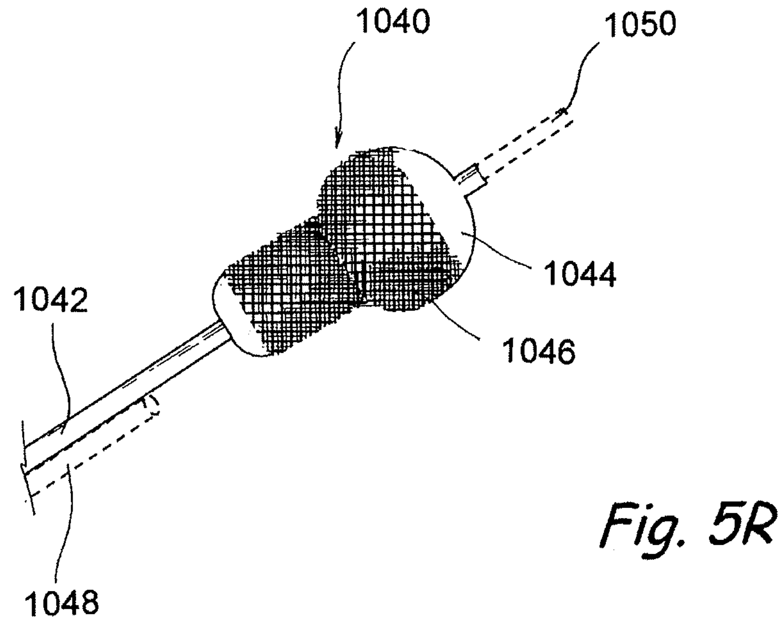
FIG. 5R' shows an example of an optional modified shape of the balloon and stent of FIG. 5P.
Figure 5R:
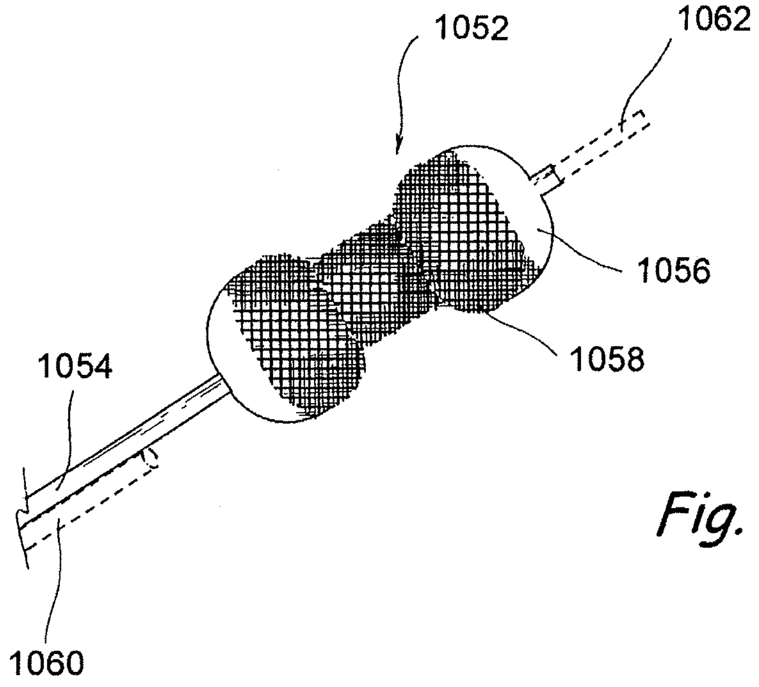

FIGS. 5Q and 5Q' show a self expanding stent and delivery system 760 comprising a flexible outer sheath 762, a flexible inner tube 764 and a stent 768. This stent differs from the stent 748 of FIG. 5P only in that it is resilient and self-expanding rather than pressure expandable. The stent 768 is biased to an expanded configuration. Initially, it is compressed to a radially collapsed configuration on the outer surface of the inner tube 764 and the outer sheath 762 is advanced over the stent 768 to constrain the stent 768 in its collapsed configuration, as can be seen in the cross-sectional showing of FIG. 5Q'. A scope and/or guidewire 770 may be inserted through the lumen of the inner tube 764. Additionally or alternatively, a side lumen 772 may be located on the outer sheath 762 and an endoscope may be permanently positioned in or temporarily inserted into (or through) such side lumen 772 to enable the operator to view the distal portion of the system 760 and the area ahead of the distal end of the sheath 762 as the system is advanced. Also, in embodiments that incorporate a side lumen 772 such side lumen 772 may be employed as a guidewire lumen to permit the system 760 to be advanced over a guidewire. In routine operation the system 760, with its sheath 762 in a distally advanced position such that it surrounds and constrains the collapsed stent 768, is advanced, under endoscopic guidance and/or over a guidewire, to a position within a passageway such as a nostril, nasal cavity, meatus, ostium, interior of a sinus, etc. that is to be stented. Thereafter, when the stent 768 is positioned at the location to be stented, the sheath 762 is withdrawn, allowing the self-expanding stent 768 to spring or self expand to a radially expanded configuration in which it frictionally engages the surrounding anatomical structure. Thereafter, the remainder of the system 760 is removed, leaving the stent 768 implanted in the body. The stent 768 may perform dilation and scaffolding and/or substance delivery function(s) as described hereabove with respect to the pressure expandable stent 748 of FIG. 5P.

Figure 5S:
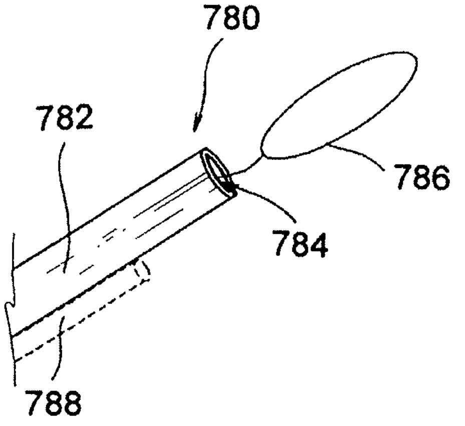
FIG. 5S is a partial perspective view of a snare catheter of the present invention with optional endoscopic component(s).
Figure 5T:
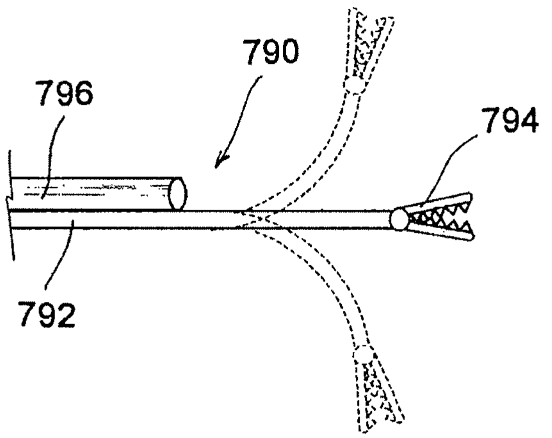
FIG. 5T is a partial perspective view of a forceps device of the present invention having optional endoscopic component(s).

FIG. 5S shows a snare apparatus 780 comprising a flexible catheter 782 having a lumen 784 extending therethrough. A snare 786 having a general loop shape is advanceable out of the lumen 784 of the device 780. In some embodiments, the snare 786 may optionally be charged with electrical current or otherwise heated so that it performs a cauterization function as it cuts through tissue. Additionally or alternatively, in some embodiments, the snare 786 may be of variable diameter (e.g., a noose that may be tightened or loosened by the operator). Also, optionally, a scope or side lumen 788 may be located on the catheter 782 and a stationary or moveable endoscope may be permanently embodied in or temporarily inserted into (or through) such side lumen 788 to enable the operator to view the distal portion of the device 780 and the area of the snare 786. Also, in embodiments where the scope or side lumen 780 comprises a side lumen, such side lumen 788 may be employed as a guidewire lumen to permit the device 780 to be advanced over a guidewire. Alternatively, multiple lumens may run through catheter 782 such that they can accommodate a snare, a guidewire and/or an endoscope. In routine operation, the snare 786 is initially retracted within lumen 784 and the device 780 is advanced under endoscopic guidance and/or over a guidewire, to a position within a passageway such as a nostril, nasal cavity, meatus, ostium, interior of a sinus, etc. where a polyp or other matter to be snared or cut away is located. The snare 786 is advanced out of lumen 784 and positioned around the polyp or other matter and, thereafter, the snare may be pulled or moved, heated (if equipped for heating) and/or tightened (if equipped for tightening) so as to sever or cut the polyp or other matter. In some cases, the severed polyp or other matter bay be suctioned through the lumen 784. In other cases, a separate catheter or device may be introduced to retrieve the severed polyp or other matter. After completion of the procedure, the snare 786 may be retracted into lumen 784 and the device 780 may be removed. Also, in some embodiments, the snare 786 may be replaced by a basket, bag or other retrieval receptacle that is useable to capture and retrieve tissue or other matter and to withdraw it into the lumen of the catheter 782.

FIG. 5T shows a forceps device 790 which comprises a flexible shaft 792 having jaws or forceps 794 thereon. The jaws or forceps 794 may be volitionally opened and closed by the operator. A scope or side lumen 796 may be located on the flexible shaft 792, as shown. In embodiments where the scope or side lumen 792 comprises a scope, such scope may be fixed or moveable and may be used to observe or view the advancement of the device 790 and/or the use of the forceps 794. In embodiments where the scope or side lumen 796 comprises a side lumen, a stationary or moveable endoscope may be permanently embodied in or temporarily inserted into (or through) such side lumen 796 to enable the operator to view the distal portion of the device 790 and the area of the forceps 794. Also, in embodiments where the scope or side lumen 796 comprises a side lumen, such side lumen 796 may be employed as a guidewire lumen to permit the device 790 to be advanced over a guidewire. In routine operation, the device 790 is advanced, either alone or through the lumen of a catheter, and possibly under endoscopic guidance and/or over a guidewire, to a position within a passageway such as a nostril, nasal cavity, meatus, ostium, interior of a sinus, etc. where matter is to be grasped by the forceps. Thereafter, under optional endoscopic guidance and observation, the forceps 794 are used to grasp the intended matter. In some embodiments, a distal portion of the flexible shaft 792 may be bendable or steerable as indicated by doted lines on the example of FIG. 5T. In some embodiments, the jaws of the forceps 794 may be designed to sever and retain a specimen of tissue for biopsy or other tissue sampling applications or the forceps 794 may comprise scissors for cutting tissue, cartilage, bone, etc. Alternatively, a lumen may pass through flexible shaft 792 and exit through or next to the forceps 794 and allow the passage of a guidewire or endoscope through such lumen.

Figure 5U:
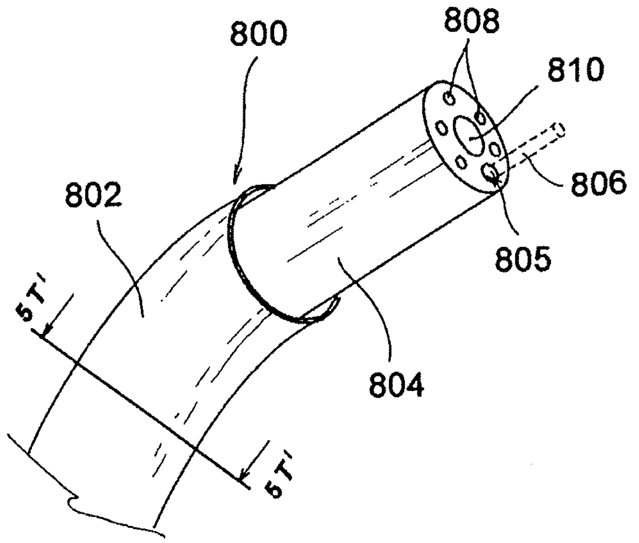
FIG. 5U is a partial perspective view of a system of the present invention comprising a guide catheter, endoscope and guidewire.
Figure 5U:
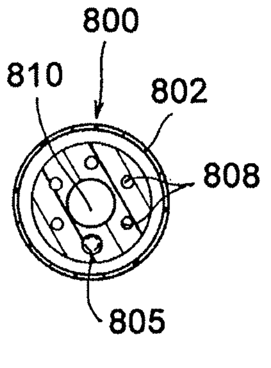

FIGS. 5U and 5U' show a telescoping system 800 comprising a flexible catheter 802, a flexible scope 804 and a guidewire 806. The flexible scope 804 comprises a plurality of light transmitting pathways 808 (e.g., optical fibers) that transmit light in the distal direction from a light source (not shown) and out of the distal end of the scope 804 such that the light is cast onto the object or anatomical structure to be viewed. Also, the scope comprises an image transmitting pathway 810 (e.g., optical fiber and lens) that carries reflected light from distal end of the scope to an eyepiece or monitor on which the image may be viewed. The scope also has a guidewire lumen 805 extending therethrough and opening through its distal end. The scope 804 is advanceable through the flexible catheter 802 and a guidewire 806 that is advanceable through a guidewire lumen 805 of the scope, as shown. In routine operation, the telescoping system 800 may be inserted into the nose and the scope 804 may be utilized to view an anatomical structure, such as the ostium of a paranasal sinus, and facilitate advancement of the guidewire into that anatomical structure. Thereafter, the scope may be advanced over the guidewire and into the anatomical structure (e.g., though the ostium and into the interior of the paranasal sinus). The scope may then be used to examine the anatomical structure (e.g., to view the condition of the mucosa lining the paranasal sinus and to look for signs of infection, tumors, etc.) The catheter 802 may then be advanced over the scope 804 and into the anatomical structure (e.g., the catheter tip may be advanced through the ostium and into the paranasal sinus). Thereafter, the scope 804 may be removed and a diagnostic or therapeutic substance as defined hereabove may be infused through the catheter 802 and/or another working device, including but not limited to the working devices shown in FIGS. 5A-5T and 5V-5Y'''''', may be advanced through the catheter 802 and into the anatomical structure where it is used to perform a diagnostic or therapeutic function.

Figure 5V:
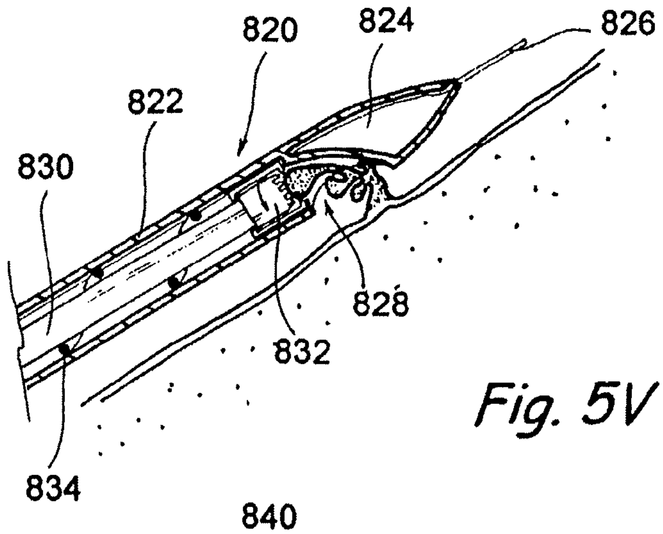
FIG. 5V is a partial perspective view of a microdebrider catheter of the present invention.

FIG. 5V shows a side port suction/cutting device 820 which comprises a flexible outer tube 822, a flexible inner tube 830 is disposed coaxially and rotatably mounted within the outer tube 822. One or more bearings 834 (e.g., a helical bearing or a series of individual cylindrical bearings) may be disposed between the outer tube 822 and inner tube 830, as shown. Alternatively, one or both apposing tube surfaces may be made of, lined with, or be coated by etc. a lubricious material such as silicone or PTFE to facilitate movement. A rotating cutter 832 is positioned on the distal end of the inner tube 830. A side opening 828 is formed in the outer tube 822 and the cutter 832 is positioned proximal to the side opening 828. Optionally, a tapered atraumatic distal tip 824 may be formed on the distal end of the outer tube 822 and the side opening 828 may be configured to form a ramp or chute through which matter may pass into the area immediately distal to the cutter 832. Also optionally, an opening may be formed in the distal end of the distal tip such that a guidewire or scope 826 may pass through the lumen of the inner tube 830 and out of the opening in the distal tip, as shown. In operation, the device 820 is advanced to a position where the side opening 828 is near a polyp, tissue or other obstructive matter to be removed. The inner tube 830 and cutter 832 are rotated. Suction may be applied through the lumen of the inner tube 830 and/or through the lumen of the outer tube 822 to draw the obstructive matter into the side opening 828 and into contact with the rotating cutter 832. As the obstructive matter is severed by the rotating cutter 832, the severed obstructive matter or pieces thereof may be suctioned through the lumen of the inner tube 830 and/or through the lumen of the outer tube 822. Of course, as in any of the working devices described in this patent application, a scope or side lumen of any size or length, into which a scope may be inserted (not shown in FIG. 5U but shown in various other figures such as FIGS. 5O, 5P, 5Q, 5R, 5S and 5T) may be attached to the outer tube 822 at a position which allows a scope to be used to view the side opening 828 and matter entering the side opening 828. Alternatively, the catheter may incorporate a deflectable tip or a curved distal end which may force the side opening of the catheter against a lumen wall or into the direction of a polyp or other tissue to be removed.

Figure 5W:
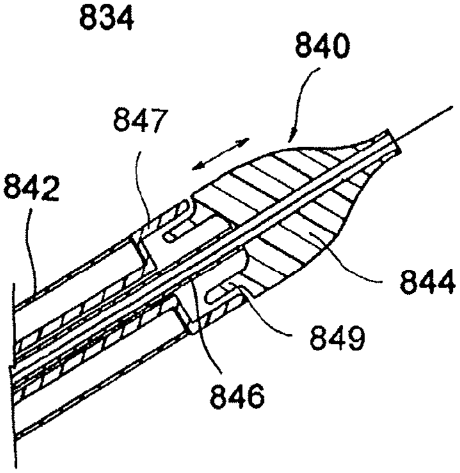
FIG. 5W is a partial perspective view of a bone remodeling device of the present invention.
Figure 5W:
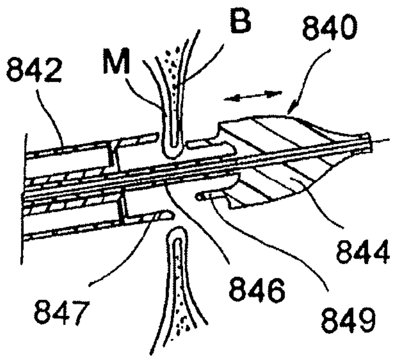
Figure 5W:
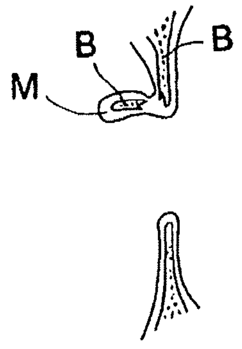

In some applications of the invention, it may be desirable to break bone, such as the thin bone that forms the periphery of a sinus ostium. FIGS. 5W-5X'''' show devices that may be used to break bones at specific locations. For example, FIGS. 5W-5W'' show a device 840 that comprises a flexible catheter 842 having a rigid cylindrical member 847 located on the distal end thereof. An advanceable and retractable member 846 extends through the catheter 842 and is connected to a distal tip member 844. The distal tip member 844 has a cylindrical proximal end 849 that is sized to be received within the cylindrical member 847. As shown in FIGS. 5W' and 5W'', in routine operation, the advanceable and retractable member 846 is advanced to separate the distal tip member 844 from the rigid cylindrical member 847. The device 840 is advanced to a position adjacent to a bony structure, such as a structure formed by bone B covered with mucosal tissue M. The device is positioned such that the bony structure is between the cylindrical proximal end 849 of the distal tip member 844 and the cylindrical member 847. The advanceable and retractable member 846 is then retracted, pulling the distal tip member 844 in the proximal direction and capturing the bony structure between the cylindrical proximal end 849 of the distal tip member 844 and the cylindrical member 847, thereby breaking the bone B. The shape or configuration of the distal tip member 844 and/or cylindrical member 847 may be varied depending on the shape and pattern of break desired to be made in the bone B, In this regard, FIGS. 5X-5X'''' show alternative constructions or configurations that may be used to produce different shapes and patterns of bone breaks. FIG. 5X' shows an assembly 850 comprising a distal tip member 852 that has three (3) projections on its proximal side and a proximal member 854 that has three (3) notches in its distal surface, such notches being configured to receive the three projections of the distal tip member 852 when the distal tip member 852 is retracted. FIG. 5W'' shows an assembly 860 comprising a distal tip member that forms a pincher for breaking bone. FIG. 5X''' shows an assembly 870 comprising a collapsible distal tip member 872 and a cylindrical proximal member 874. The distal tip member 872 may be initially deployed in a collapsed configuration that allows it to be advanced through an opening such as the ostium of a sinus. Then, it may be expanded to a size that is too large in diameter to pass through that opening, thereby causing it to strike the periphery of the opening as it is retracted in the proximal direction. In this manner, the assembly 5X''' may be used to break bone B all the way around an ostium or aperture. FIG. 5X'''' shows another assembly 880 comprising a distal tip 882 that has two projections on its proximal side and a proximal member 884 that has one projection on its distal side. The projection on the distal side of the proximal member 884 is received between the projections formed on the proximal side of the distal member 882 when the distal member 882 is retracted in the proximal direction.

FIGS. 5Y'-5Y''''' show various substance delivery implants that may be implanted into the nasal cavities, paranasal sinuses, middle or inner ear, nasopharynx, etc. to deliver a diagnostic or therapeutic substance as defined herein. These devices may be formed of permanent or bio-absorbable material. In many instances, these devices will be formed of a polymer (e.g., Hydron, hydrogel, collagen, etc.) within which the diagnostic or therapeutic substance is contained or a polymer or metal that is coated with or otherwise contains the substance. FIG. 5Y' shows an implant 1070 that comprises a bead or pellet. FIG. 5Y'' shows an implant 1072 that comprises a wafer. FIG. 5Y''' shows an implant 1074 that comprises a brad or staple. FIG. 5Y'''' shows an implant 1076 that comprises a screw or helical coil. FIG. 5Y''''' shows an implant 1078 that comprises a strand or coil, another example of which is shown in FIG. 7E and described herebelow.

D. Pre-Shaped Guide Catheters

FIGS. 6A-6E show various guide catheters that may be used in the methods of the present invention.

Figure 6A:
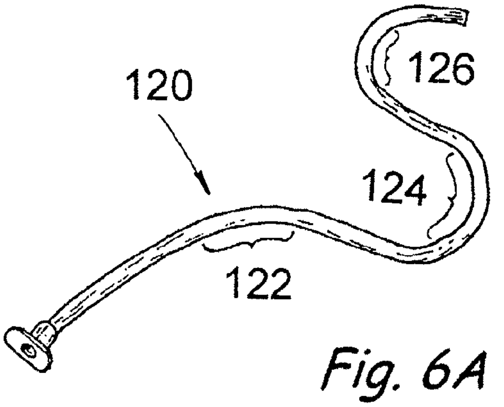
FIG. 6A is a perspective view of one embodiment of a sphenoid sinus guide catheter of the present invention.

FIG. 6A shows a sphenoid sinus guide catheter 120 that incorporates three preformed curves 122, 124, 126. The three dimensional shape of the catheter 120 is such that, when advanced through a nasal cavity, the distal end of the catheter 120 will tend to enter the ostium of the sphenoid sinus.

Figure 6B:
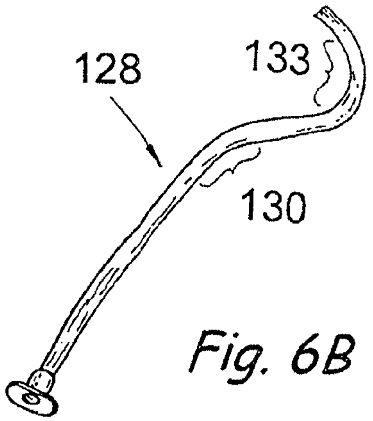
FIG. 6B is a perspective view of a frontal sinus guide catheter of the present invention.

FIG. 6B shows a frontal sinus guide catheter 128 that incorporates two preformed curves 130, 133. The shape of the catheter 128 is such that, when advanced through a nasal cavity, the distal end of the catheter 128 will tend to enter the ostium of the frontal sinus.

Figure 6C:
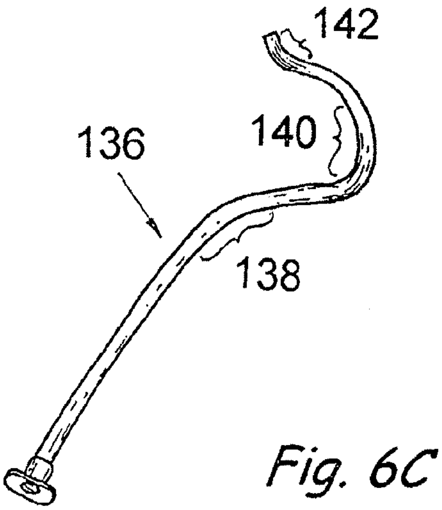
FIG. 6C is a perspective view of one embodiment of a maxillary sinus guide catheter of the present invention.

FIG. 6C shows a maxillary sinus guide catheter 136 that incorporates three preformed curves 138, 140, 142. The three dimensional shape of the catheter 136 is such that, when advanced through a nasal cavity, the distal end of the catheter 136 will tend to enter the ostium of the maxillary sinus.

Figure 6D:
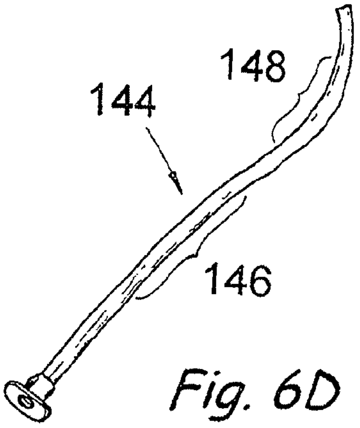
FIG. 6D is a perspective view of one embodiment of an ethmoid sinus guide catheter of the present invention.

FIG. 6D shows an ethmoid sinus guide catheter 144 that incorporates two preformed curves 146,148. The three dimensional shape of the catheter 144 is such that, when advanced through a nasal cavity, the distal end of the catheter 144 will tend to enter the ostium of the ethmoid sinus.

In some of the methods of the invention, it will be desirable to plug the ostium of a sinus or another opening such as the nasolacrimal duct or the nasopharyngeal opening into the Eustachian tube. Thus, any of the above-described guide catheters 120, 128, 136, 144 may be equipped with a plug on its distal tip such that when its distal end enters the sinus ostium it will plug the sinus thereby preventing fluid from exiting the sinus through the ostium. An example of one such procedure is shown in FIG. 7B and described herebelow.

Figure 6E:
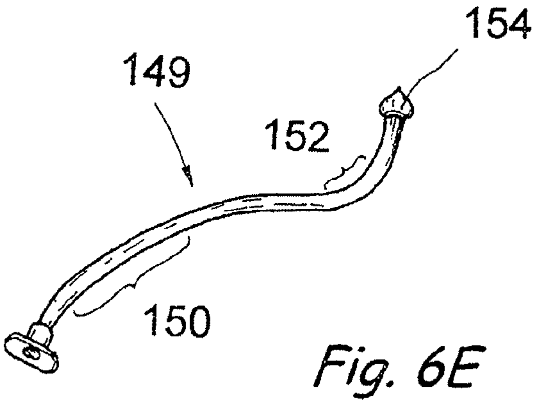
FIG. 6E is a perspective view of one embodiment of a plugging guide catheter of the present invention useable for temporarily plugging the opening into a nasolacrimal duct or Eustachian tube.

FIG. 6E shows a plug guide catheter 149 that is useable for temporarily plugging the opening into a nasolacrimal duct. This plug guide catheter 149 has two preformed curves 150, 152 and a plug 154 at its distal tip. The three dimensional configuration of this catheter 149 is such that, when advanced through a nasal cavity the distal tip plug 154 will tend to enter the opening into the nasolacrimal duct. The plug may consist of, but is not limited to, a semi-rigid plug or a balloon on the end of the catheter. It will be appreciated that a different shaped plug guide catheter (not shown) may be used to plug the Eustachian tube.

E. Devices and Methods for Treatment Within Paranasal Sinuses:

FIGS. 7A-7G provide examples of devices and methods for performing diagnostic or therapeutic procedures within the paranasal sinuses. In the methods of the prior art, rigid or flexible scopes are sometimes used to visualize the ostia of sinuses but, typically, such scopes have not actually been advanced into the interior of the sinuses. As described hereabove, the present invention does provide devices and methods for placing endoscopes inside the paranasal sinuses and such methods may or may not be used in conjunction with any of the diagnostic or therapeutic devices and methods shown in FIGS. 7A-7G.

Figure 7A:
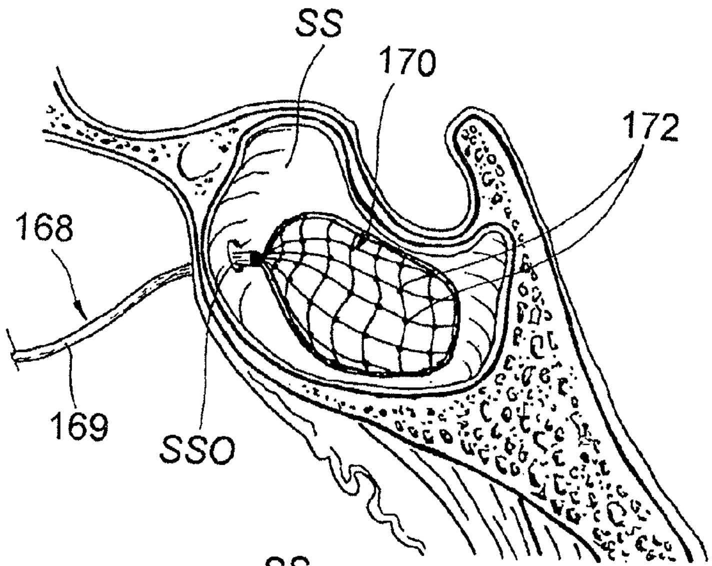
FIG. 7A is a sectional view of a paranasal sinus with a catheter introducing an expandable electrode cage into the sinus in accordance with the present invention.
Figure 7B:
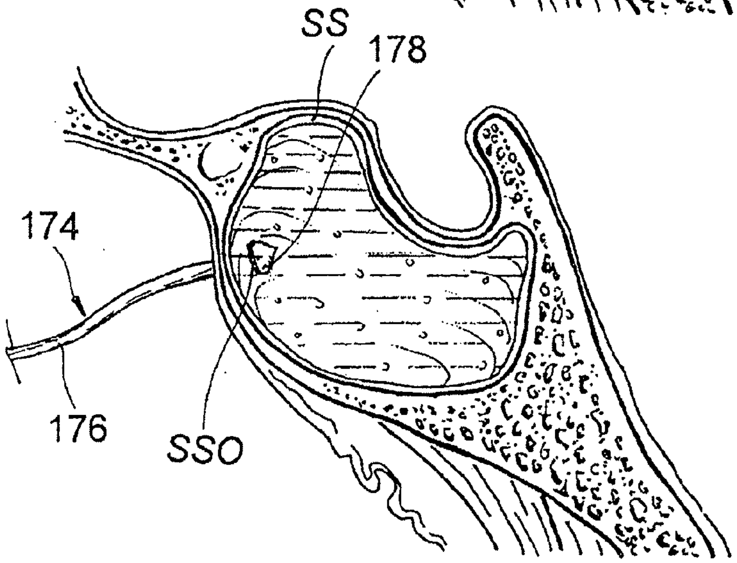
FIG. 7B is a sectional view of a paranasal sinus that is filled with a diagnostic or therapeutic substance and wherein a plug tipped catheter is being used to plug the ostium of the sinus to retain the substance within the sinus, in accordance with the present invention.

FIG. 7A shows an electrode network delivery device 168 being used to deliver radiofrequency or electrical current to the lining of the sphenoid sinus SS. This device 168 comprises a flexible catheter 168 that has been inserted through the sphenoidal sinus ostium SSO. An expandable electrode network such as a cage 170 is advanced out of the distal end of the catheter 169. Electrodes 172 are positioned at spaced apart locations on the cage. As the cage 170 expands, it places the electrodes in contact with the lining of the sinus SS. Current is delivered to the electrodes 172 to ablate all mucous producing tissue within the sinus in preparation for the sinus to be functionally isolated or embolized, or to ablate tumors or polyps located within the sinus.

FIG. 7B shows a procedure where a flowable substance, such as a diagnostic or therapeutic substance as defined above, is introduced into the sphenoid sinus SS and the ostium SSO has been plugged by a sphenoid sinus plug guide catheter device 174. This device 174 comprises a flexible catheter 176 having the shape shown in FIG. 6A and described above and a plug member 178 at its distal tip. The fluid is maintained in the sphenoid sinus SS until the plug catheter device 174 is removed, allowing the fluid to then drain through the sphenoid sinus ostium SSO. This procedure may be particularly useful when it is desired to fill a sinus with radiographic contrast agent to visualize the entire sinus or to apply a therapeutic agent to the entire lining of the sinus by entirely filling the sinus with the agent and maintaining such fully filled state for a desired period of time to allow the agent to act on the entire lining of the sinus. Imaging materials may be mixed with viscous agents so that they simulate mucous or if simple structural imaging is desired it may be preferable to have substances of lower viscosity. It may be also desirable to use imaging agents which bind with the surface of the mucosa to minimize the amount of injected contrast.

Figure 7C:
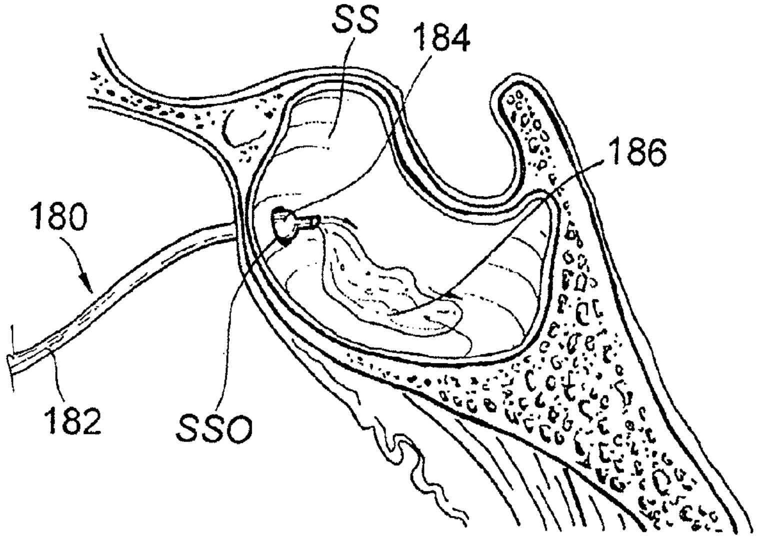
FIG. 7C is a sectional view of a paranasal sinus with a catheter introducing a diagnostic or therapeutic substance into contact with the tissue lining the sinus, in accordance with the present invention.

FIG. 7C shows a balloon catheter device 180 which comprises a flexible catheter 182 having a balloon 184 that is positioned in the sphenoid sinus ostium SSO and inflated to hold the catheter 182 in position while a quantity of a diagnostic or therapeutic substance 186 (as defined above) is introduced into the interior of the sinus SS. This therapeutic substance may be one or more of any of the drug delivery materials and drugs selected from the previous list, or may additionally include a sclerotic agent such as alcohol to uniformly kill all the tissues within the cavity. Other materials such as capasian or other neuro-toxic substances may be considered to eliminate the pain and other sensation within the cavity.

Figure 7D:
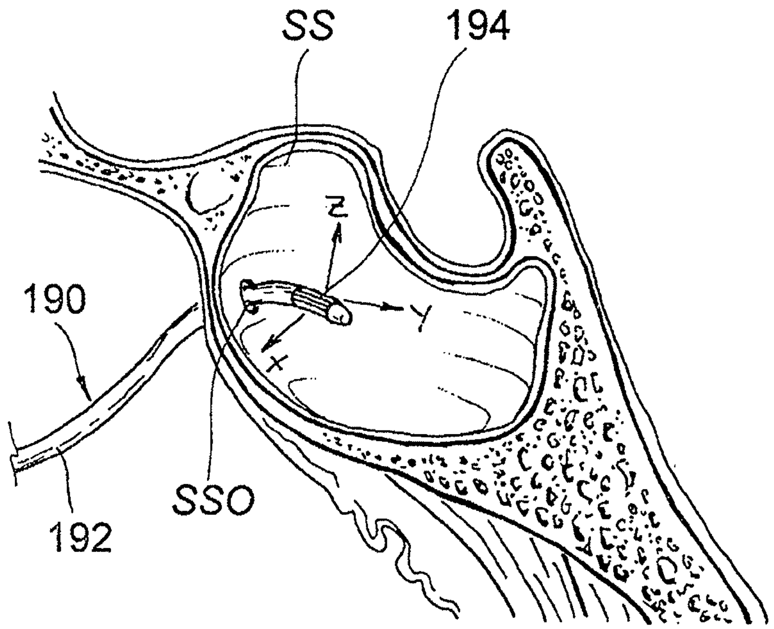
FIG. 7D is a sectional view of a paranasal sinus with a catheter having emitters and/or sensors for 3 dimensional mapping or navigation, in accordance with the present invention.
Figure 7E:
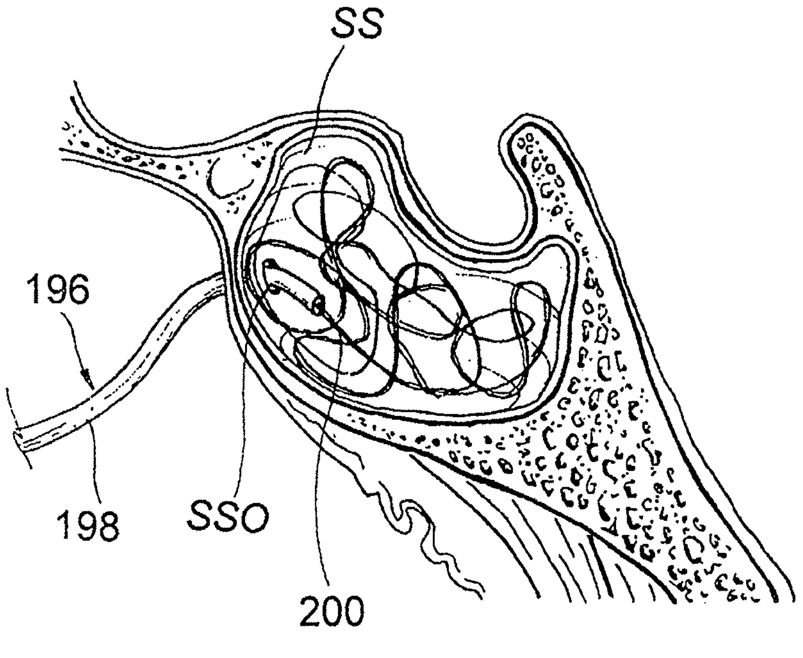
FIG. 7E is a sectional view of a paranasal sinus with a catheter delivering a coil apparatus into the sinus to embolize the sinus and/or to deliver a diagnostic or therapeutic substance into the sinus in accordance with the present invention.

FIG. 7D shows a sensor equipped catheter device 190 that comprises a flexible catheter 192 having a sensor 194 thereon for 3 dimensional mapping or navigation. This procedure may be used to map the precise configuration of the interior of the sphenoid sinus SS. Examples of the construction and use of such sensor 194 and associated systems/computers are found in U.S. Pat. Nos. 5,647,361; 5,820,568; 5,730,128; 5,722,401; 5,578,007; 5,558,073; 5,465,717; 5,568,809; 5,694,945; 5,713,946; 5,729,129; 5,752,513; 5,833,608; 5,935,061; 5,931,818; 6,171,303; 5,931,818; 5,343,865; 5,425,370; 5,669,388; 6,015,414; 6,148,823 and 6,176,829, the entireties of which are expressly incorporated herein by reference.

FIG. 7E shows an implant delivery device 196 which comprises a flexible catheter 198 that is inserted through the sphenoid sinus ostium SSO and into the sphenoid sinus SS and is being used to implant a coil 200 within the sphenoid sinus. Such coil 200 may comprise an elongate fiber or other elongate member that may contain a diagnostic or therapeutic substance as defined herein. This coil 200 may be constructed to embolize the sinus for the purpose of to permanently close off the sinus and to prevent any further mucous production, trapping of secretions or infection and/or to deliver a diagnostic or therapeutic substance to the tissues lining the sinus. For example, a coil for sustained delivery of an antimicrobial agent may be implanted in a sinus to treat an acute or chronic infection of that sinus. In some cases, the coil may be bioabsorbable.

Figure 7F:
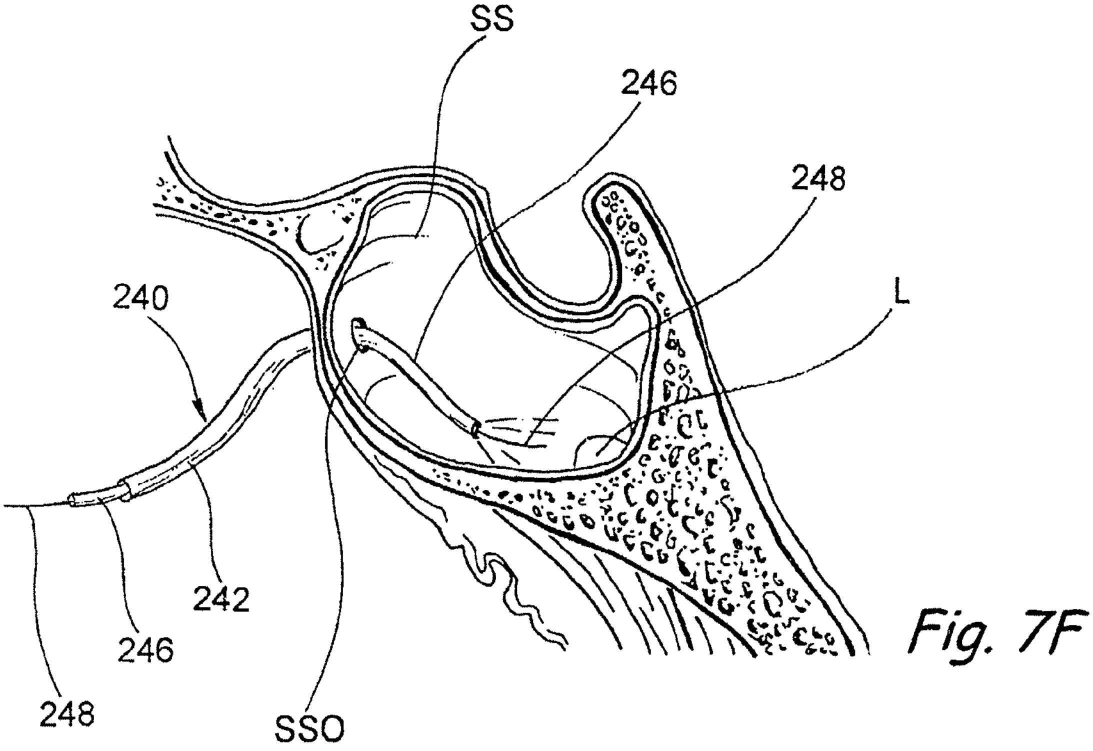
FIG. 7F is a sectional view of a paranasal sinus with a guide catheter, guide wire and over-the-wire flexible endoscope inserted into the sinus, in accordance with the present invention.

FIG. 7F shows an over-the-wire endoscopic system 240 being used to view the interior of the sphenoid sinus SS. A flexible catheter 242 is positioned in or near the sphenoid sinus ostium SSO and a guidewire 248 is advanced through the sphenoid sinus ostium SSO and into the sphenoid sinus SS. An over-the-wire endoscope 246 (such as a 2.2 mm over-the-wire scope available commercially as Model # AF-28C from Olympus America, Melville, N.Y.) is advanced over the guidewire 248 and is used to examine the interior of the sphenoid sinus SS.

Figure 7G:
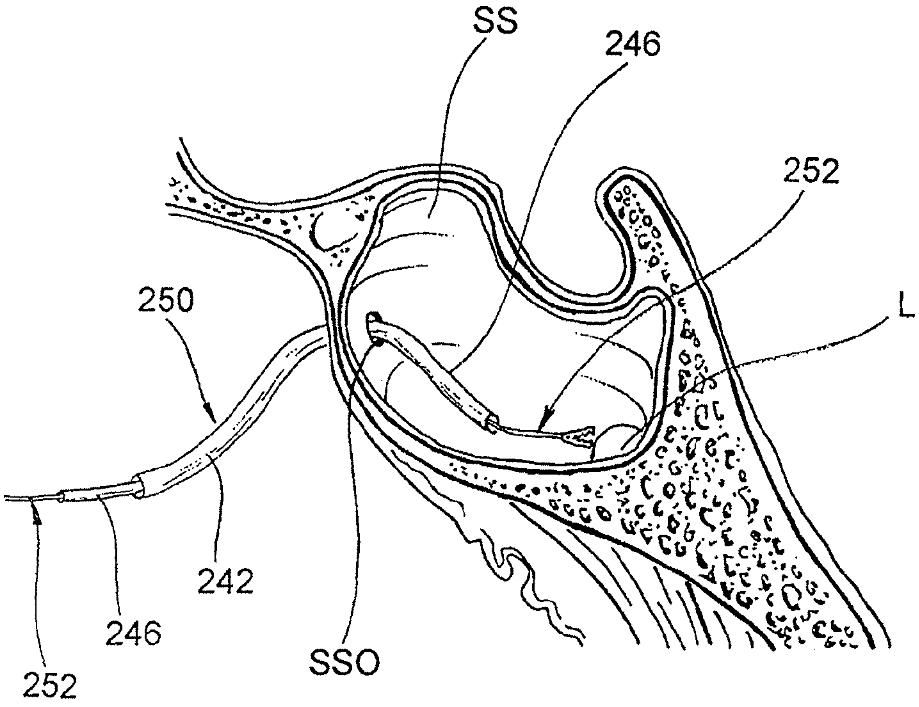
FIG. 7G shows the guide catheter and endoscope of FIG. 5F with a working device (e.g., a biopsy instrument) inserted through a working channel of the endoscope to perform a procedure within the sinus under endoscopic visualization, in accordance with the present invention.

FIG. 7G shows a biopsy system 250 being used to obtain a biopsy specimen from a lesion L within the sphenoid sinus SS. A flexible catheter 242 is positioned in or near the sphenoid sinus ostium SSO and an endoscope 246 is advanced through the catheter 242 and into the interior of the sinus SS. A biopsy instrument 252 is inserted through a working channel of the endoscope 246 and is used, under endoscopic visualization and guidance, to obtain a specimen of the lesion L.

F. General Examples Of Interventions Using the Occluder & Access Devices and/or Working Devices FIGS. 8A-8D show two of many possible examples of methods wherein the occluder & access devices 10, 12 of FIGS. 2A and 2B and/or various working devices such as those shown in FIGS. 5A-5Y"" are used to perform diagnostic and/or therapeutic procedures within the nose, nasopharynx or paranasal sinuses.

In general, diagnostic interventions in accordance with this invention may include: a) anatomic studies where obstructions, sizes, parameters or abnormalities in anatomy are visualized and/or identified, b) dynamic studies where gas, mucous or fluid is introduced into the nose, sinus, nasal cavity, nasopharynx, Eustachian tube, inner or middle ear, etc and the movement of such materials is monitored to asses drainage or gas flow issues and c) perturbation studies where an agent (e.g., an allergen, irritant, agent that induces mucous production, etc.) is introduced into the nose, sinus, nasal cavity, nasopharynx, Eustachian tube, inner or middle ear, etc., and the patient's response and/or flow of the endogenously produced mucous or other secretions is assessed. Examples of procedures that may be used to perform these types of diagnostic interventions include, but are not limited to, the following:

1. Gaining Access To Sinus

Access to one of more of the paranasal sinuses is gained by advancement of catheter(s) into the sinus or sinuses of interest. A guidewire may be inserted into the sinus first and the catheter may then be advanced over the guidewire and into the sinus. In some cases, a sinus ostium guide catheter of the type shown in FIGS. 6A-6E may be inserted into the ostium of the sinus and a smaller catheter may be advanced through the guide catheter. One or more scopes may be used to visualize the sinus ostium and to guide the guidewire and/or catheter into the sinus ostium. In some cases, a steerable guidewire, catheter and/or scope may be used to gain entry into the sinus. In some cases, occlusion & access device(s) such as those shown in FIGS. 2A-2R, may be inserted and the guidewire(s), catheter(s) and/or scope(s) used to access the sinus may be inserted through a device insertion port on the occluder & access device.

2. Mucous Flow Study:

Optionally, after catheter access to the sinus has been gained, an imageable contrast substance or radioactive material such as microbeads or a flowable contrast medium (e.g., an iodinated contrast solution with or without a thickening agent to adjust its viscosity to that of mucous) that may have a consistency similar to that of mucous may be injected into the sinus. An imaging or scanning technique (e.g., X-ray, fluoroscopy, CT scan, ultrasound, MRI, radiation detector, gamma camera, etc.) may then be used to observe the flow of the contrast medium through and out of the sinus. In some cases a fluoroscope with a C-arm may be used in a fashion similar to that used in coronary artery catheterization and angiography procedures to allow the clinician to view the movement of the contrast medium from different vantage points or angles. To facilitate flow of the contrast medium from the sinus, the previously inserted catheter(s) and/or guidewires and/or scope(s) may be backed out of the sinus and ostium or removed completely, to allow normal flow to occur. The patient's head and/or other body parts may be repositioned to observe different postural drainage effects. In this manner, the clinician may specifically locate and identify which anatomical structures are obstructing or interfering with normal mucous flow from the sinus.

3. Air Flow Study:

Optionally, after access to the sinus has been gained as described in No. 1 above, an imageable or traceable gas, such as a radiolabled gas, radiopaque gas or a gas with imageable or radioactive microbeads therein, may be injected through a catheter and into the sinus. An imaging device or tracing device (e.g., radiation detector, gamma camera, X-ray, fluoroscopy, CT scan, ultrasound, MRI) may then be used to observe subsequent movement or dissipation of the gas as it passes out of the sinus and/or equilibrates with other sinus cavities. In this manner, the clinician may determine whether normal gas exchange in the sinus is occurring and may locate and identify any anatomical structures or irregularities that are obstructing or interfering with normal gas flow and/or gas exchange.

4. Anatomic Dimension Study:

An entire paranasal sinus or other anatomical passageway or structure may be filled with an imageable substance or otherwise measured to determine its actual dimensions and/or configuration. In some such studies, access to a paranasal sinus will be gained as described in No. 1 above and the sinus may be filled with an imageable substance (e.g., contrast medium). A suitable imaging technique (e.g., X-ray, fluoroscopy, CT scan, ultrasound, MRI, radiation detector, gamma camera, etc.) may then be used to determine the size and shape of the sinus. Again, in such procedure, a moveable imaging apparatus such as a fluoroscope with a C-arm may be used to view and measure the contrast filled sinus from different vantage points or angles. One example of such a procedure is shown in FIG. 7B and described hereabove.

5. Endoscopic Study:

A flexible and/or steerable endoscope, as described above, may be inserted into the nose, sinus, nasal cavity, nasopharynx, Eustachian tube, inner or middle ear, etc and used to visually examine the anatomy and/or to observe a treatment and/or to assess the efficacy or completeness of a previously rendered treatment. In cases where it is desired to view the interior of a paranasal sinus, access to the sinus may be gained as described in No. 1 above and the endoscope may be advanced into the interior of the sinus either directly or over a guidewire.

6. Transillumination Study:

A flexible light emitting instrument (e.g., a catheter having a powerful light emitting apparatus at its distal end) may be advanced into the nose, paranasal sinus, nasal cavity, nasopharynx, Eustachian tube, inner or middle ear, etc and used to illuminate anatomical structures. Direct or endoscopic observation may then be made from outside the body and/or from other locations within the nose, sinus, nasal cavity, nasopharynx, Eustachian tube, inner or middle ear, orbit, cranial vault, etc. to observe anatomical structures and/or to detect aberrant openings or leaks through which the light passes. In cases where the light emitter and/or the viewing instrument (e.g., endoscope) is/are positioned within paranasal sinus(es) access to the sinus(es) may be gained as described in No. 1 above and the light emitter and/or viewing instrument may then be advanced into the sinus(es) either directly or over guidewire(s).

7. Other Imaging Studies:

Other imaging techniques such as MRI, CT, etc. in combination with any of the modalities set forth in Nos. 1-6 above and modifications may be made to any of those techniques to adjust for sinus anatomy or other pathology.

After any or all of the elected diagnostic studies have been completed, one or more working devices, such as the flexible devices described herein and shown in FIGS. 5A-5Y'''', may be inserted and used to perform therapeutic procedure(s).

Figure 8A:
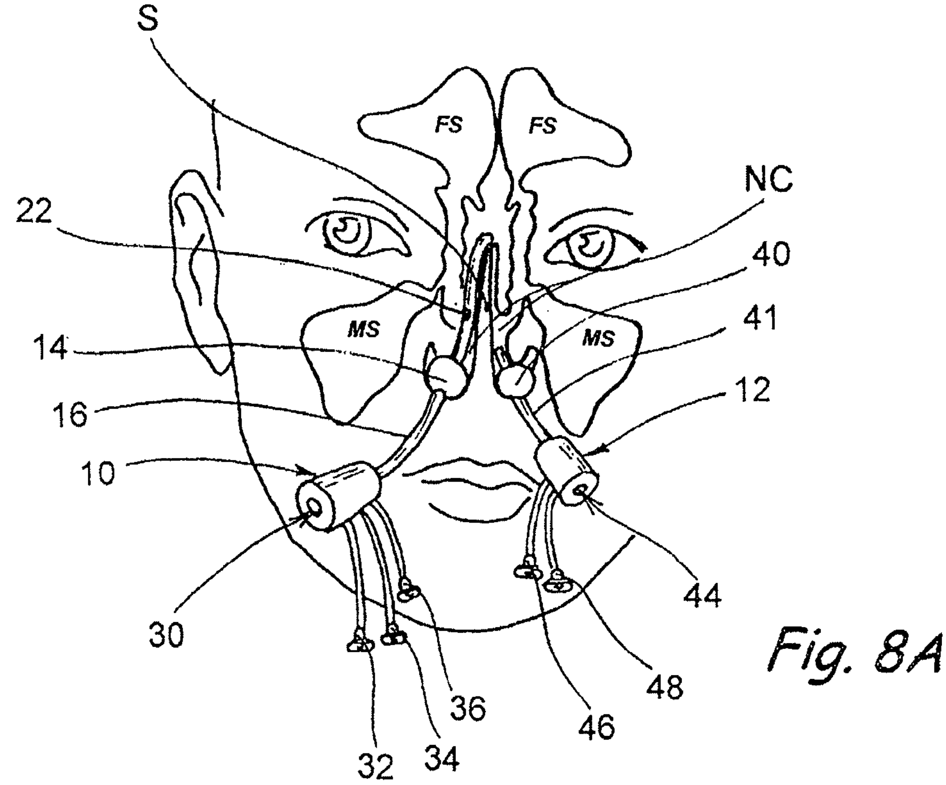
FIGS. 8A-8E show steps in a sinus treatment procedure conducted in accordance with the present invention.

As shown in the example of FIG. 8A, an anterior/posterior occluder & access device 10 is inserted through the right nasal cavity NC. The device's anterior occluder 14 is positioned to occlude the nostril on the right side while its posterior occluder (not seen in FIGS. 8A-8E) occludes the posterior choanae or nasopharynx. An anterior occluder & access device 12 is inserted into the left nasal cavity and its occluder 40 occludes the left nostril. In this manner, a sealed operative field is established between the posterior occluder positioned in the posterior choanae or nasopharynx and the anterior occluders 14, 40 positioned in the right and left nostrils or anterior nasal cavities.

Figure 8B:
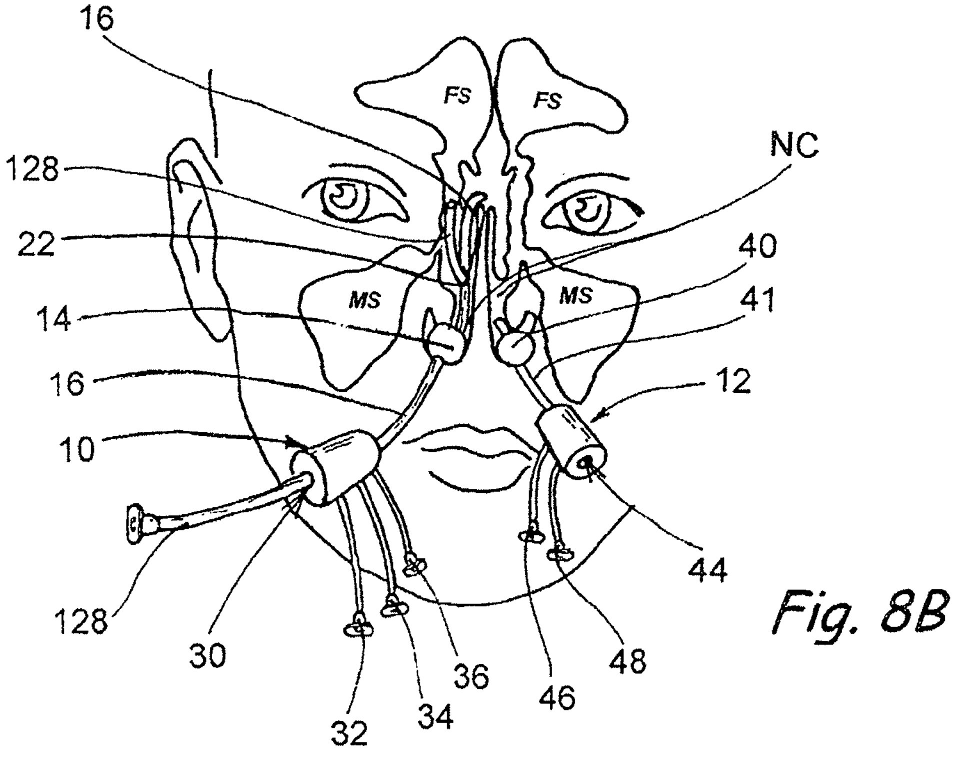
Figure 8C:
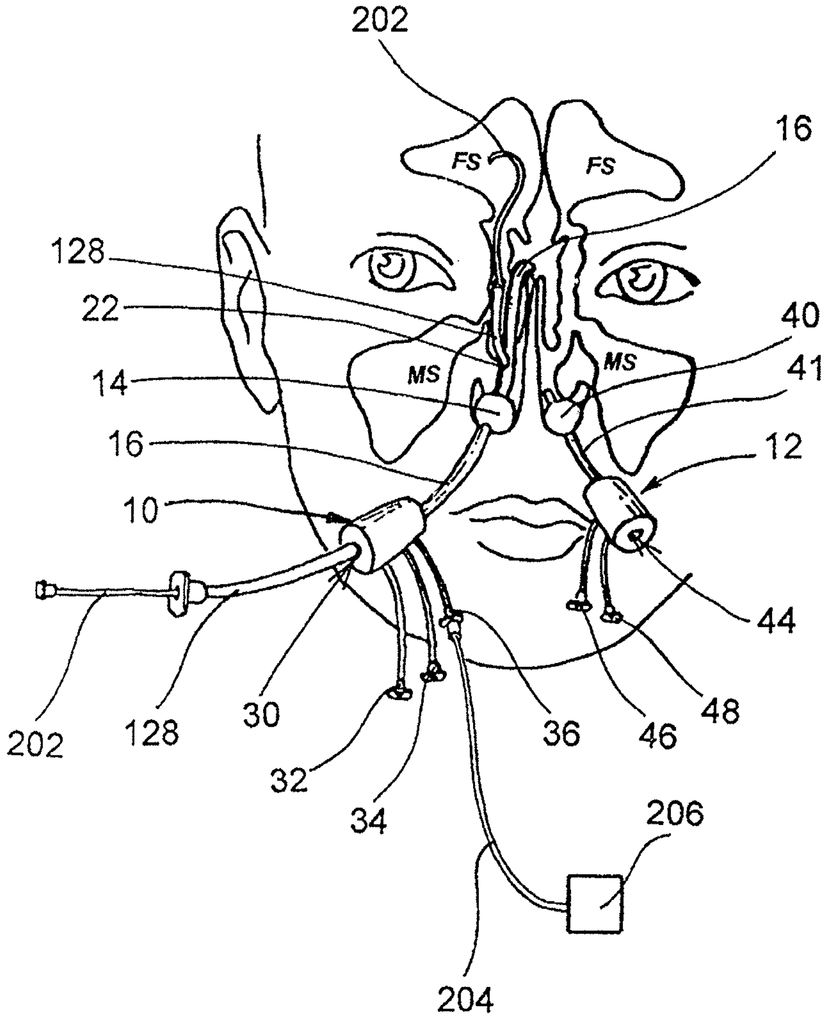

FIGS. 8B-8C show an example of a method for performing a diagnostic and/or therapeutic procedure in the right frontal sinus FS in the patient in whom the occluder & access devices 10, 14 have been inserted. In FIG. 8B, a frontal sinus guide catheter 128 is inserted into the working device insertion port 30 and advanced through tube 16 and out of outlet aperture 22. The guide catheter 128 is then advanced to a position where its distal end is in the right frontal sinus ostium.

In FIG. 8C, a working device 202 is inserted through the guide catheter 128 and into the frontal sinus FS. This working device 202 may comprise any of the devices shown in FIG. 5A-5Y'''' or 7A-7G. In some procedures, it may be desired to initially introduce a contrast agent into the frontal sinus FS and pull back the guide catheter 128 to allow the contrast agent to drain from the sinus. Imaging of the draining contrast agent may be used to diagnose drainage impairment and to identify the specific anatomical structures that are causing the impairment of drainage. Thereafter, the guide catheter may be reinserted into the frontal sinus ostium and the working device(s) 202 may be used to modify the structures that have been identified and impairments to drainage. Thereafter, the contrast injection and imaging steps may be repeated to assess whether the procedure(s) performed have overcome or corrected the drainage problem that had been initially diagnosed. A suction device 206 is connected by way of suction line 204 to port 36 to suction blood, other fluid or debris from the operative field during the procedure.

Figure 8D:
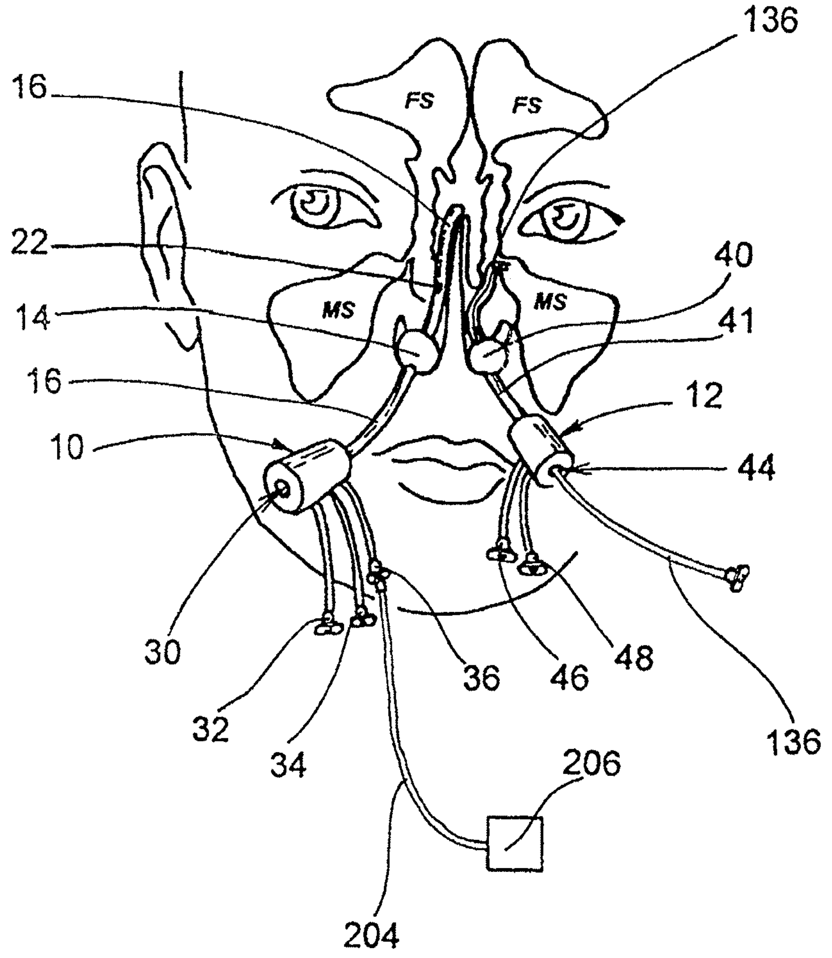
Figure 8E:
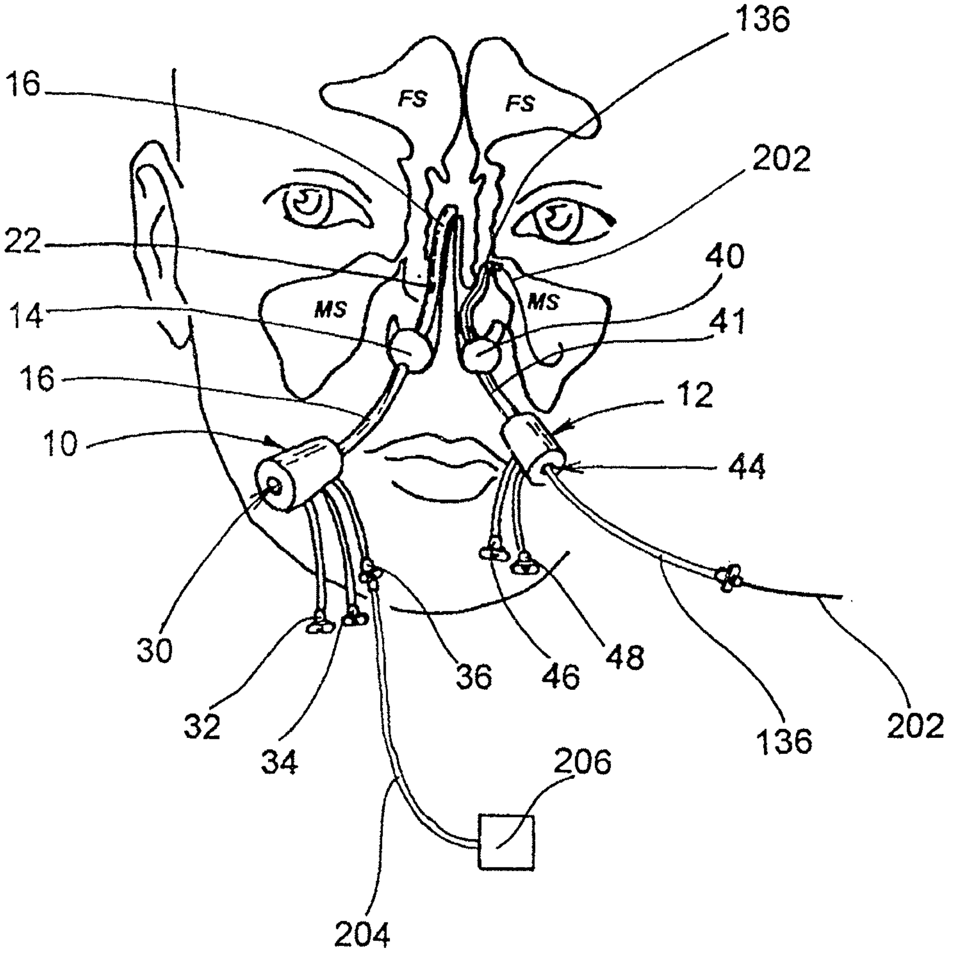

FIGS. 8D and 8E show an example of a treatment rendered to the left maxillary sinus MS, in the same patient in whom the occluder & access devices 10, 14 have been inserted. In FIG. 8D, a guide catheter 136 is inserted into device insertion aperture 44 and advanced through tube 41 to a position where the distal end of the guide catheter 136 is positioned in the ostium of the maxillary sinus MS.

Thereafter, as shown in FIG. 8E, a working device 202 is inserted through the guide catheter 136 and into the maxillary sinus MS. This working device 202 may comprise any of the devices shown in FIG. 5A-Y'''' or 7A-7G. In some procedures, it may be desired to initially introduce a contrast agent into the maxillary sinus MS by the same procedure described above in reference to FIGS. 8B and 8C.

After all of the desired procedures have been completed, the anterior occluders 14, 40 and posterior occluder (not shown on FIGS. 8A-8E) are collapsed (e.g., deflated) and the occluder & access devices as well as the guide catheters and working devices are removed (except for implants such as stents, embolic coils, substance delivery implants, etc.).

G. Cochlear Implant Procedure

Figure 9A:
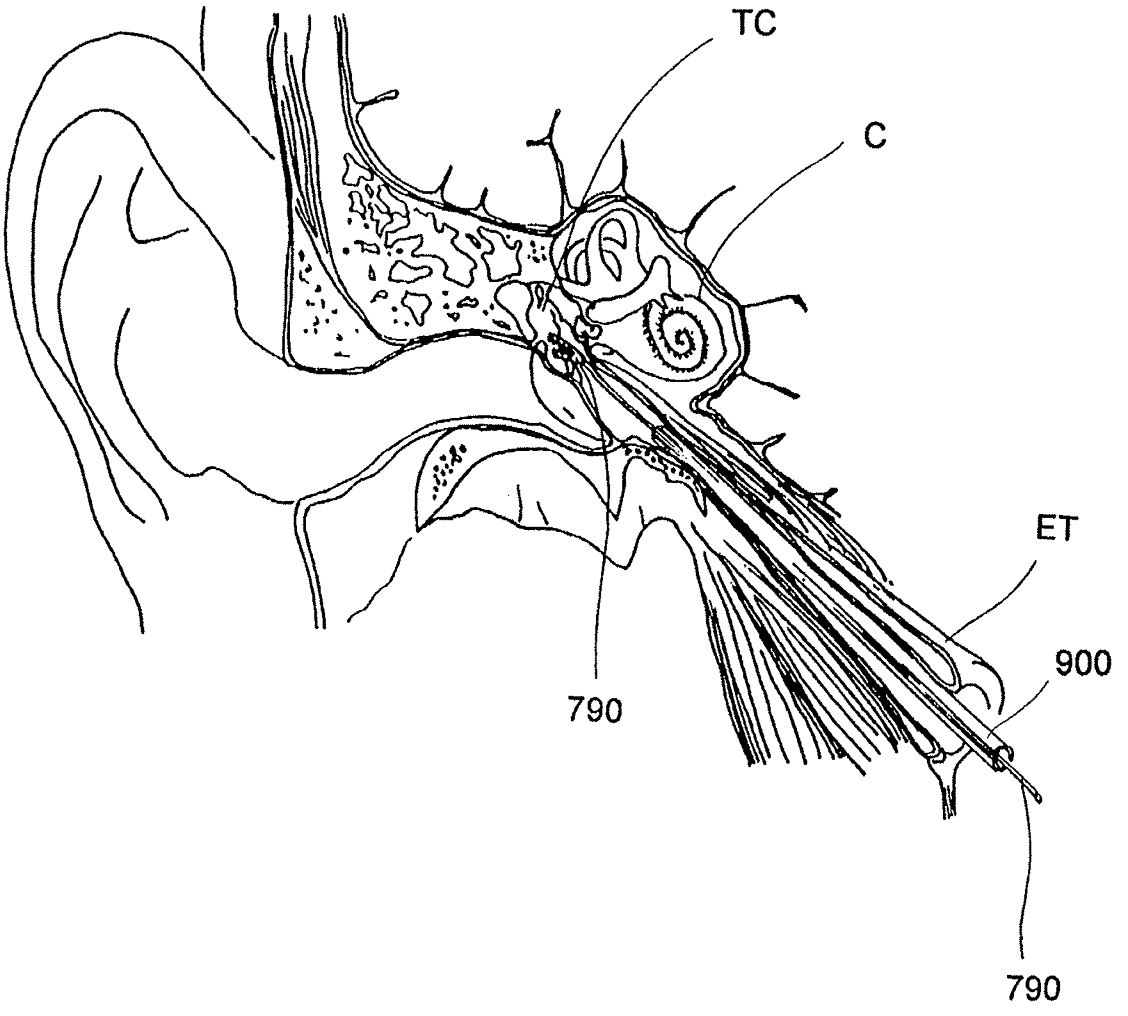
FIGS. 9A-9C show steps in a cochlear implant procedure conducted in accordance with the present invention.
Figure 9B:
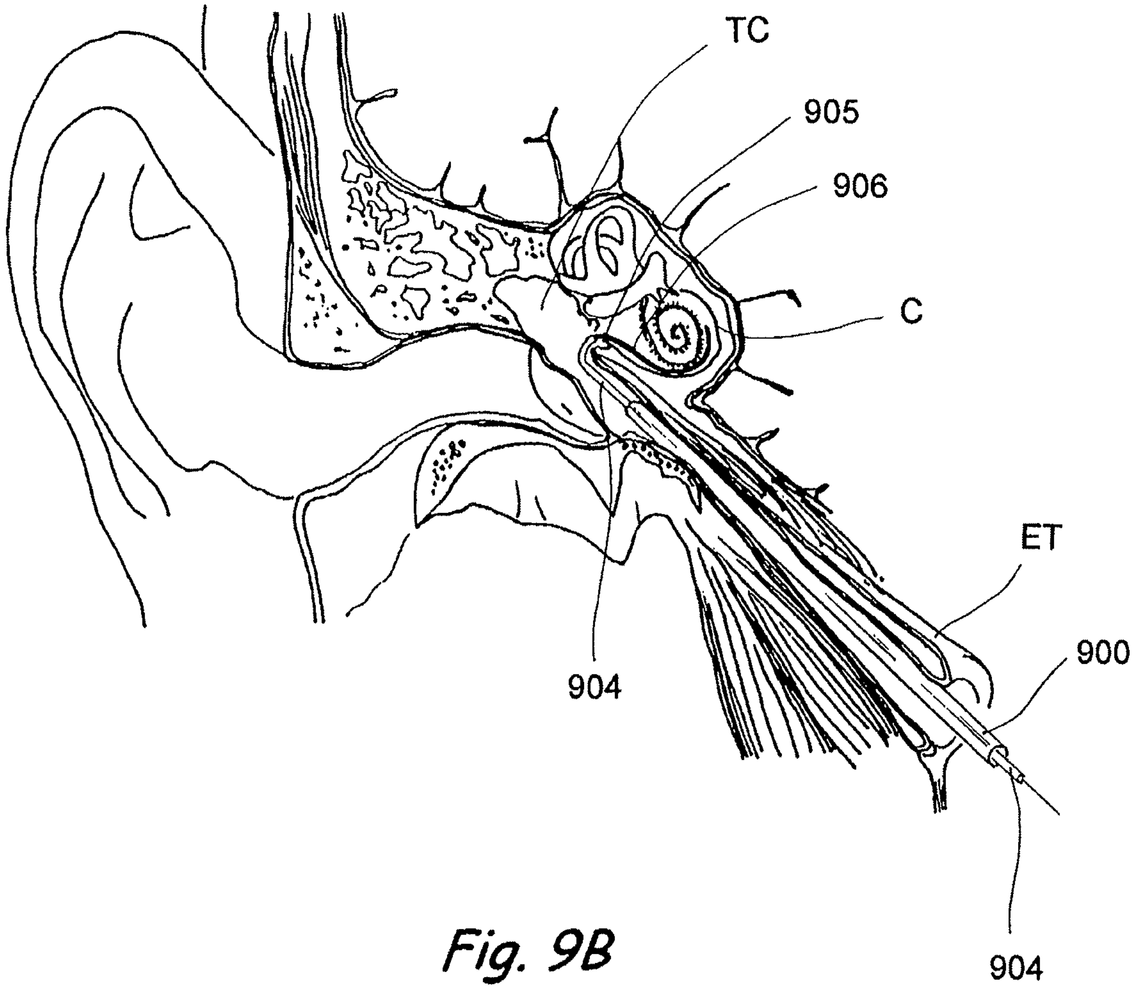
Figure 9C:
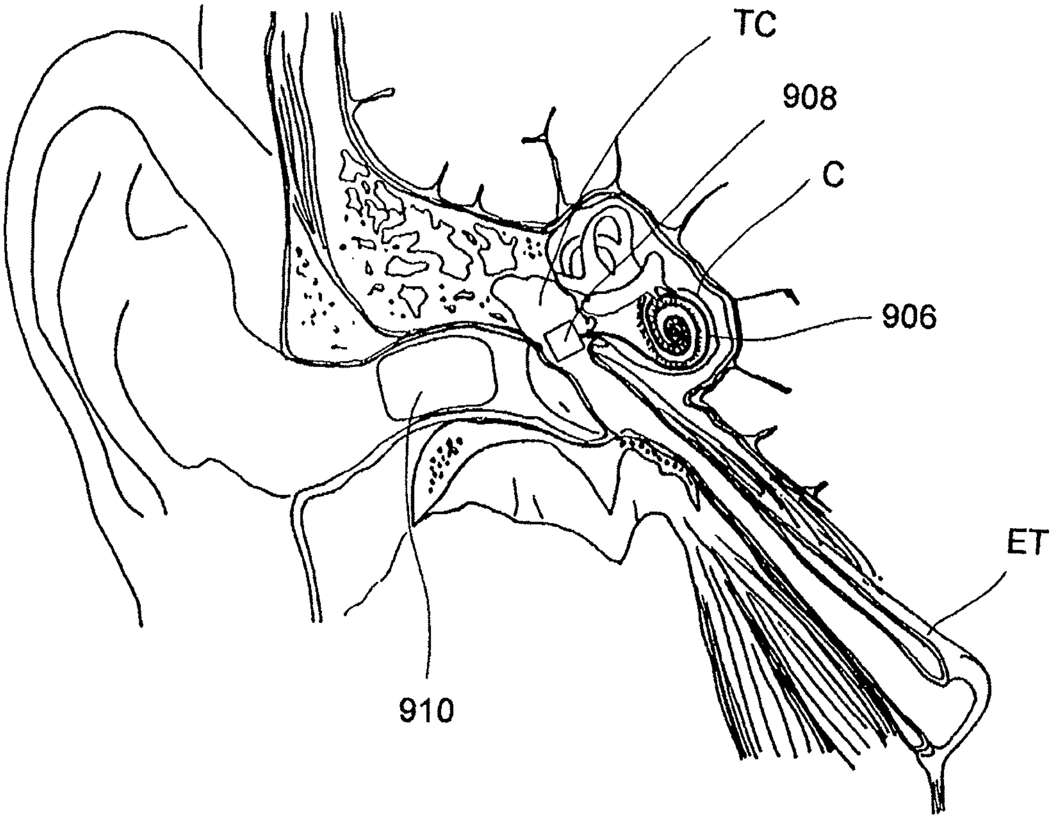

FIGS. 9A-9C show a procedure for installation of a cochlear implant in accordance with the present invention. In this procedure, the nasopharyngeal opening into the Eustachian tube ET is located and a guidewire is initially advanced into the Eustachian tube ET. A catheter 900 is advanced over the guidewire to a location where the distal end of the catheter 900 is in or near the tympanic cavity TC of the middle ear. Thereafter, if deemed necessary, a forceps device 790 and/or other devices are advanced through the catheter 900 and used to remove the small bones of the sear (i.e., the malleus, incus and stirrup) as shown in FIG. 9A. This optional removal of the bones of the middle ear may be done under endoscopic visualization using an endoscope equipped device such as the endoscope equipped forceps device 790 shown in FIG. 5T and described above. As shown in FIG. 9B, a cochlear guide catheter 904 having a "J" shaped distal tip 905 is advanced through the catheter 900 to a position where the tip 905 of the cochlear guide catheter 904 is directed into or inserted into the cochlea C. In some applications, the cochlear guide catheter 904 may be configured to advance into the round window of the cochlea and through the secondary tympanic membrane that covers the round window. If necessary, a penetrator such as a needle, drill or cutter may be advanced through or formed or positioned on the distal end of the cochlear guide catheter 904 to penetrate through the secondary tympanic membrane.

In other applications, the cochlear guide catheter 904 may be positioned adjacent to the cochlea and a cochleostomy device (e.g., a penetrator such as a drill, needle or cutter) may be advanced through or formed or positioned on the distal end of the cochlear guide catheter 904 and used to form a cochleostomy through which the distal end of the guide catheter 904 is advanced into the cochlea C. Thereafter, a cochlear electrode array 906 is advanced through the cochlear guide catheter 904 and into the cochlea, as seen in FIG. 9B. One example of a commercially available cochlear electrode array is the Nucleus 24 Countour device manufactured by Cochlear Corporation.

Thereafter, a sound receiving device or transducer 908 is advanced through the catheter 900 and positioned in the tympanic cavity TC. The sound receiving device or transducer 908 may be of any type that is a) sufficiently small to pass through the Eustachian tube ET and into the tympanic cavity TC and b) useable to perform the desired function of converting sound waves to electrical impulses and delivering such electrical impulses to the cochlear electrode array 906. A microphone/power/electronics device 910 may be positioned in the outer ear canal, as shown in FIG. 9C or may be implanted subcutaneously or in any other way that is acceptable. Certain non-limiting examples of devices 906, 908, 910 that may be useable for this procedure are set forth in PCT International Patent Publication No. WO 2004/018980 A2 designating the United States, the entirety of which is expressly incorporated herein by reference.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

We claim:

1. A system comprising:

(a) a light emitting wire having a proximal end, a distal end, and a light emitting portion at or near the distal end, wherein the light emitting portion is configured to pass into a paranasal sinus;

(b) a guide catheter configured to facilitate advancement of the light emitting portion of the light emitting wire into the paranasal sinus, wherein the light emitting wire is passable through the guide catheter; and (c) a flexible catheter passable over the light emitting wire;

wherein the light emitting wire and the flexible catheter are configured and operable such that a distal end of the flexible catheter is positionable proximal to a distal end of the light emitting wire while the light emitting wire is disposed in the flexible catheter, such that the distal end of the light emitting wire is distal to the distal end of the flexible catheter;

wherein the light emitting wire is operable to emit light of a character such that emitted light is directly observable exterior of a patient's anatomy through tissue overlaying the paranasal sinus.

2. A system as in claim 1, wherein the flexible catheter is passable over the light emitting wire through the guide catheter.

3. A system as in claim 1, further comprising a paranasal sinus ostium enlargement device.

4. A system as in claim 1, further comprising an endoscope.

5. A system as in claim 4, wherein the endoscope comprises a flexible endoscope.

6. A system as in claim 5, further comprising an articulation member coupled with the endoscope to cause a distal, flexible portion of the endoscope to articulate.

7. A system as in claim 1, wherein the guide catheter defines a first lumen, wherein the flexible catheter is configured to slide through the first lumen, wherein the flexible catheter defines a second lumen.

8. A system as in claim 7, wherein the flexible guidewire is configured to slide through the second lumen.

9. A system as in claim 1, wherein the flexible catheter includes an inflatable feature operable to transition between a first configuration and a second configuration, wherein the inflatable feature is configured to be inserted within a sinus ostium in the first configuration, wherein the inflatable feature is configured to dilate the sinus ostium in the second configuration.

10. A system comprising:

(a) a light emitting wire having a proximal end, a distal end, and a light emitting portion at or near the distal end, wherein the light emitting portion is configured to pass into a paranasal sinus;

(b) a guide catheter configured to facilitate advancement of the light emitting portion of the light emitting wire into the paranasal sinus, wherein the light emitting wire is passable through the guide catheter; and (c) a flexible catheter passable over the light emitting wire from a proximal position to a distal position, wherein the flexible catheter defines a distal opening, wherein the light emitting wire is configured and operable to pass through the distal opening of the flexible catheter.

11. A system comprising:

(a) a light emitting wire having a proximal end, a distal end, and a light emitting portion at or near the distal end, wherein the light emitting portion is configured to pass into a paranasal sinus;

(b) a guide catheter configured to facilitate advancement of the light emitting portion of the light emitting wire into the paranasal sinus; and (c) a flexible catheter, wherein the flexible catheter is configured and operable to pass over the light emitting wire from a proximal position to a distal position, wherein the flexible catheter is further configured and operable to pass through the guide catheter.

* * * * *